US011319551B2

(12) United States Patent
Evdokimov et al.

(10) Patent No.: US 11,319,551 B2
(45) Date of Patent: *May 3, 2022

(54) METHODS AND COMPOSITIONS FOR PPO HERBICIDE TOLERANCE IN PLANTS

(71) Applicant: Monsanto Technology LLC, St. Louis, MO (US)

(72) Inventors: Artem G. Evdokimov, Orchard Park, NY (US); Clayton T. Larue, Chesterfield, MO (US); Farhad Moshiri, Chesterfield, MO (US); Joel E. Ream, St. Louis, MO (US); Xuefeng Zhou, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 104 days.

This patent is subject to a terminal disclaimer.

(21) Appl. No.: 16/452,349

(22) Filed: Jun. 25, 2019

(65) Prior Publication Data

US 2019/0382788 A1  Dec. 19, 2019

Related U.S. Application Data

(62) Division of application No. 15/228,993, filed on Aug. 4, 2016, now Pat. No. 10,378,023.

(60) Provisional application No. 62/323,852, filed on Apr. 18, 2016, provisional application No. 62/212,716, filed on Sep. 1, 2015.

(51) Int. Cl.
| | |
|---|---|
| *C12N 15/82* | (2006.01) |
| *C12N 9/02* | (2006.01) |
| *A01N 43/84* | (2006.01) |
| *A01N 43/90* | (2006.01) |
| *A01N 43/653* | (2006.01) |
| *A01N 43/82* | (2006.01) |
| *A01N 43/56* | (2006.01) |
| *A01N 43/54* | (2006.01) |
| *C12Q 1/6895* | (2018.01) |
| *A01N 33/22* | (2006.01) |
| *A01N 37/48* | (2006.01) |
| *A01N 41/06* | (2006.01) |

(52) U.S. Cl.
CPC ......... *C12N 15/8274* (2013.01); *A01N 33/22* (2013.01); *A01N 37/48* (2013.01); *A01N 41/06* (2013.01); *A01N 43/54* (2013.01); *A01N 43/56* (2013.01); *A01N 43/653* (2013.01); *A01N 43/82* (2013.01); *A01N 43/84* (2013.01); *A01N 43/90* (2013.01); *C12N 9/001* (2013.01); *C12Q 1/6895* (2013.01); *C12Y 103/03004* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 6,905,852 B1* | 6/2005 | Horikoshi | C12N 9/001 |
| | | | 435/189 |
| 10,378,023 B2* | 8/2019 | Evdokimov ... | C12Y 103/03004 |
| 10,745,712 B2* | 8/2020 | Larue | C12N 15/8221 |
| 11,124,803 B2 | 9/2021 | LaRue et al. | |
| 2003/0233675 A1 | 12/2003 | Cao et al. | |
| 2007/0050863 A1 | 3/2007 | Tranel et al. | |
| 2014/0123340 A1* | 5/2014 | Aponte | C12Y 103/03004 |
| | | | 800/278 |
| 2017/0037427 A1 | 2/2017 | Evdokimov et al. | |
| 2017/0175131 A1 | 6/2017 | Ellis et al. | |
| 2018/0044690 A1 | 2/2018 | Larue et al. | |
| 2019/0185873 A1 | 6/2019 | Larue et al. | |
| 2021/0002663 A1* | 1/2021 | Larue | C12N 15/8277 |

FOREIGN PATENT DOCUMENTS

| | | |
|---|---|---|
| WO | WO 95/34659 A1 | 12/1995 |
| WO | WO 98/33927 A1 | 8/1998 |
| WO | 2012080975 | 6/2012 |
| WO | 2015027258 A2 | 3/2015 |
| WO | 2015/092706 | 6/2015 |
| WO | 2016203377 A1 | 12/2016 |
| WO | 2017/198859 | 11/2017 |
| WO | 2018/022777 | 2/2018 |

OTHER PUBLICATIONS

Glavina Del Rio et al., 2010, Complete genome sequence of Chitinophaga pinensis type strain (UQM 2034T), Standards in Genomic Sciences 2: 87-95.*
Chitinophaga pinensis protoporphyrinogen oxidase, UniProtKB Accession No. C7PKZ1, published Oct. 13, 2009.*
Hao et al., 2011, Protoporphyrinogen oxidase inhibitor: an ideal target for herbicide discovery, CHIMIA 65: 961-969.*
Keskin et al., 2004, A new, structurally nonredundant, diverse data set of protein-protein interfaces and its implications, Protein Science 13: 1043-1055.*
Guo et al., 2004, Protein tolerance to random amino acid change, Proceedings of the National Academy of Sciences USA 101: 9205-9210.*

(Continued)

*Primary Examiner* — Bratislav Stankovic

(74) *Attorney, Agent, or Firm* — Dentons US LLP; Elizabeth Millard

(57) ABSTRACT

The invention relates to biotechnology and provides novel recombinant DNA molecules and engineered proteins for conferring tolerance to protoporphyrinogen oxidase-inhibitor herbicides. The invention also provides herbicide tolerant transgenic plants, seeds, cells, and plant parts containing the recombinant DNA molecules, as well as methods of using the same.

25 Claims, 2 Drawing Sheets

Specification includes a Sequence Listing.

(56) References Cited

OTHER PUBLICATIONS

Thornton et al., 2000, From structure to function: approaches and limitations, Nature Structural Biology, structural genomic supplement, Nov. 2000: 991-994.*
USPTO: Notice of Allowance and Fee(s) Due regarding U.S. Appl. No. 15/660,660, dated Apr. 14, 2020.
U.S. Appl. No. 16/452,305, filed Jun. 25, 2019, Evdokimov et al.
U.S. Appl. No. 16/452,327, filed Jun. 25, 2019, Evdokimov et al.
Nishimura et al., "Cloning and Identification of the hemG Gene Encoding Protoporphyrinogen Oxidase (PPO) of *Escherichia coli* K-12", DNA Research 2 (1):1-8 (1995).
Partial Supplementary European Search Report regarding Europe Application No. 16842539.5, dated May 7, 2019.
EBI Accession No. ACU63901, dated Aug. 21, 2009.
USPTO: Notice of Allowance regarding U.S. Appl. No. 15/224,276, dated May 1, 2019.
USPTO: Non-Final Office Action regarding U.S. Appl. No. 15/224,276, dated Mar. 7, 2018.
Response to Non-Final Office Action regarding U.S. Appl. No. 15/224,276, dated Jun. 6, 2018.
USPTO: Final Office Action regarding U.S. Appl. No. 15/224,276, dated Jul. 24, 2018.
Response to Final Office Action regarding U.S. Appl. No. 15/224,276, dated Dec. 5, 2018.
USPTO: Non-Final Office Action regarding U.S. Appl. No. 15/224,276, dated Feb. 15, 2019.
Response to Non-Final Office Action regarding U.S. Appl. No. 15/224,276, dated Apr. 5, 2019.
International Search Report and Written Opinion regarding International Application No. PCT/US2016/046041, dated Dec. 28, 2017.
GenBank Accession No. CP001699, dated Dec. 24, 2013.
UniProtKB Accession No. C7PKZ1_CHIPD, dated Oct. 13, 2009.
Boynton et al., "Discovery of a gene involved in a third bacterial protoporphyrinogen oxidase activity through comparative genomic analysis and functional complementation," Appl Environ Microbiol, 77:4795-4801, 2011.
Hansson et al., "Cloning and characterization of the Bacillus subtilst hemEHY gene cluster, which encodes protoheme IX biosynthetic enzymes," J Bacteriol, 174:8081-8093, 1992.
Sasarman et al., "Mapping of a new hem gene in *Escherichia coli* K12," J Gen Microbiol, 113:297-303, 1979.
Sasarman et al., "Nucleotide sequence of the hemG gene involved in the protoporphyrinogen oxidase activity of *E. coli* K12," Can J Microbiol, 39:1155-161, 1993.
Guo et al., Proceedings of the National Academy of Sciences USA 101:9205-9210, 2004.
Hao et al., CHIMIA 65:961-969, 2011.
Accession No. C7PKZ1, Sequence of a protoporphyrinogen oxidase with a UniProtKb, published Oct. 13, 2009.
Keskin e t al., Protein Science 13: 1043-1055, 2004.
Thornton et al., Nature Structural Biology, structural genomic Supplement, Nov. 2000: 991-994.
U.S. Appl. No. 16/931,427, filed Jul. 16, 2020, Larue et al.
Uniprot A0A085G3K7 Full=Oxygen-independent protoporphyrinogen IX oxidase. [online] Mar. 27, 2015 [retrieved Oct. 5, 2016]. Available on the internet: <URL:http://www.uniprot.org/uniprot/A0A085G3K7.txt?version=4>.
GenBank Accession No. CP002505.1, dated Jan. 7, 2015.
Dailey et al., "Expression of a Cloned Protoporphyrinogen Oxidase," The Journal of Biological Chemistry 269(2):813-815,1994.
Sasarman et al., "Nucleotide Sequence of the hemG gene involved in the protoporphyrinogen oxidase activity of *Escherichia coli* K12," Canadian Journal of Microbiology 39(12):1155-1161, 1993.
GenBank Accession No. WP_034794962, dated Jun. 20, 2019.
USPTO: Notice of Allowance regarding U.S. Appl. No. 16/218,822, dated May 14, 2021.
GenBank Accession No. JMPJ01000000.1, dated Jul. 28, 2014.
Hara et al., The complete genome sequence of Pantoea ananatis AJ13355, an organism with great biological potential, Appl. Microbiol. Biotechnol 93(1): 331-341, 2012.
USPTO: Notice of Allowance regarding U.S. Appl. No. 16/452,327, dated Aug. 13, 2021.
USPTO: Response to Non-Final Office Action regarding U.S. Appl. No. 16/452,305, filed Jun. 17, 2021.
USPTO: Final Office Action regarding U.S. Appl. No. 16/452,305, dated Jul. 14, 2021.
USPTO: Response to Non-Final Office Action regarding U.S. Appl. No. 16/452,327, filed Jul. 7, 2021.
USPTO: Non-Final Office Action regarding U.S. Appl. No. 16/452,327, dated Apr. 9, 2021.
UniProtKB Accession No. A0A093V7L1, dated Nov. 26, 2014.
UniProtKB Accession No. C6DHI2, dated Sep. 1, 2009.
USPTO: Non-Final Office Action regarding U.S. Appl. No. 16/452,305, dated Apr. 6, 2021.
U.S. Appl. No. 17/522,737, filed Nov. 9, 2021, Evdokimov et al.
U.S. Appl. No. 17/404,857, filed Aug. 17, 2021, LaRue et al.

* cited by examiner

SEQUENCE LISTING

<160> NUMBER OF SEQ ID NOS: 81

<210> SEQ ID NO 1
<211> LENGTH: 442
<212> TYPE: PRT
<213> ORGANISM: Xanthomonas campestris

<400> SEQUENCE: 1

Met Gln Thr Gln Pro Val Ile Ile Ala Gly Ala Gly Ile Ala Gly Leu
1               5                   10                  15

Ser Ile Ala Tyr Glu Leu Gln Gln Lys Gly Ile Pro Tyr Glu Ile Met
            20                  25                  30

Glu Ala Ser Ser Tyr Ala Gly Val Val Lys Ser Leu His Ile Asp
        35                  40                  45

Gly Tyr Glu Leu Asp Ala Gly Pro Asn Ser Leu Ala Ala Ser Ala Ala
    50                  55                  60

Phe Met Ala Tyr Ile Asp Gln Leu Gly Leu Gln Asp Gln Val Leu Glu
65                  70                  75                  80

Ala Ala Ala Ala Ser Lys Asn Arg Phe Leu Val Arg Asn Asp Lys Leu
                85                  90                  95

His Ala Val Ser Pro His Pro Phe Lys Ile Leu Gln Ser Ala Tyr Ile
            100                 105                 110

Ser Gly Gly Ala Lys Trp Arg Leu Phe Thr Glu Arg Phe Arg Lys Ala
        115                 120                 125

Ala Ala Pro Glu Gly Glu Thr Val Ser Ser Phe Val Thr Arg Arg
130                 135                 140

Phe Gly Lys Glu Ile Asn Asp Tyr Leu Phe Glu Pro Val Leu Ser Gly
145                 150                 155                 160

Ile Tyr Ala Gly Asn Pro Asp Leu Met Ser Val Gly Glu Val Leu Pro
                165                 170                 175

Met Leu Pro Gln Trp Glu Gln Lys Tyr Gly Ser Val Thr Gln Gly Leu
            180                 185                 190

Leu Lys Asn Lys Gly Ala Met Gly Gly Arg Lys Ile Ile Ala Phe Lys
    195                 200                 205

Gly Gly Asn Ala Thr Leu Thr Asn Arg Leu Gln Ser Leu Leu Ser Gly
210                 215                 220

Lys Ile Arg Phe Asn Cys Ala Val Thr Gly Val Thr Arg Gly Ala Asp
225                 230                 235                 240

Asp Tyr Ile Val Gln Tyr Thr Glu Asn Gly Asn Thr Ala Met Leu Asn
                245                 250                 255

Ala Ser Arg Val Ile Phe Thr Thr Pro Ala Tyr Ser Thr Ala Val Ala
            260                 265                 270

Ile Gln Ala Leu Asp Ala Ser Leu Ala Thr His Leu Ser Asp Val Pro
    275                 280                 285

Tyr Pro Arg Met Gly Val Leu His Leu Gly Phe Gly Ala Glu Ala Arg
290                 295                 300

Gln Lys Ala Pro Ala Gly Phe Gly Phe Leu Val Pro His Ala Ala Gly
305                 310                 315                 320

Lys His Phe Leu Gly Ala Ile Cys Asn Ser Ala Ile Phe Pro Ser Arg
                325                 330                 335

Val Pro Thr Gly Lys Val Leu Phe Thr Val Phe Leu Gly Gly Ala Arg
            340                 345                 350

Gln Glu Gln Leu Phe Asp Gln Leu Gly Pro Glu Lys Leu Gln Gln Thr
    355                 360                 365

Val Val Lys Glu Leu Met Glu Leu Leu Gly Leu Thr Thr Pro Pro Glu
370                 375                 380

Met Gln Arg Phe Ser Glu Trp Asn Arg Ala Ile Pro Gln Leu Asn Val
385                 390                 395                 400

Gly Tyr Ala Gln Thr Arg Gln Gln Ile Gly Val Phe Glu Gln Arg Tyr
                405                 410                 415

-continued

Pro Gly Ile Arg Leu Ala Gly Asn Tyr Val Thr Gly Val Ala Val Pro
              420                 425                 430

Ala Ile Ile Gln Ala Ala Lys Gly Tyr Cys
              435                 440

<210> SEQ ID NO 2
<211> LENGTH: 448
<212> TYPE: PRT
<213> ORGANISM: Chitinophaga pinensis

<400> SEQUENCE: 2

Met Ser Asp Gln Pro Val Leu Ile Val Gly Ala Gly Leu Ser Gly Leu
1               5                   10                  15

Ser Ile Ala Tyr Glu Leu Gln Lys Leu Gln Val Pro Tyr Gln Val Leu
                20                  25                  30

Glu Val Ser Gly His Ser Gly Val Met Lys Ser Leu Arg Lys Asp
            35                  40                  45

Gly Phe Glu Leu Asp Ala Gly Ala Asn Thr Ile Ala Ala Ser Pro Glu
    50                  55                  60

Ile Leu Ala Tyr Phe Thr Ser Leu Gly Leu Glu Asn Glu Ile Leu Gln
65                  70                  75                  80

Ala Thr Ala Ala Ser Lys His Arg Phe Leu Val Arg Arg Gln Leu
                85                  90                  95

His Ala Val Ser Pro His Pro Phe Lys Ile Met Ser Ser Pro Tyr Leu
            100                 105                 110

Ser Arg Gly Ser Lys Trp Arg Leu Phe Thr Glu Arg Phe Arg Lys Pro
        115                 120                 125

Val Val Ala Ser Gly Glu Glu Thr Val Thr Asp Phe Ile Thr Arg Arg
    130                 135                 140

Phe Asn Arg Glu Ile Ala Glu Tyr Val Phe Asp Pro Val Leu Ser Gly
145                 150                 155                 160

Ile Tyr Ala Gly Asn Pro Asp Gln Met Ser Ile Ala Glu Val Leu Pro
                165                 170                 175

Ala Leu Pro Arg Trp Glu Arg Glu Tyr Gly Ser Val Thr Lys Gly Leu
            180                 185                 190

Met Lys Asp Lys Gly Ala Met Gly Gly Arg Lys Ile Ile Ser Phe Lys
        195                 200                 205

Gly Gly Asn Gln Leu Leu Thr Asn Arg Leu Gln Gln Leu Leu Thr Thr
    210                 215                 220

Pro Val Arg Phe Asn Cys Lys Val Thr Gly Ile Thr Ala Ser Asn Gly
225                 230                 235                 240

Gly Tyr Ile Val Ser Ala Val Glu Asp Gly Val Ser Glu Ser Tyr Thr
                245                 250                 255

Ala Ser Arg Val Ile Leu Thr Thr Pro Ala Tyr Ser Ala Ala Ala Thr
            260                 265                 270

Ile Thr Asn Leu Asp Ala Ala Thr Ala Ala Leu Leu Asn Glu Ile His
        275                 280                 285

Tyr Pro Arg Met Gly Val Leu His Leu Gly Phe Asp Ala Thr Ala Leu
    290                 295                 300

Pro Gln Pro Leu Asp Gly Phe Gly Phe Leu Pro Asn Ala Glu Asn
305                 310                 315                 320

Met His Phe Leu Gly Ala Ile Cys Asn Ala Ala Ile Phe Pro Asp Lys
                325                 330                 335

Ala Pro Pro Gly Lys Ile Leu Phe Thr Val Phe Leu Gly Gly Ala Arg

```
                340             345             350
        Gln Glu Ser Leu Phe Asp Gln Met Thr Pro Glu Ala Leu Gln Gln
            355                 360                 365

Val Val Ser Glu Val Met Ser Leu Leu His Leu Ser Ala Pro Pro Val
            370                 375                 380

Met Gln His Phe Ser Ser Trp Asn Lys Ala Ile Pro Gln Leu Asn Val
        385                 390                 395                 400

Gly His Val Lys Leu Arg Arg Ala Val Glu Ala Phe Glu Lys Lys Tyr
                        405                 410                 415

Pro Gly Ile His Leu Ser Gly Asn Tyr Leu Gln Gly Val Ala Ile Pro
                        420                 425                 430

Ala Leu Leu Gln His Ala Ala Ala Leu Ala Ala Ser Leu Lys Lys Asn
                        435                 440                 445

<210> SEQ ID NO 3
<211> LENGTH: 470
<212> TYPE: PRT
<213> ORGANISM: Bacillus subtilis

<400> SEQUENCE: 3

Met Ser Asp Gly Lys Lys His Val Val Ile Gly Gly Gly Ile Thr
1               5                   10                  15

Gly Leu Ala Ala Ala Phe Tyr Met Glu Lys Glu Ile Lys Glu Lys Asn
                20                  25                  30

Leu Pro Leu Glu Leu Thr Leu Val Glu Ala Ser Pro Arg Val Gly Gly
            35                  40                  45

Lys Ile Gln Thr Val Lys Lys Asp Gly Tyr Ile Ile Glu Arg Gly Pro
    50                  55                  60

Asp Ser Phe Leu Glu Arg Lys Lys Ser Ala Pro Gln Leu Val Lys Asp
65                  70                  75                  80

Leu Gly Leu Glu His Leu Leu Val Asn Asn Ala Thr Gly Gln Ser Tyr
                85                  90                  95

Val Leu Val Asn Arg Thr Leu His Pro Met Pro Lys Gly Ala Val Met
                100                 105                 110

Gly Ile Pro Thr Lys Ile Ala Pro Phe Val Ser Thr Gly Leu Phe Ser
            115                 120                 125

Leu Ser Gly Lys Ala Arg Ala Ala Met Asp Phe Ile Leu Pro Ala Ser
130                 135                 140

Lys Thr Lys Asp Asp Gln Ser Leu Gly Glu Phe Phe Arg Arg Arg Val
145                 150                 155                 160

Gly Asp Glu Val Val Glu Asn Leu Ile Glu Pro Leu Leu Ser Gly Ile
                165                 170                 175

Tyr Ala Gly Asp Ile Asp Lys Leu Ser Leu Met Ser Thr Phe Pro Gln
            180                 185                 190

Phe Tyr Gln Thr Glu Gln Lys His Arg Ser Leu Ile Leu Gly Met Lys
        195                 200                 205

Lys Thr Arg Pro Gln Gly Ser Gly Gln Gln Leu Thr Ala Lys Lys Gln
    210                 215                 220

Gly Gln Phe Gln Thr Leu Ser Thr Gly Leu Gln Thr Leu Val Glu Glu
225                 230                 235                 240

Ile Glu Lys Gln Leu Lys Leu Thr Lys Val Tyr Lys Gly Thr Lys Val
                245                 250                 255

Thr Lys Leu Ser His Ser Gly Ser Gly Tyr Ser Leu Glu Leu Asp Asn
            260                 265                 270
```

Gly Val Thr Leu Asp Ala Asp Ser Val Ile Val Thr Ala Pro His Lys
            275                 280                 285

Ala Ala Ala Gly Met Leu Ser Glu Leu Pro Ala Ile Ser His Leu Lys
290                 295                 300

Asn Met His Ser Thr Ser Val Ala Asn Val Ala Leu Gly Phe Pro Glu
305                 310                 315                 320

Gly Ser Val Gln Met Glu His Glu Gly Thr Gly Phe Val Ile Ser Arg
                325                 330                 335

Asn Ser Asp Phe Ala Ile Thr Ala Cys Thr Trp Thr Asn Lys Lys Trp
            340                 345                 350

Pro His Ala Ala Pro Glu Gly Lys Thr Leu Leu Arg Ala Tyr Val Gly
            355                 360                 365

Lys Ala Gly Asp Glu Ser Ile Val Asp Leu Ser Asp Asn Asp Ile Ile
370                 375                 380

Asn Ile Val Leu Glu Asp Leu Lys Lys Val Met Asn Ile Asn Gly Glu
385                 390                 395                 400

Pro Glu Met Thr Cys Val Thr Arg Trp His Glu Ser Met Pro Gln Tyr
                405                 410                 415

His Val Gly His Lys Gln Arg Ile Lys Glu Leu Arg Glu Ala Leu Ala
            420                 425                 430

Ser Ala Tyr Pro Gly Val Tyr Met Thr Gly Ala Ser Phe Glu Gly Val
            435                 440                 445

Gly Ile Pro Asp Cys Ile Asp Gln Gly Lys Ala Ala Val Ser Asp Ala
            450                 455                 460

Leu Thr Tyr Leu Phe Ser
465                 470

<210> SEQ ID NO 4
<211> LENGTH: 470
<212> TYPE: PRT
<213> ORGANISM: Bacillus pumilus

<400> SEQUENCE: 4

Met His Asp Asn Gln Lys His Leu Val Ile Ile Gly Gly Gly Ile Thr
1               5                   10                  15

Gly Leu Ala Ala Ala Phe Tyr Leu Glu Lys Glu Val Glu Glu Lys Gly
            20                  25                  30

Leu Pro Ile Gln Ile Ser Leu Ile Glu Ala Ser Pro Arg Leu Gly Gly
        35                  40                  45

Lys Ile Gln Thr Leu Tyr Lys Asp Gly Tyr Ile Ile Glu Arg Gly Pro
50                  55                  60

Asp Ser Phe Leu Glu Arg Lys Val Ser Gly Pro Gln Leu Ala Lys Asp
65                  70                  75                  80

Val Gly Leu Ser Asp Gln Leu Val Asn Asn Glu Thr Gly Gln Ala Tyr
                85                  90                  95

Val Leu Val Asn Glu Lys Leu His Pro Met Pro Lys Gly Ala Val Met
            100                 105                 110

Gly Ile Pro Thr Gln Ile Ser Pro Phe Ile Thr Thr Gly Leu Phe Ser
            115                 120                 125

Val Ala Gly Lys Ala Arg Ala Ala Met Asp Phe Val Leu Pro Lys Ser
        130                 135                 140

Lys Gln Thr Glu Asp Gln Ser Leu Gly Glu Phe Phe Arg Arg Arg Val
145                 150                 155                 160

Gly Asp Glu Val Val Glu Asn Leu Ile Glu Pro Leu Leu Ser Gly Ile
                165                 170                 175

Tyr Ala Gly Asp Ile Asp Arg Leu Ser Leu Met Ser Thr Phe Pro Gln
            180                 185                 190

Phe Tyr Gln Thr Glu Gln Gln His Arg Ser Leu Ile Leu Gly Met Lys
        195                 200                 205

Lys Ser Gln Gln His Ala Lys Ala Gln Gln Val Thr Ala Lys Lys Gln
210                 215                 220

Gly Gln Phe Gln Thr Ile Asn Gln Gly Leu Gln Ser Leu Val Glu Ala
225                 230                 235                 240

Val Glu Gly Lys Leu Lys Leu Thr Thr Val Tyr Lys Gly Thr Lys Val
                245                 250                 255

Lys Gln Ile Glu Lys Thr Asp Gly Gly Tyr Gly Leu Gln Leu Asp Ser
            260                 265                 270

Gly Gln Thr Leu Phe Ala Asp Ser Ala Ile Val Thr Thr Pro His Gln
        275                 280                 285

Ser Ile Tyr Ser Met Phe Pro Lys Glu Ala Gly Leu Glu Tyr Leu His
    290                 295                 300

Asp Met Thr Ser Thr Ser Val Ala Thr Val Ala Leu Gly Phe Lys Asp
305                 310                 315                 320

Glu Asp Val His Asn Glu Tyr Asp Gly Thr Gly Phe Val Ile Ser Arg
                325                 330                 335

Asn Ser Asp Phe Ser Ile Thr Ala Cys Thr Trp Thr Asn Lys Lys Trp
            340                 345                 350

Pro His Thr Ala Pro Lys Gly Lys Thr Leu Leu Arg Ala Tyr Val Gly
        355                 360                 365

Lys Ala Gly Asp Glu Ser Ile Val Glu Gln Ser Asp Ser Gln Ile Val
370                 375                 380

Ser Ile Val Leu Glu Asp Leu Lys Lys Ile Met Asp Ile Lys Ala Asp
385                 390                 395                 400

Pro Glu Leu Thr Thr Val Thr Arg Trp Lys Thr Ser Met Pro Gln Tyr
                405                 410                 415

His Val Gly His Gln Lys Ala Ile Ser Asn Met Arg Glu Thr Phe Lys
            420                 425                 430

Gln Ser Tyr Pro Gly Val Tyr Ile Thr Gly Ala Ala Phe Glu Gly Val
        435                 440                 445

Gly Ile Pro Asp Cys Ile Asp Gln Gly Lys Ala Ala Ile Ser Glu Ala
    450                 455                 460

Val Ser Tyr Leu Phe Ser
465                 470

<210> SEQ ID NO 5
<211> LENGTH: 470
<212> TYPE: PRT
<213> ORGANISM: Bacillus pumilus

<400> SEQUENCE: 5

Met His Asp Asn Gln Lys His Leu Val Ile Ile Gly Gly Gly Ile Thr
1               5                   10                  15

Gly Leu Ala Ala Ala Phe Tyr Leu Glu Lys Glu Val Glu Glu Lys Gly
                20                  25                  30

Leu Pro Ile Gln Ile Ser Leu Ile Glu Ala Ser Pro Arg Leu Gly Gly
            35                  40                  45

Lys Ile Gln Thr Leu Tyr Lys Asp Gly Tyr Ile Glu Arg Gly Pro
        50                  55                  60

Asp Ser Phe Leu Glu Arg Lys Val Ser Gly Pro Gln Leu Ala Lys Asp

```
            65                  70                  75                  80
        Val Gly Leu Ser Asp Gln Leu Val Asn Asn Glu Thr Gly Gln Ala Tyr
                        85                  90                  95

Val Leu Val Asn Glu Thr Leu His Pro Met Pro Lys Gly Ala Val Met
                        100                 105                 110

Gly Ile Pro Thr Gln Ile Ser Pro Phe Ile Thr Thr Gly Leu Phe Ser
                        115                 120                 125

Val Ala Gly Lys Ala Arg Ala Ala Met Asp Phe Val Leu Pro Lys Ser
        130                 135                 140

Lys Gln Thr Glu Asp Gln Ser Leu Gly Glu Phe Phe Arg Arg Arg Val
        145                 150                 155                 160

Gly Asp Glu Val Val Glu Asn Leu Ile Glu Pro Leu Leu Ser Gly Ile
                        165                 170                 175

Tyr Ala Gly Asp Ile Asp Arg Leu Ser Leu Met Ser Thr Phe Pro Gln
                        180                 185                 190

Phe Tyr Gln Thr Glu Gln Lys His Arg Ser Leu Ile Leu Gly Met Lys
                        195                 200                 205

Lys Ser Gln Gln His Ala Lys Ala Gln Val Thr Ala Lys Lys Gln
        210                 215                 220

Gly Gln Phe Gln Thr Ile Asn Gln Gly Leu Gln Ala Leu Val Glu Ala
        225                 230                 235                 240

Val Glu Ser Lys Leu Lys Leu Thr Thr Ile Tyr Lys Gly Thr Lys Val
                        245                 250                 255

Lys Gln Ile Glu Lys Thr Asp Gly Gly Tyr Gly Val Gln Leu Asp Ser
                        260                 265                 270

Gly Gln Thr Leu Leu Ala Asp Ser Ala Ile Val Thr Thr Pro His Gln
                        275                 280                 285

Ser Ile Tyr Ser Met Phe Pro Lys Glu Ala Gly Leu Glu Tyr Leu His
                        290                 295                 300

Asp Met Thr Ser Thr Ser Val Ala Thr Val Ala Leu Gly Phe Lys Glu
        305                 310                 315                 320

Glu Asp Val His Asn Glu Tyr Asp Gly Thr Gly Phe Val Ile Ser Arg
                        325                 330                 335

Asn Ser Asp Phe Ser Ile Thr Ala Cys Thr Trp Thr Asn Lys Lys Trp
                        340                 345                 350

Pro His Thr Ala Pro Lys Gly Lys Thr Leu Leu Arg Ala Tyr Val Gly
                        355                 360                 365

Lys Ala Gly Asp Glu Ser Ile Val Glu Gln Ser Asp His Gln Ile Val
                        370                 375                 380

Ser Ile Val Leu Glu Asp Leu Lys Lys Ile Met Asp Ile Lys Ala Asp
        385                 390                 395                 400

Pro Glu Leu Thr Thr Val Thr Arg Trp Lys Thr Ser Met Pro Gln Tyr
                        405                 410                 415

His Val Gly His Gln Lys Ala Ile Ser Asn Met Arg Glu Thr Phe Lys
                        420                 425                 430

Gln Ser Tyr Pro Gly Val Tyr Ile Thr Gly Ala Ala Phe Glu Gly Val
                        435                 440                 445

Gly Ile Pro Asp Cys Ile Asp Gln Gly Lys Ala Ala Ile Ser Glu Ala
                        450                 455                 460

Val Ser Tyr Leu Phe Ser
        465                 470

<210> SEQ ID NO 6
```

-continued

<211> LENGTH: 439
<212> TYPE: PRT
<213> ORGANISM: Xanthomonas campestris

<400> SEQUENCE: 6

Gln Pro Val Ile Ile Ala Gly Ala Gly Ile Ala Gly Leu Ser Ile Ala
1               5                   10                  15

Tyr Glu Leu Gln Gln Lys Gly Ile Pro Tyr Glu Ile Met Glu Ala Ser
            20                  25                  30

Ser Tyr Ala Gly Gly Val Val Lys Ser Leu His Ile Asp Gly Tyr Glu
        35                  40                  45

Leu Asp Ala Gly Pro Asn Ser Leu Ala Ala Ser Ala Ala Phe Met Ala
    50                  55                  60

Tyr Ile Asp Gln Leu Gly Leu Gln Asp Gln Val Leu Glu Ala Ala Ala
65                  70                  75                  80

Ala Ser Lys Asn Arg Phe Leu Val Arg Asn Asp Lys Leu His Ala Val
                85                  90                  95

Ser Pro His Pro Phe Lys Ile Leu Gln Ser Ala Tyr Ile Ser Gly Gly
            100                 105                 110

Ala Lys Trp Arg Leu Phe Thr Glu Arg Phe Arg Lys Ala Ala Ala Pro
        115                 120                 125

Glu Gly Glu Glu Thr Val Ser Ser Phe Val Thr Arg Arg Phe Gly Lys
    130                 135                 140

Glu Ile Asn Asp Tyr Leu Phe Glu Pro Val Leu Ser Gly Ile Tyr Ala
145                 150                 155                 160

Gly Asn Pro Asp Leu Met Ser Val Gly Glu Val Leu Pro Met Leu Pro
                165                 170                 175

Gln Trp Glu Gln Lys Tyr Gly Ser Val Thr Gln Gly Leu Leu Lys Asn
            180                 185                 190

Lys Gly Ala Met Gly Gly Arg Lys Ile Ile Ala Phe Lys Gly Gly Asn
        195                 200                 205

Ala Thr Leu Thr Asn Arg Leu Gln Ser Leu Leu Ser Gly Lys Ile Arg
    210                 215                 220

Phe Asn Cys Ala Val Thr Gly Val Thr Arg Gly Ala Asp Asp Tyr Ile
225                 230                 235                 240

Val Gln Tyr Thr Glu Asn Gly Asn Thr Ala Met Leu Asn Ala Ser Arg
                245                 250                 255

Val Ile Phe Thr Thr Pro Ala Tyr Ser Thr Ala Val Ala Ile Gln Ala
            260                 265                 270

Leu Asp Ala Ser Leu Ala Thr His Leu Ser Asp Val Pro Tyr Pro Arg
        275                 280                 285

Met Gly Val Leu His Leu Gly Phe Gly Ala Glu Ala Arg Gln Lys Ala
    290                 295                 300

Pro Ala Gly Phe Gly Phe Leu Val Pro His Ala Ala Gly Lys His Phe
305                 310                 315                 320

Leu Gly Ala Ile Cys Asn Ser Ala Ile Phe Pro Ser Arg Val Pro Thr
                325                 330                 335

Gly Lys Val Leu Phe Thr Val Phe Leu Gly Gly Ala Arg Gln Glu Gln
            340                 345                 350

Leu Phe Asp Gln Leu Gly Pro Glu Lys Leu Gln Gln Thr Val Val Lys
        355                 360                 365

Glu Leu Met Glu Leu Leu Gly Leu Thr Thr Pro Pro Glu Met Gln Arg
    370                 375                 380

Phe Ser Glu Trp Asn Arg Ala Ile Pro Gln Leu Asn Val Gly Tyr Ala

```
             385                 390                 395                 400
    Gln Thr Arg Gln Gln Ile Gly Val Phe Glu Gln Arg Tyr Pro Gly Ile
                    405                 410                 415

Arg Leu Ala Gly Asn Tyr Val Thr Gly Val Ala Val Pro Ala Ile Ile
                    420                 425                 430

Gln Ala Ala Lys Gly Tyr Cys
                    435

<210> SEQ ID NO 7
<211> LENGTH: 445
<212> TYPE: PRT
<213> ORGANISM: Chitinophaga pinensis

<400> SEQUENCE: 7

Gln Pro Val Leu Ile Val Gly Ala Gly Leu Ser Gly Leu Ser Ile Ala
    1               5                   10                  15

Tyr Glu Leu Gln Lys Leu Gln Val Pro Tyr Gln Val Leu Glu Val Ser
                    20                  25                  30

Gly His Ser Gly Gly Val Met Lys Ser Leu Arg Lys Asp Gly Phe Glu
                    35                  40                  45

Leu Asp Ala Gly Ala Asn Thr Ile Ala Ala Ser Pro Glu Ile Leu Ala
                50                  55                  60

Tyr Phe Thr Ser Leu Gly Leu Glu Asn Glu Ile Leu Gln Ala Thr Ala
    65                  70                  75                  80

Ala Ser Lys His Arg Phe Leu Val Arg Arg Gln Leu His Ala Val
                    85                  90                  95

Ser Pro His Pro Phe Lys Ile Met Ser Ser Pro Tyr Leu Ser Arg Gly
                    100                 105                 110

Ser Lys Trp Arg Leu Phe Thr Glu Arg Phe Arg Lys Pro Val Val Ala
                    115                 120                 125

Ser Gly Glu Glu Thr Val Thr Asp Phe Ile Thr Arg Arg Phe Asn Arg
                130                 135                 140

Glu Ile Ala Glu Tyr Val Phe Asp Pro Val Leu Ser Gly Ile Tyr Ala
    145                 150                 155                 160

Gly Asn Pro Asp Gln Met Ser Ile Ala Glu Val Leu Pro Ala Leu Pro
                    165                 170                 175

Arg Trp Glu Arg Glu Tyr Gly Ser Val Thr Lys Gly Leu Met Lys Asp
                    180                 185                 190

Lys Gly Ala Met Gly Gly Arg Lys Ile Ile Ser Phe Lys Gly Gly Asn
                    195                 200                 205

Gln Leu Leu Thr Asn Arg Leu Gln Gln Leu Leu Thr Thr Pro Val Arg
                    210                 215                 220

Phe Asn Cys Lys Val Thr Gly Ile Thr Ala Ser Asn Gly Gly Tyr Ile
    225                 230                 235                 240

Val Ser Ala Val Glu Asp Gly Val Ser Glu Ser Tyr Thr Ala Ser Arg
                    245                 250                 255

Val Ile Leu Thr Thr Pro Ala Tyr Ser Ala Ala Ala Thr Ile Thr Asn
                    260                 265                 270

Leu Asp Ala Ala Thr Ala Ala Leu Leu Asn Glu Ile His Tyr Pro Arg
                    275                 280                 285

Met Gly Val Leu His Leu Gly Phe Asp Ala Thr Ala Leu Pro Gln Pro
                    290                 295                 300

Leu Asp Gly Phe Gly Phe Leu Val Pro Asn Ala Glu Asn Met His Phe
    305                 310                 315                 320
```

-continued

```
Leu Gly Ala Ile Cys Asn Ala Ala Ile Phe Pro Asp Lys Ala Pro Pro
                325                 330                 335

Gly Lys Ile Leu Phe Thr Val Phe Leu Gly Gly Ala Arg Gln Glu Ser
            340                 345                 350

Leu Phe Asp Gln Met Thr Pro Glu Ala Leu Gln Gln Gln Val Val Ser
        355                 360                 365

Glu Val Met Ser Leu Leu His Leu Ser Ala Pro Pro Val Met Gln His
370                 375                 380

Phe Ser Ser Trp Asn Lys Ala Ile Pro Gln Leu Asn Val Gly His Val
385                 390                 395                 400

Lys Leu Arg Arg Ala Val Glu Ala Phe Glu Lys Lys Tyr Pro Gly Ile
                405                 410                 415

His Leu Ser Gly Asn Tyr Leu Gln Gly Val Ala Ile Pro Ala Leu Leu
            420                 425                 430

Gln His Ala Ala Ala Leu Ala Ala Ser Leu Lys Lys Asn
        435                 440                 445

<210> SEQ ID NO 8
<211> LENGTH: 448
<212> TYPE: PRT
<213> ORGANISM: Artificial Sequence
<220> FEATURE:
<223> OTHER INFORMATION: Recombinant

<400> SEQUENCE: 8

Met Ser Asp Gln Pro Val Leu Ile Val Gly Ala Gly Leu Ser Gly Leu
1               5                   10                  15

Ser Ile Ala Tyr Glu Leu Gln Lys Leu Gln Val Pro Tyr Gln Val Leu
            20                  25                  30

Glu Val Ser Gly His Ser Gly Gly Val Met Lys Ser Leu Arg Lys Asp
        35                  40                  45

Gly Phe Glu Leu Asp Ala Gly Ala Asn Thr Ile Ala Thr Ser Pro Glu
    50                  55                  60

Ile Leu Ala Tyr Phe Thr Ser Leu Gly Leu Glu Asn Glu Ile Leu Gln
65                  70                  75                  80

Ala Thr Ala Thr Ser Lys His Arg Phe Leu Val Arg Arg Arg Gln Leu
                85                  90                  95

His Ala Val Ser Pro His Pro Phe Lys Ile Met Ser Ser Pro Tyr Leu
            100                 105                 110

Cys Arg Gly Ser Lys Trp Arg Leu Phe Thr Glu Arg Phe Arg Lys Pro
        115                 120                 125

Val Val Ala Ser Gly Glu Glu Thr Val Thr Asp Phe Ile Thr Arg Arg
    130                 135                 140

Phe Asn Arg Glu Ile Ala Glu Tyr Val Phe Asp Pro Val Leu Ser Gly
145                 150                 155                 160

Ile Tyr Ala Gly Asn Pro Asp Gln Met Ser Ile Ala Glu Val Leu Pro
                165                 170                 175

Ala Leu Pro Arg Trp Glu Arg Glu Tyr Gly Ser Val Thr Lys Gly Leu
            180                 185                 190

Met Lys Asp Lys Gly Ala Met Gly Gly Arg Lys Ile Ile Ser Phe Lys
        195                 200                 205

Gly Gly Asn Gln Leu Leu Thr Asn Arg Leu Gln Gln Leu Leu Thr Thr
    210                 215                 220

Pro Val Arg Phe Asn Cys Lys Val Thr Gly Ile Thr Ala Ser Asn Gly
225                 230                 235                 240
```

Gly Tyr Ile Val Ser Ala Val Glu Asp Gly Val Ser Glu Ser Tyr Thr
                245                 250                 255

Ala Ser Arg Val Ile Leu Thr Thr Pro Ala Tyr Ser Ala Ala Ala Thr
            260                 265                 270

Ile Thr Asn Leu Asp Ala Ala Thr Ala Ala Leu Leu Asn Glu Ile His
        275                 280                 285

Tyr Pro Arg Met Gly Val Leu His Leu Gly Phe Asp Ala Thr Ala Leu
    290                 295                 300

Pro Gln Pro Leu Asp Gly Phe Gly Phe Leu Val Pro Asn Ala Glu Asn
305                 310                 315                 320

Met His Phe Leu Gly Ala Ile Cys Asn Ala Ala Ile Phe Pro Asp Lys
                325                 330                 335

Ala Pro Pro Gly Lys Ile Leu Phe Thr Val Phe Leu Gly Gly Ala Arg
            340                 345                 350

Gln Glu Ser Leu Phe Asp Gln Met Thr Pro Glu Ala Leu Gln Gln Gln
        355                 360                 365

Val Val Ser Glu Val Met Ser Leu Leu His Leu Ser Ala Pro Pro Val
    370                 375                 380

Met Gln His Phe Ser Ser Trp Asn Lys Ala Ile Pro Gln Leu Asn Val
385                 390                 395                 400

Gly His Val Lys Leu Arg Arg Ala Val Glu Ala Phe Glu Lys Lys Tyr
                405                 410                 415

Pro Gly Ile His Leu Ser Gly Asn Tyr Leu Gln Gly Val Ala Ile Pro
            420                 425                 430

Ala Leu Leu Gln His Ala Ala Leu Ala Ala Ser Leu Lys Lys Asn
        435                 440                 445

<210> SEQ ID NO 9
<211> LENGTH: 445
<212> TYPE: PRT
<213> ORGANISM: Artificial Sequence
<220> FEATURE:
<223> OTHER INFORMATION: Recombinant

<400> SEQUENCE: 9

Gln Pro Val Leu Ile Val Gly Ala Gly Leu Ser Gly Leu Ser Ile Ala
1               5                   10                  15

Tyr Glu Leu Gln Lys Leu Gln Val Pro Tyr Gln Val Leu Glu Val Ser
                20                  25                  30

Gly His Ser Gly Gly Val Met Lys Ser Leu Arg Lys Asp Gly Phe Glu
            35                  40                  45

Leu Asp Ala Gly Ala Asn Thr Ile Ala Thr Ser Pro Glu Ile Leu Ala
    50                  55                  60

Tyr Phe Thr Ser Leu Gly Leu Glu Asn Glu Ile Leu Gln Ala Thr Ala
65                  70                  75                  80

Thr Ser Lys His Arg Phe Leu Val Arg Arg Gln Leu His Ala Val
                85                  90                  95

Ser Pro His Pro Phe Lys Ile Met Ser Ser Pro Tyr Leu Cys Arg Gly
            100                 105                 110

Ser Lys Trp Arg Leu Phe Thr Glu Arg Phe Arg Lys Pro Val Val Ala
        115                 120                 125

Ser Gly Glu Glu Thr Val Thr Asp Phe Ile Thr Arg Arg Phe Asn Arg
    130                 135                 140

Glu Ile Ala Glu Tyr Val Phe Asp Pro Val Leu Ser Gly Ile Tyr Ala
145                 150                 155                 160

Gly Asn Pro Asp Gln Met Ser Ile Ala Glu Val Leu Pro Ala Leu Pro
            165                 170                 175

Arg Trp Glu Arg Glu Tyr Gly Ser Val Thr Lys Gly Leu Met Lys Asp
        180                 185                 190

Lys Gly Ala Met Gly Gly Arg Lys Ile Ile Ser Phe Lys Gly Gly Asn
    195                 200                 205

Gln Leu Leu Thr Asn Arg Leu Gln Gln Leu Leu Thr Thr Pro Val Arg
210                 215                 220

Phe Asn Cys Lys Val Thr Gly Ile Thr Ala Ser Asn Gly Gly Tyr Ile
225                 230                 235                 240

Val Ser Ala Val Glu Asp Gly Val Ser Glu Ser Tyr Thr Ala Ser Arg
                245                 250                 255

Val Ile Leu Thr Thr Pro Ala Tyr Ser Ala Ala Thr Ile Thr Asn
            260                 265                 270

Leu Asp Ala Ala Thr Ala Ala Leu Leu Asn Glu Ile His Tyr Pro Arg
        275                 280                 285

Met Gly Val Leu His Leu Gly Phe Asp Ala Thr Ala Leu Pro Gln Pro
    290                 295                 300

Leu Asp Gly Phe Gly Phe Leu Val Pro Asn Ala Glu Asn Met His Phe
305                 310                 315                 320

Leu Gly Ala Ile Cys Asn Ala Ala Ile Phe Pro Asp Lys Ala Pro Pro
                325                 330                 335

Gly Lys Ile Leu Phe Thr Val Phe Leu Gly Gly Ala Arg Gln Glu Ser
            340                 345                 350

Leu Phe Asp Gln Met Thr Pro Glu Ala Leu Gln Gln Val Val Ser
        355                 360                 365

Glu Val Met Ser Leu Leu His Leu Ser Ala Pro Pro Val Met Gln His
370                 375                 380

Phe Ser Ser Trp Asn Lys Ala Ile Pro Gln Leu Asn Val Gly His Val
385                 390                 395                 400

Lys Leu Arg Arg Ala Val Glu Ala Phe Glu Lys Lys Tyr Pro Gly Ile
                405                 410                 415

His Leu Ser Gly Asn Tyr Leu Gln Gly Val Ala Ile Pro Ala Leu Leu
            420                 425                 430

Gln His Ala Ala Ala Leu Ala Ala Ser Leu Lys Lys Asn
        435                 440                 445

<210> SEQ ID NO 10
<211> LENGTH: 445
<212> TYPE: PRT
<213> ORGANISM: Artificial Sequence
<220> FEATURE:
<223> OTHER INFORMATION: Recombinant

<400> SEQUENCE: 10

Gln Pro Val Leu Ile Val Gly Ala Gly Leu Ser Gly Leu Ser Ile Ala
1               5                   10                  15

Tyr Glu Leu Gln Lys Leu Gln Val Pro Tyr Gln Val Leu Glu Val Ser
            20                  25                  30

Gly His Ser Gly Gly Val Met Lys Ser Leu Arg Lys Asp Gly Phe Glu
        35                  40                  45

Leu Asp Ala Gly Ala Asn Thr Ile Ala Thr Ser Pro Glu Ile Leu Ala
    50                  55                  60

Tyr Phe Thr Ser Leu Gly Leu Glu Asn Glu Ile Leu Gln Ala Thr Ala
65                  70                  75                  80

```
Ala Ser Lys His Arg Phe Leu Val Arg Arg Gln Leu His Ala Val
             85                  90                  95

Ser Pro His Pro Phe Lys Ile Met Ser Ser Pro Tyr Leu Ser Arg Gly
        100                 105                 110

Ser Lys Trp Arg Leu Phe Thr Glu Arg Phe Lys Pro Val Val Ala
        115                 120                 125

Ser Gly Glu Glu Thr Val Thr Asp Phe Ile Thr Arg Arg Phe Asn Arg
        130                 135                 140

Glu Ile Ala Glu Tyr Val Phe Asp Pro Val Leu Ser Gly Ile Tyr Ala
145                 150                 155                 160

Gly Asn Pro Asp Gln Met Ser Ile Ala Glu Val Leu Pro Ala Leu Pro
                165                 170                 175

Arg Trp Glu Arg Glu Tyr Gly Ser Val Thr Lys Gly Leu Met Lys Asp
            180                 185                 190

Lys Gly Ala Met Gly Gly Arg Lys Ile Ile Ser Phe Lys Gly Gly Asn
            195                 200                 205

Gln Leu Leu Thr Asn Arg Leu Gln Gln Leu Leu Thr Thr Pro Val Arg
    210                 215                 220

Phe Asn Cys Lys Val Thr Gly Ile Thr Ala Ser Asn Gly Gly Tyr Ile
225                 230                 235                 240

Val Ser Ala Val Glu Asp Gly Val Ser Glu Ser Tyr Thr Ala Ser Arg
                245                 250                 255

Val Ile Leu Thr Thr Pro Ala Tyr Ser Ala Ala Thr Ile Thr Asn
                260                 265                 270

Leu Asp Ala Ala Thr Ala Ala Leu Leu Asn Glu Ile His Tyr Pro Arg
    275                 280                 285

Met Gly Val Leu His Leu Gly Phe Asp Ala Thr Ala Leu Pro Gln Pro
290                 295                 300

Leu Asp Gly Phe Gly Phe Leu Val Pro Asn Ala Glu Asn Met His Phe
305                 310                 315                 320

Leu Gly Ala Ile Cys Asn Ala Ala Ile Phe Pro Asp Lys Ala Pro Pro
                325                 330                 335

Gly Lys Ile Leu Phe Thr Val Phe Leu Gly Gly Ala Arg Gln Glu Ser
            340                 345                 350

Leu Phe Asp Gln Met Thr Pro Glu Ala Leu Gln Gln Gln Val Val Ser
    355                 360                 365

Glu Val Met Ser Leu Leu His Leu Ser Ala Pro Pro Val Met Gln His
        370                 375                 380

Phe Ser Ser Trp Asn Lys Ala Ile Pro Gln Leu Asn Val Gly His Val
385                 390                 395                 400

Lys Leu Arg Arg Ala Val Glu Ala Phe Glu Lys Lys Tyr Pro Gly Ile
                405                 410                 415

His Leu Ser Gly Asn Tyr Leu Gln Gly Val Ala Ile Pro Ala Leu Leu
                420                 425                 430

Gln His Ala Ala Ala Leu Ala Ala Ser Leu Lys Lys Asn
        435                 440                 445

<210> SEQ ID NO 11
<211> LENGTH: 445
<212> TYPE: PRT
<213> ORGANISM: Artificial Sequence
<220> FEATURE:
<223> OTHER INFORMATION: Recombinant

<400> SEQUENCE: 11
```

```
Gln Pro Val Leu Ile Val Gly Ala Gly Leu Ser Gly Leu Ser Ile Ala
  1               5                  10                 15

Tyr Glu Leu Gln Lys Leu Gln Val Pro Tyr Gln Val Leu Glu Val Ser
             20                  25                 30

Gly His Ser Gly Gly Val Met Lys Ser Leu Arg Lys Asp Gly Phe Glu
             35                  40                 45

Leu Asp Ala Gly Ala Asn Thr Ile Ala Thr Ser Pro Glu Ile Leu Ala
 50                  55                  60

Tyr Phe Thr Ser Leu Gly Leu Glu Asn Glu Ile Leu Gln Ala Thr Ala
 65                  70                  75                 80

Thr Ser Lys His Arg Phe Leu Val Arg Arg Gln Leu His Ala Val
                 85                  90                 95

Ser Pro His Pro Phe Lys Ile Met Ser Ser Pro Tyr Leu Cys Arg Gly
             100                 105                110

Ser Lys Trp Arg Leu Phe Thr Glu Arg Phe Lys Pro Val Val Ala
             115                 120                 125

Ser Gly Glu Glu Thr Val Thr Asp Phe Ile Thr Arg Arg Phe Asn Arg
    130                 135                 140

Glu Ile Ala Glu Tyr Val Phe Asp Pro Val Leu Ser Gly Ile Tyr Ala
145                 150                 155                 160

Gly Asn Pro Asp Gln Met Ser Ile Ala Glu Val Leu Pro Ala Leu Pro
                165                 170                 175

Arg Trp Glu Arg Glu Tyr Gly Ser Val Thr Lys Gly Leu Met Lys Asp
            180                 185                 190

Lys Gly Ala Met Gly Gly Arg Lys Ile Ile Ser Phe Lys Gly Gly Asn
            195                 200                 205

Gln Leu Leu Thr Asn Arg Leu Gln Gln Leu Leu Thr Thr Pro Val Arg
    210                 215                 220

Phe Asn Cys Lys Val Thr Gly Ile Thr Ala Ser Asn Gly Gly Tyr Ile
225                 230                 235                 240

Val Ser Ala Val Glu Asp Gly Val Ser Glu Ser Tyr Thr Ala Ser Arg
                245                 250                 255

Val Ile Leu Thr Thr Pro Ala Tyr Ser Ala Ala Thr Ile Thr Asn
            260                 265                 270

Leu Asp Ala Ala Thr Ala Ala Leu Leu Asn Glu Ile His Tyr Pro Arg
    275                 280                 285

Met Gly Val Leu His Leu Gly Phe Asp Ala Thr Ala Leu Pro Gln Pro
290                 295                 300

Leu Asp Gly Phe Gly Phe Leu Val Pro Asn Ala Glu Asn Met His Phe
305                 310                 315                 320

Leu Gly Ala Ile Cys Asn Ala Ala Ile Phe Pro Asp Lys Ala Pro Pro
                325                 330                 335

Gly Lys Ile Leu Phe Thr Val Phe Leu Gly Gly Ala Arg Gln Glu Ser
            340                 345                 350

Leu Phe Asp Gln Met Thr Pro Glu Ala Leu Gln Gln Val Val Ser
            355                 360                 365

Glu Val Met Ser Leu Leu His Leu Ser Ala Pro Pro Val Met Gln His
    370                 375                 380

Phe Ser Ser Trp Asn Lys Ala Ile Pro Gln Leu Asn Val Gly His Val
385                 390                 395                 400

Lys Leu Arg Arg Ala Val Glu Ala Phe Glu Lys Lys Tyr Pro Gly Ile
                405                 410                 415

His Leu Ser Gly Asn Tyr Leu Gln Gly Val Ala Ile Thr Ala Leu Leu
```

```
              420                 425                 430
Gln His Ala Ala Leu Ala Ala Ser Leu Lys Lys Asn
        435                 440                 445

<210> SEQ ID NO 12
<211> LENGTH: 445
<212> TYPE: PRT
<213> ORGANISM: Artificial Sequence
<220> FEATURE:
<223> OTHER INFORMATION: Recombinant

<400> SEQUENCE: 12

Gln Pro Val Leu Ile Val Gly Ala Gly Leu Ser Gly Leu Ser Ile Ala
1               5                   10                  15

Tyr Glu Leu Gln Lys Leu Gln Val Pro Tyr Gln Val Leu Glu Val Ser
            20                  25                  30

Gly His Ser Gly Gly Val Met Lys Ser Leu Arg Lys Asp Gly Phe Glu
        35                  40                  45

Leu Asp Ala Gly Ala Asn Thr Ile Ala Thr Ser Pro Glu Ile Leu Ala
    50                  55                  60

Tyr Phe Thr Ser Leu Gly Leu Glu Asn Glu Ile Leu Gln Ala Thr Ala
65                  70                  75                  80

Thr Ser Lys His Arg Phe Leu Val Arg Arg Gln Leu His Ala Val
            85                  90                  95

Ser Pro His Pro Phe Lys Ile Met Ser Ser Pro Tyr Leu Cys Arg Gly
            100                 105                 110

Ser Lys Trp Arg Leu Phe Thr Glu Arg Phe Arg Lys Pro Val Val Ala
        115                 120                 125

Ser Gly Glu Glu Thr Val Thr Asp Phe Ile Thr Arg Arg Phe Asn Arg
    130                 135                 140

Glu Ile Ala Glu Tyr Val Phe Asp Pro Val Leu Ser Gly Ile Tyr Ala
145                 150                 155                 160

Gly Asn Pro Asp Gln Met Ser Ile Ala Glu Val Leu Pro Ala Leu Pro
                165                 170                 175

Arg Trp Glu Arg Glu Tyr Gly Ser Val Thr Lys Gly Leu Met Lys Asp
            180                 185                 190

Lys Gly Ala Met Gly Gly Arg Lys Ile Ile Ser Phe Lys Gly Gly Asn
        195                 200                 205

Gln Leu Leu Thr Asn Arg Leu Gln Gln Leu Leu Thr Thr Pro Val Arg
    210                 215                 220

Phe Asn Tyr Lys Val Thr Gly Ile Thr Ala Ser Asn Gly Gly Tyr Ile
225                 230                 235                 240

Val Ser Ala Val Glu Asp Gly Val Ser Glu Ser Tyr Thr Ala Ser Arg
                245                 250                 255

Val Ile Leu Thr Thr Pro Ala Tyr Ser Ala Ala Thr Ile Thr Asn
            260                 265                 270

Leu Asp Ala Ala Thr Ala Ala Leu Leu Asn Glu Ile His Tyr Pro Arg
        275                 280                 285

Met Gly Val Leu His Leu Gly Phe Asp Ala Thr Ala Leu Pro Gln Pro
    290                 295                 300

Leu Asp Gly Phe Gly Phe Leu Val Pro Asn Ala Glu Asn Met His Phe
305                 310                 315                 320

Leu Gly Ala Ile Cys Asn Ala Ala Ile Phe Pro Asp Lys Ala Pro Pro
                325                 330                 335

Gly Lys Ile Leu Phe Thr Val Phe Leu Gly Gly Ala Arg Gln Glu Ser
```

```
                340             345                350
Leu Phe Asp Gln Met Thr Pro Glu Ala Leu Gln Gln Gln Val Val Ser
            355                 360                 365

Glu Val Met Ser Leu Leu His Leu Ser Ala Pro Pro Val Met Gln His
        370                 375                 380

Phe Ser Ser Trp Asn Lys Ala Ile Pro Gln Leu Asn Val Gly His Val
385                 390                 395                 400

Lys Leu Arg Arg Ala Val Glu Ala Phe Glu Lys Lys Tyr Pro Gly Ile
                405                 410                 415

His Leu Ser Gly Asn Tyr Leu Gln Gly Val Ala Ile Pro Ala Leu Leu
            420                 425                 430

Gln His Ala Ala Ala Leu Ala Ala Ser Leu Lys Lys Asn
        435                 440                 445

<210> SEQ ID NO 13
<211> LENGTH: 477
<212> TYPE: PRT
<213> ORGANISM: Paenibacillus macerans

<400> SEQUENCE: 13

Met Ser Lys Lys Ile Ala Val Ile Gly Gly Gly Ile Thr Gly Leu Ser
1               5                   10                  15

Val Ala Tyr Tyr Val Arg Lys Leu Leu Arg Glu Gln Gly Val Asn Ala
                20                  25                  30

Gly Val Thr Leu Val Glu Gln Ser Asp Arg Leu Gly Gly Lys Ile Arg
            35                  40                  45

Ser Leu Arg Arg Asp Gly Phe Thr Ile Glu Gln Gly Pro Asp Ser Met
    50                  55                  60

Ile Ala Arg Lys Pro Ala Ala Leu Glu Leu Ile Arg Glu Leu Gly Leu
65                  70                  75                  80

Glu Asp Lys Leu Ala Gly Thr Asn Pro Gln Ala Lys Arg Ser Tyr Ile
                85                  90                  95

Leu His Arg Gly Lys Phe His Pro Met Pro Pro Gly Leu Met Leu Gly
            100                 105                 110

Ile Pro Thr Gln Met Trp Pro Met Val Lys Thr Gly Leu Leu Ser Pro
        115                 120                 125

Ala Gly Lys Leu Arg Ala Ala Met Asp Leu Leu Leu Pro Ala Arg Arg
130                 135                 140

Gly Gly Gly Asp Glu Ser Leu Gly Gly Phe Ile Arg Arg Arg Leu Gly
145                 150                 155                 160

Arg Glu Val Leu Glu Gln Met Thr Glu Pro Leu Leu Ala Gly Ile Tyr
                165                 170                 175

Ala Gly Asp Thr Glu Gln Leu Ser Leu Lys Ala Thr Phe Pro Gln Phe
            180                 185                 190

Met Glu Met Glu Arg Lys His Arg Ser Leu Ile Leu Gly Leu Leu Ala
        195                 200                 205

Gly Lys Lys Gln Pro Pro Arg Pro Gly Gly Ser Gln Val Pro Leu Pro
    210                 215                 220

Lys Ala Ala Gln Thr Ser Met Phe Leu Thr Leu Thr Gly Gly Leu Glu
225                 230                 235                 240

Gly Leu Thr Glu Ala Leu Glu Glu Ser Leu Ser Glu Glu Lys Ile Ile
                245                 250                 255

Thr Gly Gln Ala Val Thr Gly Leu Ser Gln Gln Glu Ala Gly Tyr Glu
            260                 265                 270
```

```
Leu Asn Leu Ser Gly Gly Glu Arg Leu Asn Ala Asp Gly Val Ile Leu
            275                 280                 285

Ala Val Pro Ala Phe Ala Ala Arg Leu Leu Asp Gly Val Pro Glu
    290                 295                 300

Ala Ala Tyr Leu Glu Arg Ile Arg Tyr Val Ser Val Ala Asn Leu Ala
305                 310                 315                 320

Phe Ala Tyr Arg Arg Glu Asp Val Pro His Asp Leu Asn Gly Ser Gly
                325                 330                 335

Val Leu Ile Pro Arg Gly Glu Gly Arg Met Ile Thr Ala Ile Thr Trp
            340                 345                 350

Val Ser Ser Lys Trp Leu His Ser Ala Pro Gly Asp Lys Ala Leu Leu
    355                 360                 365

Arg Ala Tyr Ile Gly Arg Leu Gly Asp Glu Ala Trp Thr Ala Met Cys
370                 375                 380

Arg Ala Asp Ile Glu Arg Arg Val Ala Ala Glu Leu Arg Asp Leu Leu
385                 390                 395                 400

Gly Ile Ala Ala Ser Pro Leu Phe Cys Glu Leu Ala Ala Leu Pro Glu
                405                 410                 415

Ser Met Pro Gln Tyr Pro Val Gly His Val Glu Arg Leu Glu Ala Leu
            420                 425                 430

Arg Gly Ala Leu Cys Arg Ala Lys Pro Gly Leu Leu Leu Cys Gly Ala
    435                 440                 445

Gly Tyr Ala Gly Val Gly Ile Pro Asp Cys Ile Arg Gln Gly Lys Glu
450                 455                 460

Ala Ala Glu Ser Met Ala Ala Tyr Leu Arg Asp Gly Arg
465                 470                 475

<210> SEQ ID NO 14
<211> LENGTH: 493
<212> TYPE: PRT
<213> ORGANISM: Paenibacillus thiaminolyticus

<400> SEQUENCE: 14

Met Lys Ala Leu Arg Lys Leu Val Val Ile Gly Gly Gly Ile Thr Gly
1               5                   10                  15

Leu Ser Ala Ala Phe Tyr Ala Leu Lys Gln Ala Asp Glu Glu Gly Gln
            20                  25                  30

Pro Ile Ser Val Thr Ile Ile Glu Gln Ser Asp Arg Leu Gly Gly Lys
        35                  40                  45

Ile Gln Thr Leu Arg Lys Glu Gly Cys Val Ile Glu Lys Gly Pro Asp
    50                  55                  60

Ser Phe Leu Ala Arg Lys Leu Pro Met Ile Asp Leu Ala Arg Asp Leu
65                  70                  75                  80

Gly Met Asp Ser Glu Leu Val Ala Thr Asn Pro His Ala Lys Lys Thr
                85                  90                  95

Tyr Ile Leu Arg Arg Gly Lys Leu Tyr Arg Met Pro Pro Gly Leu Val
            100                 105                 110

Leu Gly Ile Pro Thr Glu Leu Gly Pro Phe Ala Lys Thr Gly Leu Ile
        115                 120                 125

Ser Pro Trp Gly Lys Leu Arg Ala Ala Met Asp Leu Phe Ile Lys Pro
    130                 135                 140

His Pro Ala Asp Glu Asp Glu Ser Val Gly Ala Phe Leu Asp Arg Arg
145                 150                 155                 160

Leu Gly Arg Glu Val Thr Glu His Ile Ala Glu Pro Leu Leu Ala Gly
                165                 170                 175
```

```
Ile Tyr Ala Gly Asp Leu Gln Ala Leu Ser Leu Gln Ala Thr Phe Pro
            180                 185                 190

Gln Phe Ala Gln Val Glu Arg Lys His Gly Gly Leu Ile Arg Gly Met
        195                 200                 205

Lys Ala Ser Arg Gln Ala Gly Gln Ser Val Pro Gly Leu Pro Asp Val
    210                 215                 220

Ala Lys Gly Thr Met Phe Leu Thr Phe Arg Asn Gly Leu Thr Ser Leu
225                 230                 235                 240

Val Glu Arg Leu Glu Glu Thr Leu Arg Asp Arg Ala Glu Leu Cys Leu
                245                 250                 255

Gly Ile Gly Ala Glu Gly Phe Glu Lys Arg Glu Asp Gly Thr Tyr Leu
            260                 265                 270

Val Arg Leu Ser Asp Gly Ser Arg Leu Gln Ala Asp Ala Val Ile Val
        275                 280                 285

Thr Thr Pro Ser Tyr His Ala Ala Ser Leu Leu Glu Glu His Val Asp
    290                 295                 300

Ala Ser Ala Leu Gln Ala Ile Arg His Val Ser Val Ala Asn Val Val
305                 310                 315                 320

Ser Val Phe Asp Arg Lys Gln Val Asn Asn Gln Phe Asp Gly Thr Gly
                325                 330                 335

Phe Val Ile Ser Arg Arg Glu Gly Arg Ala Ile Thr Ala Cys Thr Trp
            340                 345                 350

Thr Ser Val Lys Trp Pro His Thr Ser Arg Gly Asp Lys Leu Ile Ile
        355                 360                 365

Arg Cys Tyr Ile Gly Arg Ala Gly Asp Glu Glu Arg Val Asp Trp Pro
    370                 375                 380

Asp Glu Ala Leu Lys Arg Thr Val Arg Ser Glu Leu Arg Glu Leu Leu
385                 390                 395                 400

Asp Ile Asp Ile Asp Pro Glu Phe Val Glu Ile Thr Arg Leu Arg His
                405                 410                 415

Ser Met Pro Gln Tyr Pro Val Gly His Val Gln Ala Ile Arg Ser Leu
            420                 425                 430

Arg Asp Glu Val Gly Arg Thr Leu Pro Gly Val Phe Leu Ala Gly Gln
        435                 440                 445

Pro Tyr Glu Gly Val Gly Met Pro Asp Cys Val Arg Ser Gly Arg Asp
    450                 455                 460

Ala Ala Glu Ala Ala Val Ser Ala Met Gln Ala Met Ser Thr Glu Pro
465                 470                 475                 480

Glu Ala Pro Ala Glu Asp Ala Ala Thr Gly Thr Ala Gly
                485                 490

<210> SEQ ID NO 15
<211> LENGTH: 474
<212> TYPE: PRT
<213> ORGANISM: Paenibacillus polymyxa

<400> SEQUENCE: 15

Met Gly Asp Lys Lys Arg Arg Val Val Val Gly Gly Gly Leu Thr
1               5                   10                  15

Gly Leu Ser Ala Ala Phe Tyr Ile Arg Lys His Tyr Arg Glu Ala Gly
            20                  25                  30

Val Glu Pro Val Ile Thr Leu Val Glu Lys Ser Ser Met Gly Gly
        35                  40                  45

Met Ile Glu Thr Leu His Arg Asp Gly Phe Val Ile Glu Lys Gly Pro
```

```
            50                  55                  60
Asp Ser Phe Leu Ala Arg Lys Thr Ala Met Ile Asp Leu Ala Lys Glu
65                  70                  75                  80

Leu Glu Ile Asp His Glu Leu Val Ser Gln Asn Pro Glu Ser Lys Lys
                85                  90                  95

Thr Tyr Ile Met Gln Arg Gly Lys Leu His Pro Met Pro Ala Gly Leu
            100                 105                 110

Val Leu Gly Ile Pro Thr Glu Leu Arg Pro Phe Leu Arg Ser Gly Leu
        115                 120                 125

Val Ser Pro Ala Gly Lys Leu Arg Ala Leu Met Asp Phe Val Ile Pro
    130                 135                 140

Pro Arg Arg Thr Thr Glu Asp Glu Ser Leu Gly Tyr Met Ile Glu Arg
145                 150                 155                 160

Arg Leu Gly Ala Glu Val Leu Glu Asn Leu Thr Glu Pro Leu Leu Ala
                165                 170                 175

Gly Ile Tyr Ala Gly Asp Met Arg Arg Leu Ser Leu Gln Ala Thr Phe
            180                 185                 190

Pro Gln Phe Gly Glu Val Glu Arg Asp Tyr Gly Ser Leu Ile Arg Gly
        195                 200                 205

Met Met Thr Gly Arg Lys Pro Ala Glu Thr His Thr Gly Thr Lys Arg
    210                 215                 220

Ser Ala Phe Leu Asn Phe Arg Gln Gly Leu Gln Ser Leu Val His Ala
225                 230                 235                 240

Leu Val His Glu Leu Gln Asp Val Asp Gln Arg Leu Asn Thr Ala Val
                245                 250                 255

Lys Ser Leu Gln Arg Leu Asp Gly Ala Gln Thr Arg Tyr Arg Val Glu
            260                 265                 270

Leu Gly Asn Gly Glu Met Leu Glu Ala Asp Val Val Val Thr Val
        275                 280                 285

Pro Thr Tyr Val Ala Ser Glu Leu Leu Lys Pro His Val Asp Thr Ala
    290                 295                 300

Ala Leu Asp Ala Ile Asn Tyr Val Ser Val Ala Asn Val Val Leu Ala
305                 310                 315                 320

Phe Glu Lys Lys Glu Val His Val Phe Asp Gly Ser Gly Phe Leu
                325                 330                 335

Val Pro Arg Lys Glu Gly Arg Asn Ile Thr Ala Cys Thr Trp Thr Ser
            340                 345                 350

Thr Lys Trp Leu His Thr Ser Pro Asp Asp Lys Val Leu Leu Arg Cys
        355                 360                 365

Tyr Val Gly Arg Ser Gly Asp Glu Gln Asn Val Glu Leu Pro Asp Glu
    370                 375                 380

Ala Leu Thr Asn Leu Val Leu Lys Asp Leu Arg Glu Thr Met Gly Ile
385                 390                 395                 400

Glu Ala Val Pro Ile Phe Ser Glu Ile Thr Arg Leu Arg Lys Ser Met
                405                 410                 415

Pro Gln Tyr Pro Val Gly His Leu Gln His Ile Ala Ala Leu Arg Glu
            420                 425                 430

Glu Leu Gly Ser Lys Leu Pro Gly Val Tyr Ile Ala Gly Ala Gly Tyr
        435                 440                 445

Glu Gly Val Gly Leu Pro Asp Cys Ile Arg Gln Ala Lys Glu Met Ser
    450                 455                 460

Val Gln Ala Thr Gln Glu Leu Ala Ala Asp
465                 470
```

<210> SEQ ID NO 16
<211> LENGTH: 470
<212> TYPE: PRT
<213> ORGANISM: Bacillus atrophaeus

<400> SEQUENCE: 16

```
Met Ser Asp Gly Lys Lys His Leu Val Ile Ile Gly Gly Ile Thr
1               5                   10                  15

Gly Leu Ala Ser Ala Phe Tyr Met Glu Lys Glu Ile Arg Glu Lys Asn
                20                  25                  30

Leu Pro Leu Ser Val Thr Leu Val Glu Ala Ser Pro Arg Val Gly Gly
            35                  40                  45

Lys Ile Gln Thr Ala Arg Lys Asp Gly Tyr Ile Ile Glu Arg Gly Pro
50                  55                  60

Asp Ser Phe Leu Glu Arg Lys Lys Ser Ala Pro Glu Leu Val Glu Asp
65                  70                  75                  80

Leu Gly Leu Glu His Leu Leu Val Asn Asn Ala Thr Gly Gln Ser Tyr
                85                  90                  95

Val Leu Val Asn Glu Thr Leu His Pro Met Pro Lys Gly Ala Val Met
                100                 105                 110

Gly Ile Pro Thr Lys Ile Ala Pro Phe Met Ser Thr Gly Leu Phe Ser
            115                 120                 125

Phe Ser Gly Lys Ala Arg Ala Met Asp Phe Val Leu Pro Ala Ser
130                 135                 140

Lys Pro Lys Glu Asp Gln Ser Leu Gly Glu Phe Phe Arg Arg Val
145                 150                 155             160

Gly Asp Glu Val Val Glu Asn Leu Ile Glu Pro Leu Leu Ser Gly Ile
                165                 170                 175

Tyr Ala Gly Asp Ile Asp Arg Leu Ser Leu Met Ser Thr Phe Pro Gln
                180                 185                 190

Phe Tyr Gln Thr Glu Gln Lys His Arg Ser Leu Ile Leu Gly Met Lys
            195                 200                 205

Lys Thr Arg Pro Gln Gly Ser Gly Gln Arg Leu Thr Ala Lys Lys Gln
210                 215                 220

Gly Gln Phe Gln Thr Leu Lys Thr Gly Leu Gln Thr Leu Val Glu Glu
225                 230                 235             240

Leu Glu Asn Gln Leu Lys Leu Thr Lys Val Tyr Lys Gly Thr Lys Val
                245                 250                 255

Thr Asn Ile Ser Arg Gly Glu Lys Gly Cys Ser Ile Ala Leu Asp Asn
            260                 265                 270

Gly Met Thr Leu Asp Ala Asp Ala Ile Val Thr Ser Pro His Lys
            275                 280                 285

Ser Ala Ala Gly Met Phe Pro Asp Leu Pro Ala Val Ser Gln Leu Lys
            290                 295                 300

Asp Met His Ser Thr Ser Val Ala Asn Val Ala Leu Gly Phe Pro Gln
305                 310                 315                 320

Glu Ala Val Gln Met Glu His Glu Gly Thr Gly Phe Val Ile Ser Arg
                325                 330                 335

Asn Ser Asp Phe Ser Ile Thr Ala Cys Thr Trp Thr Asn Lys Lys Trp
            340                 345                 350

Pro His Ser Ala Pro Glu Gly Lys Thr Leu Leu Arg Ala Tyr Val Gly
            355                 360                 365

Lys Ala Gly Asp Glu Ser Ile Val Glu Leu Ser Asp Asn Glu Ile Ile
```

```
                            370                 375                 380
Lys Ile Val Leu Glu Asp Leu Lys Val Met Lys Ile Lys Gly Glu
385                 390                 395                 400

Pro Glu Met Thr Cys Val Thr Arg Trp Asn Glu Ser Met Pro Gln Tyr
                    405                 410                 415

His Val Gly His Lys Gln Arg Ile Lys Lys Val Arg Glu Ala Leu Ala
                420                 425                 430

Ala Ser Tyr Pro Gly Val Tyr Met Thr Gly Ala Ser Phe Glu Gly Val
            435                 440                 445

Gly Ile Pro Asp Cys Ile Asp Gln Gly Lys Ser Ala Val Ser Asp Val
450                 455                 460

Leu Ala Tyr Leu Phe Gly
465                 470

<210> SEQ ID NO 17
<211> LENGTH: 470
<212> TYPE: PRT
<213> ORGANISM: Bacillus atrophaeus

<400> SEQUENCE: 17

Met Ser Asp Gly Lys Lys His Leu Val Ile Ile Gly Gly Gly Ile Thr
1               5                   10                  15

Gly Leu Ala Ser Ala Phe Tyr Met Glu Lys Glu Ile Arg Glu Lys Asn
                20                  25                  30

Leu Pro Leu Ser Val Thr Leu Val Glu Ala Ser Pro Arg Val Gly Gly
            35                  40                  45

Lys Ile Gln Thr Ala Arg Lys Asp Gly Tyr Ile Ile Glu Arg Gly Pro
50                  55                  60

Asp Ser Phe Leu Glu Arg Lys Lys Ser Ala Pro Glu Leu Val Glu Asp
65                  70                  75                  80

Leu Gly Leu Glu His Leu Leu Val Asn Asn Ala Thr Gly Gln Ser Tyr
                85                  90                  95

Val Leu Val Asn Glu Thr Leu His Pro Met Pro Lys Gly Ala Val Met
                100                 105                 110

Gly Ile Pro Thr Lys Ile Ala Pro Phe Met Ser Thr Arg Leu Phe Ser
            115                 120                 125

Phe Ser Gly Lys Ala Arg Ala Ala Met Asp Phe Val Leu Pro Ala Ser
130                 135                 140

Lys Pro Lys Glu Asp Gln Ser Leu Gly Glu Phe Phe Arg Arg Arg Val
145                 150                 155                 160

Gly Asp Glu Val Val Glu Asn Leu Ile Glu Pro Leu Leu Ser Gly Ile
                165                 170                 175

Tyr Ala Gly Asp Ile Asp Arg Leu Ser Leu Met Ser Thr Phe Pro Gln
            180                 185                 190

Phe Tyr Gln Thr Glu Gln Lys His Arg Ser Leu Ile Leu Gly Met Lys
        195                 200                 205

Lys Thr Arg Pro Gln Gly Ser Gly Gln Gln Leu Thr Ala Lys Lys Gln
210                 215                 220

Gly Gln Phe Gln Thr Leu Lys Thr Gly Leu Gln Thr Leu Val Glu Glu
225                 230                 235                 240

Leu Glu Asn Gln Leu Lys Leu Thr Lys Val Tyr Lys Gly Thr Lys Val
                245                 250                 255

Thr Asn Ile Ser Arg Gly Glu Lys Gly Cys Ser Ile Ala Leu Asp Asn
            260                 265                 270
```

```
Gly Met Thr Leu Asp Ala Asp Ala Ile Val Thr Ser Pro His Lys
            275                 280                 285

Ser Ala Ala Gly Met Phe Pro Asp Leu Pro Ala Val Ser Gln Leu Lys
290                 295                 300

Asp Met His Ser Thr Ser Val Ala Asn Val Ala Leu Gly Phe Pro Gln
305                 310                 315                 320

Glu Ala Val Gln Met Glu His Glu Gly Thr Gly Phe Val Ile Ser Arg
                325                 330                 335

Asn Ser Asp Phe Ser Ile Thr Ala Cys Thr Trp Thr Asn Lys Lys Trp
            340                 345                 350

Pro His Ser Ala Pro Glu Gly Lys Thr Leu Leu Arg Ala Tyr Val Gly
            355                 360                 365

Lys Ala Gly Asp Glu Ser Ile Val Glu Leu Ser Asp Asn Glu Ile Ile
370                 375                 380

Lys Ile Val Leu Glu Asp Leu Lys Lys Val Met Lys Ile Lys Gly Glu
385                 390                 395                 400

Pro Glu Met Thr Cys Val Thr Arg Trp Asn Glu Ser Met Pro Gln Tyr
                405                 410                 415

His Val Gly His Lys Gln Arg Ile Lys Lys Val Arg Glu Ala Leu Ala
            420                 425                 430

Ala Ser Tyr Pro Gly Val Tyr Met Thr Gly Ala Ser Phe Glu Gly Val
            435                 440                 445

Gly Ile Pro Asp Cys Ile Asp Gln Gly Lys Ser Ala Val Ser Asp Val
            450                 455                 460

Leu Ala Tyr Leu Phe Glu
465                 470

<210> SEQ ID NO 18
<211> LENGTH: 475
<212> TYPE: PRT
<213> ORGANISM: Artificial Sequence
<220> FEATURE:
<223> OTHER INFORMATION: Recombinant

<400> SEQUENCE: 18

Lys Lys Ile Ala Val Ile Gly Gly Gly Ile Thr Gly Leu Ser Val Ala
1               5                   10                  15

Tyr Tyr Val Arg Lys Leu Leu Arg Glu Gln Gly Val Asn Ala Gly Val
                20                  25                  30

Thr Leu Val Glu Gln Ser Asp Arg Leu Gly Gly Lys Ile Arg Ser Leu
            35                  40                  45

Arg Arg Asp Gly Phe Thr Ile Glu Gln Gly Pro Asp Ser Met Ile Ala
50                  55                  60

Arg Lys Pro Ala Ala Leu Glu Leu Ile Arg Glu Leu Gly Leu Glu Asp
65                  70                  75                  80

Lys Leu Ala Gly Thr Asn Pro Gln Ala Lys Arg Ser Tyr Ile Leu His
                85                  90                  95

Arg Gly Lys Phe His Pro Met Pro Pro Gly Leu Met Leu Gly Ile Pro
            100                 105                 110

Thr Gln Met Trp Pro Met Val Lys Thr Gly Leu Leu Ser Pro Ala Gly
            115                 120                 125

Lys Leu Arg Ala Ala Met Asp Leu Leu Leu Pro Ala Arg Arg Gly Gly
130                 135                 140

Gly Asp Glu Ser Leu Gly Gly Phe Ile Arg Arg Arg Leu Gly Arg Glu
145                 150                 155                 160
```

Val Leu Glu Gln Met Thr Glu Pro Leu Leu Ala Gly Ile Tyr Ala Gly
            165                 170                 175

Asp Thr Glu Gln Leu Ser Leu Lys Ala Thr Phe Pro Gln Phe Met Glu
        180                 185                 190

Met Glu Arg Lys His Arg Ser Leu Ile Leu Gly Leu Leu Ala Gly Lys
    195                 200                 205

Lys Gln Pro Pro Arg Pro Gly Ser Gln Val Pro Leu Pro Lys Ala
210                 215                 220

Ala Gln Thr Ser Met Phe Leu Thr Leu Thr Gly Leu Glu Gly Leu
225                 230                 235                 240

Thr Glu Ala Leu Glu Glu Ser Leu Ser Glu Glu Lys Ile Ile Thr Gly
            245                 250                 255

Gln Ala Val Thr Gly Leu Ser Gln Gln Glu Ala Gly Tyr Glu Leu Asn
            260                 265                 270

Leu Ser Gly Gly Glu Arg Leu Asn Ala Asp Gly Val Ile Leu Ala Val
            275                 280                 285

Pro Ala Phe Ala Ala Ala Arg Leu Leu Asp Gly Val Pro Glu Ala Ala
290                 295                 300

Tyr Leu Glu Arg Ile Arg Tyr Val Ser Val Ala Asn Leu Ala Phe Ala
305                 310                 315                 320

Tyr Arg Arg Glu Asp Val Pro His Asp Leu Asn Gly Ser Gly Val Leu
            325                 330                 335

Ile Pro Arg Gly Glu Gly Arg Met Ile Thr Ala Ile Thr Trp Val Ser
            340                 345                 350

Ser Lys Trp Leu His Ser Ala Pro Gly Asp Lys Ala Leu Leu Arg Ala
        355                 360                 365

Tyr Ile Gly Arg Leu Gly Asp Glu Ala Trp Thr Ala Met Cys Arg Ala
370                 375                 380

Asp Ile Glu Arg Arg Val Ala Ala Glu Leu Arg Asp Leu Leu Gly Ile
385                 390                 395                 400

Ala Ala Ser Pro Leu Phe Cys Glu Leu Ala Ala Leu Pro Glu Ser Met
            405                 410                 415

Pro Gln Tyr Pro Val Gly His Val Glu Arg Leu Glu Ala Leu Arg Gly
            420                 425                 430

Ala Leu Cys Arg Ala Lys Pro Gly Leu Leu Leu Cys Gly Ala Gly Tyr
        435                 440                 445

Ala Gly Val Gly Ile Pro Asp Cys Ile Arg Gln Gly Lys Glu Ala Ala
        450                 455                 460

Glu Ser Met Ala Ala Tyr Leu Arg Asp Gly Arg
465                 470                 475

<210> SEQ ID NO 19
<211> LENGTH: 489
<212> TYPE: PRT
<213> ORGANISM: Artificial Sequence
<220> FEATURE:
<223> OTHER INFORMATION: Recombinant

<400> SEQUENCE: 19

Arg Lys Leu Val Val Ile Gly Gly Gly Ile Thr Gly Leu Ser Ala Ala
1               5                   10                  15

Phe Tyr Ala Leu Lys Gln Ala Asp Glu Glu Gly Gln Pro Ile Ser Val
            20                  25                  30

Thr Ile Ile Glu Gln Ser Asp Arg Leu Gly Gly Lys Ile Gln Thr Leu
        35                  40                  45

```
Arg Lys Glu Gly Cys Val Ile Glu Lys Gly Pro Asp Ser Phe Leu Ala
 50                  55                  60

Arg Lys Leu Pro Met Ile Asp Leu Ala Arg Asp Leu Gly Met Asp Ser
 65                  70                  75                  80

Glu Leu Val Ala Thr Asn Pro His Ala Lys Lys Thr Tyr Ile Leu Arg
                 85                  90                  95

Arg Gly Lys Leu Tyr Arg Met Pro Pro Gly Leu Val Leu Gly Ile Pro
             100                 105                 110

Thr Glu Leu Gly Pro Phe Ala Lys Thr Gly Leu Ile Ser Pro Trp Gly
         115                 120                 125

Lys Leu Arg Ala Ala Met Asp Leu Phe Ile Lys Pro His Pro Ala Asp
130                 135                 140

Glu Asp Glu Ser Val Gly Ala Phe Leu Asp Arg Arg Leu Gly Arg Glu
145                 150                 155                 160

Val Thr Glu His Ile Ala Glu Pro Leu Leu Ala Gly Ile Tyr Ala Gly
                165                 170                 175

Asp Leu Gln Ala Leu Ser Leu Gln Ala Thr Phe Pro Gln Phe Ala Gln
             180                 185                 190

Val Glu Arg Lys His Gly Gly Leu Ile Arg Gly Met Lys Ala Ser Arg
         195                 200                 205

Gln Ala Gly Gln Ser Val Pro Gly Leu Pro Asp Val Ala Lys Gly Thr
210                 215                 220

Met Phe Leu Thr Phe Arg Asn Gly Leu Thr Ser Leu Val Glu Arg Leu
225                 230                 235                 240

Glu Glu Thr Leu Arg Asp Arg Ala Glu Leu Cys Leu Gly Ile Gly Ala
                245                 250                 255

Glu Gly Phe Glu Lys Arg Glu Asp Gly Thr Tyr Leu Val Arg Leu Ser
             260                 265                 270

Asp Gly Ser Arg Leu Gln Ala Asp Ala Val Ile Val Thr Thr Pro Ser
         275                 280                 285

Tyr His Ala Ala Ser Leu Leu Glu Glu His Val Asp Ala Ser Ala Leu
290                 295                 300

Gln Ala Ile Arg His Val Ser Val Ala Asn Val Val Ser Val Phe Asp
305                 310                 315                 320

Arg Lys Gln Val Asn Asn Gln Phe Asp Gly Thr Gly Phe Val Ile Ser
                325                 330                 335

Arg Arg Glu Gly Arg Ala Ile Thr Ala Cys Thr Trp Thr Ser Val Lys
             340                 345                 350

Trp Pro His Thr Ser Arg Gly Asp Lys Leu Ile Ile Arg Cys Tyr Ile
         355                 360                 365

Gly Arg Ala Gly Asp Glu Glu Arg Val Asp Trp Pro Asp Glu Ala Leu
370                 375                 380

Lys Arg Thr Val Arg Ser Glu Leu Arg Glu Leu Leu Asp Ile Asp Ile
385                 390                 395                 400

Asp Pro Glu Phe Val Glu Ile Thr Arg Leu Arg His Ser Met Pro Gln
                405                 410                 415

Tyr Pro Val Gly His Val Gln Ala Ile Arg Ser Leu Arg Asp Glu Val
             420                 425                 430

Gly Arg Thr Leu Pro Gly Val Phe Leu Ala Gly Gln Pro Tyr Glu Gly
         435                 440                 445

Val Gly Met Pro Asp Cys Val Arg Ser Gly Arg Asp Ala Ala Glu Ala
450                 455                 460

Ala Val Ser Ala Met Gln Ala Met Ser Thr Glu Pro Glu Ala Pro Ala
```

```
                465                 470                 475                 480
Glu Asp Ala Ala Thr Gly Thr Ala Gly
                            485

<210> SEQ ID NO 20
<211> LENGTH: 469
<212> TYPE: PRT
<213> ORGANISM: Artificial Sequence
<220> FEATURE:
<223> OTHER INFORMATION: Recombinant

<400> SEQUENCE: 20

Arg Arg Val Val Val Gly Gly Leu Thr Gly Leu Ser Ala Ala
1               5                   10                  15

Phe Tyr Ile Arg Lys His Tyr Arg Glu Ala Gly Val Glu Pro Val Ile
                20                  25                  30

Thr Leu Val Glu Lys Ser Ser Met Gly Gly Met Ile Glu Thr Leu
            35                  40                  45

His Arg Asp Gly Phe Val Ile Glu Lys Gly Pro Asp Ser Phe Leu Ala
        50                  55                  60

Arg Lys Thr Ala Met Ile Asp Leu Ala Lys Glu Leu Glu Ile Asp His
65                  70                  75                  80

Glu Leu Val Ser Gln Asn Pro Glu Ser Lys Lys Thr Tyr Ile Met Gln
                85                  90                  95

Arg Gly Lys Leu His Pro Met Pro Ala Gly Leu Val Leu Gly Ile Pro
            100                 105                 110

Thr Glu Leu Arg Pro Phe Leu Arg Ser Gly Leu Val Ser Pro Ala Gly
        115                 120                 125

Lys Leu Arg Ala Leu Met Asp Phe Val Ile Pro Pro Arg Arg Thr Thr
130                 135                 140

Glu Asp Glu Ser Leu Gly Tyr Met Ile Glu Arg Arg Leu Gly Ala Glu
145                 150                 155                 160

Val Leu Glu Asn Leu Thr Glu Pro Leu Leu Ala Gly Ile Tyr Ala Gly
                165                 170                 175

Asp Met Arg Arg Leu Ser Leu Gln Ala Thr Phe Pro Gln Phe Gly Glu
            180                 185                 190

Val Glu Arg Asp Tyr Gly Ser Leu Ile Arg Gly Met Met Thr Gly Arg
        195                 200                 205

Lys Pro Ala Glu Thr His Thr Gly Thr Lys Arg Ser Ala Phe Leu Asn
210                 215                 220

Phe Arg Gln Gly Leu Gln Ser Leu Val His Ala Leu Val His Glu Leu
225                 230                 235                 240

Gln Asp Val Asp Gln Arg Leu Asn Thr Ala Val Lys Ser Leu Gln Arg
                245                 250                 255

Leu Asp Gly Ala Gln Thr Arg Tyr Arg Val Glu Leu Gly Asn Gly Glu
            260                 265                 270

Met Leu Glu Ala Asp Asp Val Val Thr Val Pro Thr Tyr Val Ala
        275                 280                 285

Ser Glu Leu Leu Lys Pro His Val Asp Thr Ala Ala Leu Asp Ala Ile
290                 295                 300

Asn Tyr Val Ser Val Ala Asn Val Leu Ala Phe Glu Lys Lys Glu
305                 310                 315                 320

Val Glu His Val Phe Asp Gly Ser Gly Phe Leu Val Pro Arg Lys Glu
                325                 330                 335

Gly Arg Asn Ile Thr Ala Cys Thr Trp Thr Ser Thr Lys Trp Leu His
```

-continued

```
                340                 345                 350
Thr Ser Pro Asp Asp Lys Val Leu Leu Arg Cys Tyr Val Gly Arg Ser
            355                 360                 365
Gly Asp Glu Gln Asn Val Glu Leu Pro Asp Glu Ala Leu Thr Asn Leu
        370                 375                 380
Val Leu Lys Asp Leu Arg Glu Thr Met Gly Ile Glu Ala Val Pro Ile
385                 390                 395                 400
Phe Ser Glu Ile Thr Arg Leu Arg Lys Ser Met Pro Gln Tyr Pro Val
                405                 410                 415
Gly His Leu Gln His Ile Ala Ala Leu Arg Glu Glu Leu Gly Ser Lys
            420                 425                 430
Leu Pro Gly Val Tyr Ile Ala Gly Ala Gly Tyr Glu Gly Val Gly Leu
        435                 440                 445
Pro Asp Cys Ile Arg Gln Ala Lys Glu Met Ser Val Gln Ala Thr Gln
    450                 455                 460
Glu Leu Ala Ala Asp
465

<210> SEQ ID NO 21
<211> LENGTH: 465
<212> TYPE: PRT
<213> ORGANISM: Artificial Sequence
<220> FEATURE:
<223> OTHER INFORMATION: Recombinant

<400> SEQUENCE: 21

Lys His Leu Val Ile Ile Gly Gly Gly Ile Thr Gly Leu Ala Ser Ala
1               5                   10                  15
Phe Tyr Met Glu Lys Glu Ile Arg Glu Lys Asn Leu Pro Leu Ser Val
                20                  25                  30
Thr Leu Val Glu Ala Ser Pro Arg Val Gly Gly Lys Ile Gln Thr Ala
            35                  40                  45
Arg Lys Asp Gly Tyr Ile Ile Glu Arg Gly Pro Asp Ser Phe Leu Glu
        50                  55                  60
Arg Lys Lys Ser Ala Pro Glu Leu Val Glu Asp Leu Gly Leu Glu His
65                  70                  75                  80
Leu Leu Val Asn Asn Ala Thr Gly Gln Ser Tyr Val Leu Val Asn Glu
                85                  90                  95
Thr Leu His Pro Met Pro Lys Gly Ala Val Met Gly Ile Pro Thr Lys
                100                 105                 110
Ile Ala Pro Phe Met Ser Thr Arg Leu Phe Ser Phe Ser Gly Lys Ala
            115                 120                 125
Arg Ala Ala Met Asp Phe Val Leu Pro Ala Ser Lys Pro Lys Glu Asp
        130                 135                 140
Gln Ser Leu Gly Glu Phe Phe Arg Arg Val Gly Asp Glu Val Val
145                 150                 155                 160
Glu Asn Leu Ile Glu Pro Leu Leu Ser Gly Ile Tyr Ala Gly Asp Ile
                165                 170                 175
Asp Arg Leu Ser Leu Met Ser Thr Phe Pro Gln Phe Tyr Gln Thr Glu
            180                 185                 190
Gln Lys His Arg Ser Leu Ile Leu Gly Met Lys Lys Thr Arg Pro Gln
        195                 200                 205
Gly Ser Gly Gln Gln Leu Thr Ala Lys Lys Gln Gly Gln Phe Gln Thr
    210                 215                 220
Leu Lys Thr Gly Leu Gln Thr Leu Val Glu Glu Leu Glu Asn Gln Leu
```

```
                225                 230                 235                 240
Lys Leu Thr Lys Val Tyr Lys Gly Thr Lys Val Thr Asn Ile Ser Arg
            245                 250                 255

Gly Glu Lys Gly Cys Ser Ile Ala Leu Asp Asn Gly Met Thr Leu Asp
            260                 265                 270

Ala Asp Ala Ala Ile Val Thr Ser Pro His Lys Ser Ala Ala Gly Met
            275                 280                 285

Phe Pro Asp Leu Pro Ala Val Ser Gln Leu Lys Asp Met His Ser Thr
            290                 295                 300

Ser Val Ala Asn Val Ala Leu Gly Phe Pro Gln Glu Ala Val Gln Met
305                 310                 315                 320

Glu His Glu Gly Thr Gly Phe Val Ile Ser Arg Asn Ser Asp Phe Ser
            325                 330                 335

Ile Thr Ala Cys Thr Trp Thr Asn Lys Lys Trp Pro His Ser Ala Pro
            340                 345                 350

Glu Gly Lys Thr Leu Leu Arg Ala Tyr Val Gly Lys Ala Gly Asp Glu
            355                 360                 365

Ser Ile Val Glu Leu Ser Asp Asn Glu Ile Ile Lys Ile Val Leu Glu
            370                 375                 380

Asp Leu Lys Lys Val Met Lys Ile Lys Gly Glu Pro Glu Met Thr Cys
385                 390                 395                 400

Val Thr Arg Trp Asn Glu Ser Met Pro Gln Tyr His Val Gly His Lys
            405                 410                 415

Gln Arg Ile Lys Lys Val Arg Glu Ala Leu Ala Ala Ser Tyr Pro Gly
            420                 425                 430

Val Tyr Met Thr Gly Ala Ser Phe Glu Gly Val Gly Ile Pro Asp Cys
            435                 440                 445

Ile Asp Gln Gly Lys Ser Ala Val Ser Asp Val Leu Ala Tyr Leu Phe
            450                 455                 460

Glu
465

<210> SEQ ID NO 22
<211> LENGTH: 473
<212> TYPE: PRT
<213> ORGANISM: Artificial Sequence
<220> FEATURE:
<223> OTHER INFORMATION: Recombinant

<400> SEQUENCE: 22

Ile Ala Val Ile Gly Gly Gly Ile Thr Gly Leu Ser Val Ala Tyr Tyr
1               5                   10                  15

Val Arg Lys Leu Leu Arg Glu Gln Gly Val Asn Ala Gly Val Thr Leu
            20                  25                  30

Val Glu Gln Ser Asp Arg Leu Gly Gly Lys Ile Arg Ser Leu Arg Arg
        35                  40                  45

Asp Gly Phe Thr Ile Glu Gln Gly Pro Asp Ser Met Ile Ala Arg Lys
    50                  55                  60

Pro Ala Ala Leu Glu Leu Ile Arg Glu Leu Gly Leu Glu Asp Lys Leu
65                  70                  75                  80

Ala Gly Thr Asn Pro Gln Ala Lys Arg Ser Tyr Ile Leu His Arg Gly
            85                  90                  95

Lys Phe His Pro Met Pro Pro Gly Leu Met Leu Gly Ile Pro Thr Gln
            100                 105                 110

Met Trp Pro Met Val Lys Thr Gly Leu Leu Ser Pro Ala Gly Lys Leu
```

```
                115                 120                 125
    Arg Ala Ala Met Asp Leu Leu Leu Pro Ala Arg Arg Gly Gly Asp
            130                 135                 140
    Glu Ser Leu Gly Gly Phe Ile Arg Arg Leu Gly Arg Glu Val Leu
145                 150                 155                 160
    Glu Gln Met Thr Glu Pro Leu Leu Ala Gly Ile Tyr Ala Gly Asp Thr
                165                 170                 175
    Glu Gln Leu Ser Leu Lys Ala Thr Phe Pro Gln Phe Met Glu Met Glu
                180                 185                 190
    Arg Lys His Arg Ser Leu Ile Leu Gly Leu Leu Ala Gly Lys Lys Gln
                195                 200                 205
    Pro Pro Arg Pro Gly Gly Ser Gln Val Pro Leu Pro Lys Ala Ala Gln
            210                 215                 220
    Thr Ser Met Phe Leu Thr Leu Thr Gly Gly Leu Glu Gly Leu Thr Glu
225                 230                 235                 240
    Ala Leu Glu Glu Ser Leu Ser Glu Glu Lys Ile Ile Thr Gly Gln Ala
                245                 250                 255
    Val Thr Gly Leu Ser Gln Gln Glu Ala Gly Tyr Glu Leu Asn Leu Ser
                260                 265                 270
    Gly Gly Glu Arg Leu Asn Ala Asp Gly Val Ile Leu Ala Val Pro Ala
                275                 280                 285
    Phe Ala Ala Ala Arg Leu Leu Asp Gly Val Pro Glu Ala Ala Tyr Leu
                290                 295                 300
    Glu Arg Ile Arg Tyr Val Ser Val Ala Asn Leu Ala Phe Ala Tyr Arg
305                 310                 315                 320
    Arg Glu Asp Val Pro His Asp Leu Asn Gly Ser Gly Val Leu Ile Pro
                        325                 330                 335
    Arg Gly Glu Gly Arg Met Ile Thr Ala Ile Thr Trp Val Ser Ser Lys
                340                 345                 350
    Trp Leu His Ser Ala Pro Gly Asp Lys Ala Leu Leu Arg Ala Tyr Ile
                355                 360                 365
    Gly Arg Leu Gly Asp Glu Ala Trp Thr Ala Met Cys Arg Ala Asp Ile
            370                 375                 380
    Glu Arg Arg Val Ala Ala Glu Leu Arg Asp Leu Leu Gly Ile Ala Ala
385                 390                 395                 400
    Ser Pro Leu Phe Cys Glu Leu Ala Ala Leu Pro Glu Ser Met Pro Gln
                    405                 410                 415
    Tyr Pro Val Gly His Val Glu Arg Leu Glu Ala Leu Arg Gly Ala Leu
                420                 425                 430
    Cys Arg Ala Lys Pro Gly Leu Leu Leu Cys Gly Ala Gly Tyr Ala Gly
                435                 440                 445
    Val Gly Ile Pro Asp Cys Ile Arg Gln Gly Lys Glu Ala Ala Glu Ser
            450                 455                 460
    Met Ala Ala Tyr Leu Arg Asp Gly Arg
465                 470

<210> SEQ ID NO 23
<211> LENGTH: 487
<212> TYPE: PRT
<213> ORGANISM: Artificial Sequence
<220> FEATURE:
<223> OTHER INFORMATION: Recombinant

<400> SEQUENCE: 23

Leu Val Val Ile Gly Gly Gly Ile Thr Gly Leu Ser Ala Ala Phe Tyr
```

-continued

```
1               5                   10                  15
Ala Leu Lys Gln Ala Asp Glu Glu Gly Gln Pro Ile Ser Val Thr Ile
            20                  25                  30
Ile Glu Gln Ser Asp Arg Leu Gly Gly Lys Ile Gln Thr Leu Arg Lys
            35                  40                  45
Glu Gly Cys Val Ile Glu Lys Gly Pro Asp Ser Phe Leu Ala Arg Lys
         50                  55                  60
Leu Pro Met Ile Asp Leu Ala Arg Asp Leu Gly Met Asp Ser Glu Leu
 65                  70                  75                  80
Val Ala Thr Asn Pro His Ala Lys Lys Thr Tyr Ile Leu Arg Arg Gly
                85                  90                  95
Lys Leu Tyr Arg Met Pro Pro Gly Leu Val Leu Gly Ile Pro Thr Glu
            100                 105                 110
Leu Gly Pro Phe Ala Lys Thr Gly Leu Ile Ser Pro Trp Gly Lys Leu
            115                 120                 125
Arg Ala Ala Met Asp Leu Phe Ile Lys Pro His Pro Ala Asp Glu Asp
            130                 135                 140
Glu Ser Val Gly Ala Phe Leu Asp Arg Arg Leu Gly Arg Glu Val Thr
145                 150                 155                 160
Glu His Ile Ala Glu Pro Leu Leu Ala Gly Ile Tyr Ala Gly Asp Leu
                165                 170                 175
Gln Ala Leu Ser Leu Gln Ala Thr Phe Pro Gln Phe Ala Gln Val Glu
            180                 185                 190
Arg Lys His Gly Gly Leu Ile Arg Gly Met Lys Ala Ser Arg Gln Ala
            195                 200                 205
Gly Gln Ser Val Pro Gly Leu Pro Asp Val Ala Lys Gly Thr Met Phe
            210                 215                 220
Leu Thr Phe Arg Asn Gly Leu Thr Ser Leu Val Glu Arg Leu Glu Glu
225                 230                 235                 240
Thr Leu Arg Asp Arg Ala Glu Leu Cys Leu Gly Ile Gly Ala Glu Gly
                245                 250                 255
Phe Glu Lys Arg Glu Asp Gly Thr Tyr Leu Val Arg Leu Ser Asp Gly
            260                 265                 270
Ser Arg Leu Gln Ala Asp Ala Val Ile Val Thr Thr Pro Ser Tyr His
            275                 280                 285
Ala Ala Ser Leu Leu Glu Glu His Val Asp Ala Ser Ala Leu Gln Ala
            290                 295                 300
Ile Arg His Val Ser Val Ala Asn Val Val Ser Val Phe Asp Arg Lys
305                 310                 315                 320
Gln Val Asn Asn Gln Phe Asp Gly Thr Gly Phe Val Ile Ser Arg Arg
                325                 330                 335
Glu Gly Arg Ala Ile Thr Ala Cys Thr Trp Thr Ser Val Lys Trp Pro
            340                 345                 350
His Thr Ser Arg Gly Asp Lys Leu Ile Ile Arg Cys Tyr Ile Gly Arg
            355                 360                 365
Ala Gly Asp Glu Glu Arg Val Asp Trp Pro Asp Glu Ala Leu Lys Arg
            370                 375                 380
Thr Val Arg Ser Glu Leu Arg Glu Leu Leu Asp Ile Asp Ile Asp Pro
385                 390                 395                 400
Glu Phe Val Glu Ile Thr Arg Leu Arg His Ser Met Pro Gln Tyr Pro
                405                 410                 415
Val Gly His Val Gln Ala Ile Arg Ser Leu Arg Asp Glu Val Gly Arg
            420                 425                 430
```

Thr Leu Pro Gly Val Phe Leu Ala Gly Gln Pro Tyr Glu Gly Val Gly
        435                 440                 445

Met Pro Asp Cys Val Arg Ser Gly Arg Asp Ala Ala Glu Ala Ala Val
450                 455                 460

Ser Ala Met Gln Ala Met Ser Thr Glu Pro Glu Ala Pro Ala Glu Asp
465                 470                 475                 480

Ala Ala Thr Gly Thr Ala Gly
                485

<210> SEQ ID NO 24
<211> LENGTH: 467
<212> TYPE: PRT
<213> ORGANISM: Artificial Sequence
<220> FEATURE:
<223> OTHER INFORMATION: Recombinant

<400> SEQUENCE: 24

Val Val Val Gly Gly Gly Leu Thr Gly Leu Ser Ala Ala Phe Tyr
1               5                   10                  15

Ile Arg Lys His Tyr Arg Glu Ala Gly Val Glu Pro Val Ile Thr Leu
                20                  25                  30

Val Glu Lys Ser Ser Ser Met Gly Gly Met Ile Glu Thr Leu His Arg
            35                  40                  45

Asp Gly Phe Val Ile Glu Lys Gly Pro Asp Ser Phe Leu Ala Arg Lys
        50                  55                  60

Thr Ala Met Ile Asp Leu Ala Lys Glu Leu Glu Ile Asp His Glu Leu
65                  70                  75                  80

Val Ser Gln Asn Pro Glu Ser Lys Lys Thr Tyr Ile Met Gln Arg Gly
                85                  90                  95

Lys Leu His Pro Met Pro Ala Gly Leu Val Leu Gly Ile Pro Thr Glu
            100                 105                 110

Leu Arg Pro Phe Leu Arg Ser Gly Leu Val Ser Pro Ala Gly Lys Leu
        115                 120                 125

Arg Ala Leu Met Asp Phe Val Ile Pro Pro Arg Arg Thr Thr Glu Asp
130                 135                 140

Glu Ser Leu Gly Tyr Met Ile Glu Arg Arg Leu Gly Ala Glu Val Leu
145                 150                 155                 160

Glu Asn Leu Thr Glu Pro Leu Leu Ala Gly Ile Tyr Ala Gly Asp Met
                165                 170                 175

Arg Arg Leu Ser Leu Gln Ala Thr Phe Pro Gln Phe Gly Glu Val Glu
            180                 185                 190

Arg Asp Tyr Gly Ser Leu Ile Arg Gly Met Met Thr Gly Arg Lys Pro
        195                 200                 205

Ala Glu Thr His Thr Gly Thr Lys Arg Ser Ala Phe Leu Asn Phe Arg
210                 215                 220

Gln Gly Leu Gln Ser Leu Val His Ala Leu Val His Glu Leu Gln Asp
225                 230                 235                 240

Val Asp Gln Arg Leu Asn Thr Ala Val Lys Ser Leu Gln Arg Leu Asp
                245                 250                 255

Gly Ala Gln Thr Arg Tyr Arg Val Glu Leu Gly Asn Gly Glu Met Leu
            260                 265                 270

Glu Ala Asp Asp Val Val Val Thr Val Pro Thr Tyr Val Ala Ser Glu
        275                 280                 285

Leu Leu Lys Pro His Val Asp Thr Ala Ala Leu Asp Ala Ile Asn Tyr
290                 295                 300

```
Val Ser Val Ala Asn Val Val Leu Ala Phe Glu Lys Glu Val Glu
305                 310                 315                 320

His Val Phe Asp Gly Ser Gly Phe Leu Val Pro Arg Lys Glu Gly Arg
                325                 330                 335

Asn Ile Thr Ala Cys Thr Trp Thr Ser Thr Lys Trp Leu His Thr Ser
                340                 345                 350

Pro Asp Asp Lys Val Leu Leu Arg Cys Tyr Val Gly Arg Ser Gly Asp
                355                 360                 365

Glu Gln Asn Val Glu Leu Pro Asp Glu Ala Leu Thr Asn Leu Val Leu
                370                 375                 380

Lys Asp Leu Arg Glu Thr Met Gly Ile Glu Ala Val Pro Ile Phe Ser
385                 390                 395                 400

Glu Ile Thr Arg Leu Arg Lys Ser Met Pro Gln Tyr Pro Val Gly His
                405                 410                 415

Leu Gln His Ile Ala Ala Leu Arg Glu Glu Leu Gly Ser Lys Leu Pro
                420                 425                 430

Gly Val Tyr Ile Ala Gly Ala Gly Tyr Glu Gly Val Gly Leu Pro Asp
                435                 440                 445

Cys Ile Arg Gln Ala Lys Glu Met Ser Val Gln Ala Thr Gln Glu Leu
450                 455                 460

Ala Ala Asp
465

<210> SEQ ID NO 25
<211> LENGTH: 463
<212> TYPE: PRT
<213> ORGANISM: Artificial Sequence
<220> FEATURE:
<223> OTHER INFORMATION: Recombinant

<400> SEQUENCE: 25

Leu Val Ile Ile Gly Gly Gly Ile Thr Gly Leu Ala Ser Ala Phe Tyr
1               5                   10                  15

Met Glu Lys Glu Ile Arg Glu Lys Asn Leu Pro Leu Ser Val Thr Leu
                20                  25                  30

Val Glu Ala Ser Pro Arg Val Gly Gly Lys Ile Gln Thr Ala Arg Lys
                35                  40                  45

Asp Gly Tyr Ile Ile Glu Arg Gly Pro Asp Ser Phe Leu Glu Arg Lys
                50                  55                  60

Lys Ser Ala Pro Glu Leu Val Glu Asp Leu Gly Leu Glu His Leu Leu
65                  70                  75                  80

Val Asn Asn Ala Thr Gly Gln Ser Tyr Val Leu Val Asn Glu Thr Leu
                85                  90                  95

His Pro Met Pro Lys Gly Ala Val Met Gly Ile Pro Thr Lys Ile Ala
                100                 105                 110

Pro Phe Met Ser Thr Arg Leu Phe Ser Phe Ser Gly Lys Ala Arg Ala
                115                 120                 125

Ala Met Asp Phe Val Leu Pro Ala Ser Lys Pro Lys Glu Asp Gln Ser
                130                 135                 140

Leu Gly Glu Phe Phe Arg Arg Arg Val Gly Asp Glu Val Val Glu Asn
145                 150                 155                 160

Leu Ile Glu Pro Leu Leu Ser Gly Ile Tyr Ala Gly Asp Ile Asp Arg
                165                 170                 175

Leu Ser Leu Met Ser Thr Phe Pro Gln Phe Tyr Gln Thr Glu Gln Lys
                180                 185                 190
```

His Arg Ser Leu Ile Leu Gly Met Lys Lys Thr Arg Pro Gln Gly Ser
    195                 200                 205

Gly Gln Gln Leu Thr Ala Lys Lys Gln Gly Gln Phe Gln Thr Leu Lys
    210                 215                 220

Thr Gly Leu Gln Thr Leu Val Glu Glu Leu Glu Asn Gln Leu Lys Leu
225                 230                 235                 240

Thr Lys Val Tyr Lys Gly Thr Lys Val Thr Asn Ile Ser Arg Gly Glu
                245                 250                 255

Lys Gly Cys Ser Ile Ala Leu Asp Asn Gly Met Thr Leu Asp Ala Asp
            260                 265                 270

Ala Ala Ile Val Thr Ser Pro His Lys Ser Ala Ala Gly Met Phe Pro
            275                 280                 285

Asp Leu Pro Ala Val Ser Gln Leu Lys Asp Met His Ser Thr Ser Val
    290                 295                 300

Ala Asn Val Ala Leu Gly Phe Pro Gln Glu Ala Val Gln Met Glu His
305                 310                 315                 320

Glu Gly Thr Gly Phe Val Ile Ser Arg Asn Ser Asp Phe Ser Ile Thr
                325                 330                 335

Ala Cys Thr Trp Thr Asn Lys Lys Trp Pro His Ser Ala Pro Glu Gly
            340                 345                 350

Lys Thr Leu Leu Arg Ala Tyr Val Gly Lys Ala Gly Asp Glu Ser Ile
            355                 360                 365

Val Glu Leu Ser Asp Asn Glu Ile Ile Lys Ile Val Leu Glu Asp Leu
    370                 375                 380

Lys Lys Val Met Lys Ile Lys Gly Glu Pro Glu Met Thr Cys Val Thr
385                 390                 395                 400

Arg Trp Asn Glu Ser Met Pro Gln Tyr His Val Gly His Lys Gln Arg
                405                 410                 415

Ile Lys Lys Val Arg Glu Ala Leu Ala Ala Ser Tyr Pro Gly Val Tyr
            420                 425                 430

Met Thr Gly Ala Ser Phe Glu Gly Val Gly Ile Pro Asp Cys Ile Asp
            435                 440                 445

Gln Gly Lys Ser Ala Val Ser Asp Val Leu Ala Tyr Leu Phe Glu
    450                 455                 460

<210> SEQ ID NO 26
<211> LENGTH: 1329
<212> TYPE: DNA
<213> ORGANISM: Xanthomonas campestris

<400> SEQUENCE: 26
atgcaaacac agcccgttat cattgccggc gccggtattg ccggactaag tatagcttac      60
gaattacagc agaaaggcat tccctatgaa atcatggagg cctcttccta tgcaggaggc     120
gttgtgaaat cattacatat tgatggttat gaactggatg ctggccctaa ttcgctggcc     180
gcatctgcag cattcatggc ttatatcgat caactgggtt tgcaggacca ggtattggaa     240
gctgcggctg ccagtaagaa ccgctttctg gtcagaaatg ataaattgca tgcagtatcg     300
ccacatccct ttaagatact gcagtcagca tatatcagtg gtgcgccaa gtggcgtctg      360 ttcacagaaa gatttcgaaa agcggccgct ccggagggag aggaaacagt atcttccttt     420
gtgacccgcc gttttggaaa ggagatcaat gactaccttt ttgaacccgt gctttctggt     480
atatatgcag gtaatcctga tctgatgtca gttggtgaag tactgcctat gctgccacaa     540
tgggagcaaa aatacggtag tgttacgcag ggactcctga agaataaagg agctatgggt     600

| | |
|---|---:|
| ggacgtaaga tcattgcctt taaaggaggt aatgcgacac tgacaaacag attgcaatcc | 660 |
| ctgcttagcg gtaagataag atttaactgt gccgtaacgg gtgtaacccg tggggcggac | 720 |
| gactatattg tacaatatac cgagaatggt aatacagcta tgctgaatgc atcccgtgtg | 780 |
| atattcacca cccctgcata cagtacagcc gtagctatac aggcacttga cgcttccctt | 840 |
| gctacacatc tcagcgatgt tccctatccc cgtatgggcg tactgcacct ggggtttgga | 900 |
| gcggaagccc ggcagaaagc accggcaggt tttggtttcc tggtgccgca tgctgcagga | 960 |
| aagcatttcc tgggcgctat ctgtaacagc gctatattcc cttcccgcgt accgacaggt | 1020 |
| aaagtgctgt ttacggtgtt cctgggtggc gcgagacaag aacagctgtt tgatcagctg | 1080 |
| gggcctgaaa agctacagca gacagtagtg aaagaactga tggaactgct gggcctgact | 1140 |
| acaccaccag aaatgcagcg ttttagtgaa tggaacagag cgattccgca actaaatgta | 1200 |
| ggttatgcac agacgaggca gcagataggc gttttgaac agcgttaccc gggcatcaga | 1260 |
| ttagcgggta actatgtgac cggagtggct gtacccgcta tcatacaggc cgcaaaaggg | 1320 |
| tactgttga | 1329 |

<210> SEQ ID NO 27
<211> LENGTH: 1347
<212> TYPE: DNA
<213> ORGANISM: Chitinophaga pinensis

<400> SEQUENCE: 27

| | |
|---|---:|
| atgtctgatc aacccgtatt gattgtcggc gccggcttat ccggattgag cattgcgtat | 60 |
| gaattgcaga aactgcaggt gccttaccag gtactggaag tttcgggtca tagcggcggc | 120 |
| gtgatgaaat cattacggaa agatggattt gaactggatg caggcgctaa tacaatcgca | 180 |
| gcttctcctg aaatactggc atacttcaca tcactgggac tggaaaatga gatattgcag | 240 |
| gccaccgctg ccagcaagca ccggttcctg gtaagacggc ggcagttgca cgctgtttct | 300 |
| cccccatcct tcaagatcat gtcgtctcct tacctgagca ggggcagtaa atggcggttg | 360 |
| tttaccgaac gttttcgcaa acctgttgtg gcaagcggag aagaaaccgt caccgatttt | 420 |
| ataacaagaa ggtttaaccg ggagatagca gaatatgtgt ttgacccggt attatccggc | 480 |
| atatatgccg gcaatcccga ccagatgagc atagcggaag tattacctgc gttgccgcgc | 540 |
| tgggagcggg aatatgggag tgttaccaaa gggctgatga agataaagg cgcaatgggc | 600 |
| ggccggaaga ttatcagttt taaggtggt aaccagttgc tcacaaaccg tttgcagcaa | 660 |
| ttgctcacta ccccggtgcg ctttaattgt aaggtaaccg gtatcaccgc atccaatggc | 720 |
| ggctatattg taagcgctgt agaagatggc gtatcagaaa gttatactgc ttcaagggtg | 780 |
| atattaacca cacctgctta cagcgcggca gcaactatta cgaatcttga tgctgctacc | 840 |
| gctgccttgt taaatgaaat tcattatccc cgtatgggcg tgctgcacct gggttttgac | 900 |
| gctactgcgt tgccgcagcc cctggatgga tttggtttcc tggtaccgaa tgctgaaaat | 960 |
| atgcatttcc tgggagcaat ctgcaacgct gcaatttcc cggataaggc gcctccggga | 1020 |
| aaaatcctct ttacggtatt cctggaggaa gcaagacagg aaagtttgtt tgaccagatg | 1080 |
| acgcccgaag ctctgcaaca gcaggtagtt tcagaggtca tgtctttact gcatttatct | 1140 |
| gcgccgccgg taatgcagca tttcagtagc tggaataaag cgattccgca gttaaatgtg | 1200 |
| ggtcatgtta agttacggcg tgccgtgaa gcttttgaaa aaaatatcc cggtattcac | 1260 |
| ctcagcggga attacctgca aggcgtagct atcccggctt tactgcaaca tgccgccgct | 1320 |

```
ttggcggctt ccctgaagaa aaattaa                                    1347
```

<210> SEQ ID NO 28
<211> LENGTH: 1413
<212> TYPE: DNA
<213> ORGANISM: Bacillus subtilis

<400> SEQUENCE: 28

```
atgagtgacg gcaaaaaaca tgtagtcatc atcggcggcg gcattaccgg tttagccgcc    60
gccttctata tggaaaaaga aatcaaagaa aagaatctgc cgcttgaact gacgcttgtt   120
gaggcaagtc cgagagtcgg cggaaaaatc cagactgtca agaaggacgg ctatatcatc   180
gaaagagggc cagactcatt tctggaacga agaaaagcg ccccgcagct tgttaaagac    240
ttaggtcttg agcatttgct tgtcaacaat gcgaccggac aatcctatgt gcttgtaaac   300
cgcactctgc atccaatgcc gaagggcgct gtaatgggga taccgacaaa aattgcgccg   360
tttgttttcta cgggtctgtt ttctttgtct ggaaggcga gagctgctat ggatttcatc   420
ctgcctgcta gcaaaacaaa ggatgatcag tcattgggag aattcttccg cagacgtgtc   480
ggagatgaag tggtcgagaa cttaatcgag ccgcttctat cagggatcta cgcaggcgac   540
attgacaagc tcagcctgat gtcgacattc ccgcaatttt atcagacgga acaaaagcat   600
agaagcctga ttctcggcat gaaaaaaaca aggcctcaag gctcaggcca gcagctgacg   660
gcaaaaaaac aagggcagtt ccagactctg tcaaccggtt tgcagaccct tgtagaagag   720
atcgaaaagc agttaaagct gacgaaggtg tataaaggca caaaagtgac caaactcagc   780
catagcggct ctggctattc gctcgaactg gataacggcg tcacacttga tgctgattca   840
gtaattgtga ctgctccgca taaagcggct gcgggaatgc tttctgagct tcctgccatt   900
tctcatttga aaaatatgca ctccacatcc gtggcaaacg tcgctttagg tttccctgaa   960
ggctccgtcc aaatggagca tgagggcacg ggttttgtca tttcaagaaa cagtgacttt  1020
gcgatcacag cctgtacgtg gacgaataaa aaatggccgc acgcagcgcc ggaaggcaaa  1080
acgctgcttc gggcatatgt cggaaaagct ggagacgaat ccattgtcga tctatcagat  1140
aatgacatta tcaacattgt gttagaagac ttaaagaaag tcatgaacat aaacggcgag  1200
ccggaaatga catgtgtcac ccgatggcat gaaagcatgc cgcagtacca tgtcggccat  1260
aagcagcgta tcaaggagct gcgtgaagca cttgcatctg cgtatccggg tgtttatatg  1320
acaggcgctt ctttcgaagg tgtcggcatt cccgactgca ttgatcaagg aaaagctgcc  1380
gtgtctgacg cgcttaccta tttattcagc taa                               1413
```

<210> SEQ ID NO 29
<211> LENGTH: 1413
<212> TYPE: DNA
<213> ORGANISM: Bacillus pumilus

<400> SEQUENCE: 29

```
atgcatgaca atcaaaaaca ccttgtcatc attggcggtg gcatcactgg tttagccgcc    60
gccttctatt tggaaaagga agtcgaggaa aaggtcttc cgattcaaat atcacttatt    120
gaagcgagcc ctaggctagg tggaaaaata caaacattat ataaagacgg ctacatcatt   180
gaacgtggac ctgattcatt tttagaaaga aggtcagtg ggccgcagct tgcaaaagat    240
gtcggtctgt ccgatcagct cgtcaataat gaaactgggc aagcgtatgt actggtcaat   300
gaaaagcttc acccgatgcc aaaaggtgct gttatgggga ttccaactca atcagcccca   360
tttattacaa ctggtctttt ttcagttgcg ggaaaagcaa gagcggcgat ggatttcgtg   420
```

```
ttgccaaaaa gcaagcagac ggaagaccag tcgcttggtg aattttttag aagacgtgtg    480
ggtgatgagg tcgttgagaa tttaattgag ccgcttctat caggcattta tgcaggggat    540
attgaccgtc tgagcttaat gtcgaccttc ccgcaatttt atcaaacaga acagcagcat    600
cgaagtttga ttcttgggat gaaaaaatca cagcagcatg cgaaagcgca gcaagtgact    660
gcgaaaaaac aaggacagtt ccaaacgatc aatcaaggat tgcagtcgct tgtggaagca    720
gtagaaggta agctcaagct gacaacggtc tataaaggga caaagtcaa acaaattgaa     780 aaaacggatg gaggctatgg cttacaatta gacagcggtc aaacgctttt tgccgattca    840
gccattgtca cgactccgca tcaatcgatt tattccatgt ttcctaaaga agcagggcta    900
gagtatttgc atgacatgac ctctacttct gttgcaacag tagcactcgg ttttaaagat    960
gaggatgttc ataatgaata tgacggcact ggatttgtca tctcaagaaa cagtgatttc   1020
tctattacgg cctgtacatg gacaaacaaa aaatggccgc atactgctcc gaaaggaaaa   1080
acgctattgc gtgcgtatgt agggaaggct ggcgacgaat caattgtcga gcagtcagac   1140
agtcaaatcg tcagcattgt gctagaagat ttaaagaaaa tcatggatat aaagcagat    1200 ccagaattga cgacagtgac tcgctggaag acaagtatgc cgcaatatca cgtcggtcat   1260
cagaaagcca tttcgaacat gcgagaaacg tttaagcaat catatcctgg tgtttatatt   1320
acaggtgctg cttttgaagg tgtcggaatc cctgattgta ttgatcaagg aaaagccgcc   1380
atctcagagg ctgtatcgta tctattttca taa                                1413
```

<210> SEQ ID NO 30
<211> LENGTH: 1413
<212> TYPE: DNA
<213> ORGANISM: Bacillus pumilus

<400> SEQUENCE: 30

```
atgcatgaca atcaaaaaca ccttgtcatc attggcggtg gcatcactgg tttagccgcc     60
gccttctatt tggaaaagga agtcgaagaa aaaggtcttc ccattcaaat atctcttatt    120
gaagcgagcc ctaggctagg tggaaaaatc caaacattat ataaagacgg ctacatcatt    180
gaacgtgggc ctgattcatt tttagaaaga aggtcagtg accgcagct ggcgaaagat      240 gtaggtctat ccgatcagct cgtcaataat gaaacagggc aggcgtatgt actagtcaat    300
gaaacccttc acccgatgcc aaaaggcgct gtcatggta ttccaactca atcagccca      360 ttcatcacaa ccggtctttt ttcagttgca ggaaaagcga gagccgcaat ggatttcgtc    420
ttgccaaaaa gcaagcaaac agaagatcag tcgctcggtg aattttttag aagacgtgtc    480
ggtgatgaag tagttgagaa tttaatcgaa cctcttctat caggcattta tgcaggtgac    540
attgaccgtc tcagcttaat gtccaccttc ccgcagtttt atcaaacaga acaaaagcat    600
cgcagtttga ttcttgggat gaaaaaatca cagcagcatg cgaaagcgca gcaagtgaca    660
gcgaaaaaac aagggcagtt ccaaacgatc aatcaaggac ttcaagcgct tgttgaagca    720
gtagaaagca agctcaagct gacaacgatt tataaaggga caaagtgaa gcagattgaa     780 aaaacagatg ggggctacgg tgtgcagtta gacagcggtc aaacgctttt ggctgattca    840
gccattgtga caactccgca tcaatcgatc tattccatgt ttccaaaaga agcggggctt    900
gagtacttgc atgatatgac atctacttct gttgcaacgg ttgcactcgg ttttaaagaa    960
gaggatgttc ataatgaata tgacggtact ggttttgtca tctcaagaaa cagtgatttc   1020
tctattacag cttgtacgtg gacgaacaaa aaatggccgc atacagctcc taaaggaaaa   1080
```

| | |
|---|---:|
| acattattgc gtgcttatgt agggaaggct ggcgacgaat caattgtcga acagtcagac | 1140 |
| catcaaatcg tcagcattgt actggaggat tgaagaaaaa ttatggatat taaagcagat | 1200 |
| ccagaactga caacagtgac tcgctggaag acgagcatgc cgcaatatca cgtcggtcat | 1260 |
| caaaaagcca tttcgaacat gcgagaaacg tttaagcaat catatcctgg tgtttatatc | 1320 |
| acaggtgctg cttttgaagg tgtcggaatc cctgattgta ttgatcaagg aaaagctgcc | 1380 |
| atttcagagg ctgtatctta tctattttca taa | 1413 |

<210> SEQ ID NO 31
<211> LENGTH: 1329
<212> TYPE: DNA
<213> ORGANISM: Artificial Sequence
<220> FEATURE:
<223> OTHER INFORMATION: Recombinant

<400> SEQUENCE: 31

| | |
|---|---:|
| atgcaaactc agcccgtcat aatagcgggc gctggcattg cgggcctttc tatcgcatac | 60 |
| gagctgcaac agaagggcat tccttacgaa attatggaag cctcgtccta cgccggaggc | 120 |
| gtggtcaagt cccttcacat tgatggctac gaactagacg ccggacctaa ttcacttgcc | 180 |
| gcgtccgctg ccttcatggc ctacatcgac caactcggac tccaagatca agtgcttgaa | 240 |
| gccgccgcag catccaagaa ccgcttcctc gtaagaaacg acaagctcca tgcagtctcg | 300 |
| ccgcacccgt ttaagatcct ccagtcggcc tacatcagtg gcggcgctaa gtggagattg | 360 |
| tttaccgaaa ggttccgcaa agctgcggct ccagagggtg aggagacagt gagcagcttc | 420 |
| gtgacgagga ggtttggcaa ggagatcaac gactacctgt tgaacccgt cttgtccggg | 480 |
| atctacgcgg gcaacccgga tttgatgagt gttggcgagg ttctgccgat gcttcctcaa | 540 |
| tgggagcaga agtacggcag cgttacacaa ggcttgttga agaataaggg cgcaatgggc | 600 |
| ggccgaaaga taatcgcttt caagggcggg aatgccacac tgaccaaccg tcttcagtca | 660 |
| ctgctctcag gaaagatccg cttcaattgc gccgtgacgg tgtcacacg aggcgcagac | 720 |
| gactacattg ttcagtacac tgagaatggc aataccgcaa tgttgaatgc aagccgcgtg | 780 |
| atcttcacaa caccgcttta ctcaactgct gttgccatcc aggcgttgga cgccagcttg | 840 |
| gccactcacc tctctgatgt accctatcct cgcatgggtg tgttgcactt gggcttcggt | 900 |
| gctgaggcaa ggcagaaggc tcctgcgggc tttgggttct tggtcccaca cgcagccgga | 960 |
| aagcacttcc tgggagcaat ctgtaactcc gctatcttcc cttcgcgggt gcccactggc | 1020 |
| aaggtgttat tcaccgtgtt cttgggcggt gccagacagg agcaactgtt tgaccagcta | 1080 |
| ggccctgaga agttacaaca gacagtggtg aaggagctta tggaattgct gggcctaact | 1140 |
| acgccgccgg agatgcaacg attctctgag tggaatcgcg caataccgca acttaatgtt | 1200 |
| ggctacgccc agactcgtca gcagattggc gtattcgagc agcgctaccc tggcatccgc | 1260 |
| ttggccggga actatgtaac tggagtggcg gtgcccgcca ttatccaagc tgcaaagggc | 1320 |
| tattgctaa | 1329 |

<210> SEQ ID NO 32
<211> LENGTH: 1347
<212> TYPE: DNA
<213> ORGANISM: Artificial Sequence
<220> FEATURE:
<223> OTHER INFORMATION: Recombinant

<400> SEQUENCE: 32

| | |
|---|---:|
| atgagcgacc agcccgtcct catcgttgga gctggtctct ccgggctctc aatcgcttac | 60 |

```
gaactacaga agctgcaagt cccttaccaa gtgctggagg tttctggaca ttctggtgga      120
gtcatgaagt cactccggaa ggacggattt gaactcgacg ctggtgccaa caccatagcc      180
gcgtctcccg agattcttgc gtactttacc tcactaggtc ttgagaatga gatcctccag      240
gcgactgctg cttctaaaca ccgcttcttg gtgcggcgaa ggcaactgca cgccgtgagc      300
ccgcacccgt tcaagatcat gtcatcgccg tacctcagcc gtggctccaa atggcggctc      360
tttactgagc ggtttcggaa gcccgtcgtc gcttcgggcg aggagaccgt caccgatttc      420
atcacgagga gattcaaccg cgaaatagcg gagtatgtgt tcgaccctgt tctaagcggg      480
atctacgccg ggaaccccga ccaaatgagt attgctgagg tgttgcctgc cttgcctagg      540
tgggaaaggg agtacggatc agtgaccaag ggccttatga aggataaggg tgcgatggga      600
ggtcgaaaga tcatcagctt taagggtggc aaccagctac ttacaaaccg cttacagcag      660
ctactcacta ctccggtgag attcaattgc aaggtgacag ggattacagc cagcaatggc      720
gggtacatcg tgagcgctgt tgaggacggc gtatctgaga gctacaccgc atctcgtgtg      780
atcttgacca cacccgctta ctcagcagcg gctaccataa ctaaccttga tgcagccact      840
gcggcactgt tgaacgaaat ccattatcca cgtatgggcg tgttacactt gggctttgat      900
gcaactgcct tgccacagcc gctggacggg ttcggatttc tagtgccgaa cgcggagaac      960
atgcacttcc tgggagccat ctgcaatgca gccatcttcc cggacaaggc tccgcccggc     1020
aagatcctgt ttacagtgtt cctcggaggc gcacgccagg agtcgctctt cgatcagatg     1080
actcctgagg ctcttcagca gcaagtcgtt agtgaggtga tgagcttgtt gcacttgtca     1140
gctccaccgg tgatgcagca cttctcctcc tggaacaagg ccatccctca attgaacgtc     1200
gggcacgtga agttgcggcg cgcggtagag gcgttcgaga agaaataccc tggaatccat     1260
ctctcgggca actacctcca gggagttgca ataccagctt tactccagca cgccgcagct     1320
ttagctgctt ctcttaagaa gaactga                                         1347

<210> SEQ ID NO 33
<211> LENGTH: 1413
<212> TYPE: DNA
<213> ORGANISM: Artificial Sequence
<220> FEATURE:
<223> OTHER INFORMATION: Recombinant

<400> SEQUENCE: 33
atgtcggatg gcaagaagca cgtcgtcatc ataggcggtg ggatcactgg cttggccgct       60
gcattctaca tggagaagga gattaaggag aagaacctcc cacttgagct gacgctagtt      120
gaggccagtc ccagggtcgg cggcaagatc cagacggtca agaaggacgg gtacataatt      180
gaacgcggcc ctgacagctt cttagagcgc aagaaatcgg ctccgcagct agttaaggac      240
ttgggacttg agcacctgct cgtcaacaac gcgaccggac agtcgtacgt gctcgtgaac      300
cggacgctcc acccgatgcc gaagggcgct gtgatgggca ttcgaccaa gatagcacca      360 tcgtgagta ccggcctatt cagcctttcc ggcaaggcaa gggctgcgat ggacttcatc      420
ttgcctgcct ctaagactaa ggacgatcag tccttgggcg agttcttccg ccgccgggtg      480
ggtgatgagg tggtggagaa cttaattgag ccgctcctat ctggaatcta cgctggtgac      540
atcgacaaac tgtctctgat gtccacccttt ccgcagttct accaaactga gcagaagcac      600
cgttcactta tcttgggaat gaagaagact agacctcaag gttcgggtca gcaactgacg      660
gccaagaaac agggtcagtt ccagacgcta agcaccgggc ttcagacact cgtggaggag      720
```

| | |
|---|---|
| attgagaaac agctcaaact tactaaggtg tacaagggca cgaaggtgac aaagttatcc | 780 |
| cactccggca gcgggtactc cctggagttg acaatggcg taacgttgga cgccgactca | 840 |
| gttatcgtga cagcgccgca taaggctgct gccgggatgt tgtcagaact cccggcgatt | 900 |
| tcccatctca agaacatgca cagtacctcg gttgccaacg tcgccctcgg attcccggaa | 960 |
| ggaagtgttc aaatggagca cgaaggcacg ggtttcgtaa tttccaggaa ctccgacttt | 1020 |
| gccatcaccg cttgtacttg gaccaacaag aagtggcctc atgctgcgcc ggagggcaag | 1080 |
| acattgctca gagcttacgt cgggaaggcg ggcgacgagt caatcgtcga tcttagcgac | 1140 |
| aacgacatca ttaacattgt gctggaggac ttgaagaagg ttatgaacat caatggcgag | 1200 |
| ccagagatga cctgcgtgac ccgatggcac gagtctatgc cgcagtacca cgtcggtcac | 1260 |
| aagcagcgca tcaaggagtt gcgcgaggca ctcgcctcag cttaccctgg cgtgtacatg | 1320 |
| actggcgctt cgtttgaggg cgttggtatt cctgactgca tcgaccaggg aaaggcggcc | 1380 |
| gtcagtgacg cgctcaccta cctcttcagt tga | 1413 |

<210> SEQ ID NO 34
<211> LENGTH: 1413
<212> TYPE: DNA
<213> ORGANISM: Artificial Sequence
<220> FEATURE:
<223> OTHER INFORMATION: Recombinant

<400> SEQUENCE: 34

| | |
|---|---|
| atgcacgaca accagaagca cctggtcata atcggaggcg gcataaccgg ccttgctgcg | 60 |
| gccttctacc tggagaagga ggtcgaggag aagggtctcc ctatccagat ttcattgatt | 120 |
| gaggcttcgc ctcggctggg agggaagatc cagacattgt acaaggacgg gtacatcatc | 180 |
| gagcgtggtc cagacagttt cctggagcgg aaggtcagcg gaccgcagct cgccaaggac | 240 |
| gtgggactta gcgaccaact ggtgaacaac gagacaggac aggcgtacgt cttggtgaat | 300 |
| gagaagttgc acccgatgcc taagggtgcc gtgatgggca tcccaacgca aatctcacct | 360 |
| ttcatcacca ccggactctt ctccgtggcc ggaaaggcac gagctgcaat ggacttcgtt | 420 |
| ctgcctaagt cgaaacagac cgaagaccag tctctaggcg agttcttccg ccgccgtgtg | 480 |
| ggtgacgagg ttgtggagaa cctcatcgag cctttgttgt ctgggatcta cgcgggcgac | 540 |
| atcgacagac ttagtctcat gagtaccttt ccgcaattct atcagacaga acagcagcat | 600 |
| cgaagtctca tactcgggat gaagaagtca caacaacatg caaaggccca gcaagttacc | 660 |
| gccaagaaac agggccagtt ccaaacgatc aaccagggcc tccagagctt ggtggaggca | 720 |
| gtggagggaa agttgaagct caccaccgtt tacaaaggga caaggttaa acagattgag | 780 |
| aagacggacg gcggttacgg gttacaattg gactccggac agactctctt cgctgattcc | 840 |
| gctatcgtaa ctactcctca ccagagcatc tactctatgt tcccgaagga ggcgggcctg | 900 |
| gagtacctgc acgacatgac ttcaacgtct gtcgccaccg tggctttggg cttcaaggac | 960 |
| gaggacgtcc acaatgagta tgacgggacg ggattcgtta tcagtaggaa ctccgacttc | 1020 |
| agcatcaccg cctgcacgtg gaccaacaag aagtggccac acaccgcgcc caaagggaag | 1080 |
| acccttctga gggcatacgt gggcaaggcg ggcgacgaga gcatcgtcga gcaatctgat | 1140 |
| tctcagattg tttcaatcgt cctcgaagac tcaagaaga tcatggacat caaggcagac | 1200 |
| ccggaactta ccaccgttac tcgatggaag acctcgatgc ctcagtatca cgtcgggcac | 1260 |
| cagaaggcaa tcagcaacat gagggagaca ttcaagcagt cgtatcctgg cgtgtacatt | 1320 |
| accggagcag cattcgaagg cgtaggaatc cctgactgca ttgaccaggg caaggctgct | 1380 | atctcagagg ccgtgtccta tctcttctcg tga                                    1413

<210> SEQ ID NO 35
<211> LENGTH: 1413
<212> TYPE: DNA
<213> ORGANISM: Artificial Sequence
<220> FEATURE:
<223> OTHER INFORMATION: Recombinant

<400> SEQUENCE: 35
atgcacgaca accagaagca cctggtgata attggaggcg ggattaccgg cctagcagcc        60
gctttctatc tggagaagga ggtggaggag aagggcctcc cgatacagat ttcgctgatt      120
gaagcctctc cgcgcctggg cggcaagatc agacattgt acaaggacgg gtacatcatt       180
gagcgcgggc ctgactcgtt cctggagcgg aaggtctccg gtcctcaact ggccaaagac      240
gtgggtcttt ccgatcagct tgtgaacaat gagaccggtc aggcttacgt cttggtcaac      300
gaaactctgc atcccatgcc taagggagcc gttatgggca ttccaacgca aatctctccg      360
ttcataacga ctgggctgtt cagcgttgcg ggcaaagcaa gggctgctat ggacttcgtg      420
ctgccaaaga gtaagcagac cgaggaccag tccctcggcg agttcttccg ccgccgagtg      480
ggcgatgagg tggttgagaa tctaatcgaa ccgctgttgt cgggcatcta tgcgggcgac      540
atcgacaggc taagtcttat gtccactttc cctcagttct accagacaga gcagaaacac      600
aggagtctca tccttggaat gaagaagtcc cagcagcacg cgaaggctca gcaagtgacc      660
gccaagaagc aaggacagtt ccagaccatc aaccagggcc tacaggccct tgtcgaagcc      720
gttgagtcga gttaaagtt gacgacgatc tacaagggca ccaaggtgaa gcagattgag      780
aagactgacg gtggctatgg tgtgcaactc gattcgggcc aaacattgct cgctgactcc      840
gctatcgtca cgacgccaca ccagtcgatc tactcgatgt tcccgaagga ggcgggccta      900
gagtaccttc acgacatgac ctccacttcg gtcgccaccg ttgcactcgg ctttaaggag      960
gaggacgttc acaacgagta cgatggcacc ggattcgtga tctccaggaa ctcggacttc     1020
tcgattaccg cgtgcacgtg gacaaataag aagtggccgc acacagcgcc aaagggcaag     1080
acccttctgc gggcgtatgt gggcaaggcc ggtgacgaga gcattgtcga acaatctgac     1140
catcagatcg tttctattgt tcttgaggat ctcaagaaga taatggacat taaggccgac     1200
cctgagctta ccacagtgac gaggtggaag acctcgatgc cgcagtatca cgtagggcac     1260
cagaaggcca tctccaacat gcgggagaca ttcaagcagt cgtaccctgg cgtgtacatt     1320
actggcgctg ctttcgaggg cgttggcatc ccggactgca tcgaccaggg caaggccgca     1380
atctcagagg cagtgtcgta cctgttcagc tag                                  1413

<210> SEQ ID NO 36
<211> LENGTH: 1320
<212> TYPE: DNA
<213> ORGANISM: Artificial Sequence
<220> FEATURE:
<223> OTHER INFORMATION: Recombinant

<400> SEQUENCE: 36
cagcccgtca taatagcggg cgctggcatt gcgggccttt ctatcgcata cgagctgcaa        60
cagaagggca ttccttacga aattatggaa gcctcgtcct acgccggagg cgtggtcaag      120
tcccttcaca ttgatggcta cgaactagac gccggaccta attcacttgc cgcgtccgct      180
gccttcatgg cctacatcga ccaactcgga ctccaagatc aagtgcttga agccgccgca      240

```
gcatccaaga accgcttcct cgtaagaaac gacaagctcc atgcagtctc gccgcacccg      300
tttaagatcc tccagtcggc ctacatcagt ggcggcgcta agtggagatt gtttaccgaa      360
aggttccgca aagctgcggc tccagagggt gaggagacag tgagcagctt cgtgacgagg      420
aggtttggca aggagatcaa cgactacctg tttgaacccg tcttgtccgg gatctacgcg      480
ggcaacccgg atttgatgag tgttggcgag gttctgccga tgcttcctca atgggagcag      540
aagtacggca gcgttacaca aggcttgttg aagaataagg gcgcaatggg cggccgaaag      600
ataatcgctt tcaagggcgg gaatgccaca ctgaccaacc gtcttcagtc actgctctca      660
ggaaagatcc gcttcaattg cgccgtgacg ggtgtcacac gaggcgcaga cgactacatt      720
gttcagtaca ctgagaatgg caataccgca atgttgaatg caagccgcgt gatcttcaca      780 acaccegctt actcaactgc tgttgccatc caggcgttgg acgccagctt ggccactcac      840
ctctctgatg taccctatcc tcgcatgggt gtgttgcact gggcttcgg tgctgaggca      900 aggcagaagg ctcctgcggg cttttgggttc ttggtcccac acgcagccgg aaagcacttc      960
ctgggagcaa tctgtaactc cgctatcttc ccttcgcggg tgcccactgg caaggtgtta    1020
ttcaccgtgt tcttgggcgg tgccagacag gagcaactgt ttgaccagct aggccctgag    1080
aagttacaac agacagtggt gaaggagctt atggaattgc tgggcctaac tacgccgccg    1140
gagatgcaac gattctctga gtggaatcgc gcaataccgc aacttaatgt tggctacgcc    1200
cagactcgtc agcagattgg cgtattcgag cagcgctacc ctggcatccg cttggccggg    1260
aactatgtaa ctggagtggc ggtgcccgcc attatccaag ctgcaaaggg ctattgctaa    1320
```

<210> SEQ ID NO 37
<211> LENGTH: 1338
<212> TYPE: DNA
<213> ORGANISM: Artificial Sequence
<220> FEATURE:
<223> OTHER INFORMATION: Recombinant

<400> SEQUENCE: 37

```
cagcccgtcc tcatcgttgg agctggtctc tccgggctct caatcgctta cgaactacag       60
aagctgcaag tcccttacca agtgctggag gtttctggac attctggtgg agtcatgaag      120
tcactccgga aggacggatt tgaactcgac gctggtgcca acaccatagc cgcgtctccc      180
gagattcttg cgtactttac ctcactaggt cttgagaatg agatcctcca ggcgactgct      240
gcttctaaac accgcttctt ggtgcggcga aggcaactgc acgccgtgag cccgcacccg      300
ttcaagatca tgtcatcgcc gtacctcagc cgtggctcca aatggcggct ctttactgag      360
cggtttcgga agcccgtcgt cgcttcgggc gaggagaccg tcaccgattt catcacgagg      420
agattcaacc gcgaaatagc ggagtatgtg ttcgaccctg ttctaagcgg gatctacgcc      480
gggaacccgg accaaatgag tattgctgag gtgttgcctg ccttgcctag gtgggaaagg      540
gagtacggat cagtgaccaa gggccttatg aaggataagg gtgcgatggg aggtcgaaag      600
atcatcagct ttaagggtgg caaccagcta cttacaaacc gcttacagca gctactcact      660
actccggtga gattcaattg caaggtgaca gggattacag ccagcaatgg cgggtacatc      720
gtgagcgctg ttgaggacgg cgtatctgag agctacaccg catctcgtgt gatcttgacc      780
acacccgctt actcagcagc ggctaccata actaaccttg atgcagccac tgcggcactg      840
ttgaacgaaa tccattatcc acgtatgggc gtgttacact gggctttga tgcaactgcc      900 ttgccacagc cgctgacgg gttcggattt ctagtgccga acgcggagaa catgcacttc      960
ctgggagcca tctgcaatgc agccatcttc ccggacaagg ctccgcccgg caagatcctg    1020
```

```
tttacagtgt tcctcggagg cgcacgccag gagtcgctct tcgatcagat gactcctgag    1080
gctcttcagc agcaagtcgt tagtgaggtg atgagcttgt tgcacttgtc agctccaccg    1140
gtgatgcagc acttctcctc ctggaacaag gccatccctc aattgaacgt cgggcacgtg    1200
aagttgcggc gcgcgtaga ggcgttcgag aagaaatacc ctggaatcca tctctcgggc     1260
aactacctcc agggagttgc aataccagct ttactccagc acgccgcagc tttagctgct    1320
tctcttaaga agaactga                                                   1338

<210> SEQ ID NO 38
<211> LENGTH: 1344
<212> TYPE: DNA
<213> ORGANISM: Artificial Sequence
<220> FEATURE:
<223> OTHER INFORMATION: Recombinant

<400> SEQUENCE: 38
atgagcgacc aacccgtcct catcgttgga gctggtctct ccgggctctc aatcgcttac      60
gaactacaga agctgcaagt cccttaccaa gtgctggagg tttctggaca ttctggtgga    120
gtcatgaagt cactccggaa ggacggattt gaactgacg ctggtgccaa caccatagcc     180
acgtctcccg agattcttgc gtactttacc tcactaggtc ttgagaatga gatcctccag    240
gcgactgcta cttctaaaca ccgcttcttg gtgcggcgaa ggcaactgca cgccgtgagc    300
ccgcacccgt tcaagatcat gtcatcgccg tacctctgcc gtggctccaa atggaggctc    360
tttactgagc ggtttcggaa acccgtcgtc gcttcgggcg aggagaccgt caccgatttc    420
atcacgagga gattcaaccg cgaaatagcg gagtatgtgt tcgaccctgt tctaagtggg    480
atctacgccg ggaaccccga ccaaatgagt attgctgagg tgttgcctgc cttgcctagg    540
tgggaaaggg agtacggatc agtgaccaag ggccttatga aggataaggg tgcgatggga    600
ggtcgaaaga tcatcagctt taagggtggc aaccagctac ttacaaaccg cttacagcag    660
ctactcacta ctccggtgag attcaattgc aaggtgacag ggattacagc cagcaatggc    720
gggtacatcg tgagcgctgt tgaggacggc gtatctgaga gctacaccgc atctcgtgtg    780
atcttgacca caccgcttta ctcagcagcg gctaccataa ctaaccttga tgcagccact    840
gcggcactgt tgaacgaaat ccattatcca cgtatgggcg tgttacactt gggctttgat    900
gcaactgcct tgccacagcc gctggacggg ttcggatttc tagtgccgaa cgcggagaac    960
atgcacttcc tgggagccat ctgcaatgca gccatcttcc cggacaaggc tccgcccggc   1020
aagatcctgt ttacagtgtt cctcggaggc gcacgccagg agtcgctctt cgatcagatg   1080
actcctgagg ctcttcagca gcaagtcgtt agtgaggtga tgagcttgtt gcacttgtca   1140
gctccaccgg tgatgcagca cttctcctcc tggaacaagg ccatccctca attgaacgtc   1200
gggcacgtga agttgcggcg cgcggtagag gcgttcgaga agaaataccc tggaatccat   1260
ctctcgggca actacctcca gggagttgca ataccagctt tactccagca cgccgcagct   1320
ttagctgctt ctcttaagaa gaac                                           1344

<210> SEQ ID NO 39
<211> LENGTH: 1338
<212> TYPE: DNA
<213> ORGANISM: Artificial Sequence
<220> FEATURE:
<223> OTHER INFORMATION: Recombinant

<400> SEQUENCE: 39
```

```
cagcccgtcc tcatcgttgg agctggtctc tccgggctct caatcgctta cgaactacag    60
aagctgcaag tcccttacca agtgctggag gtttctggac attctggtgg agtcatgaag   120
tcactccgga aggacggatt tgaactcgac gctggtgcca acaccatagc cacgtctccc   180
gagattcttg cgtactttac ctcactaggt cttgagaatg agatcctcca ggcgactgct   240
acttctaaac accgcttctt ggtgcggcga aggcaactgc acgccgtgag cccgcacccg   300
ttcaagatca tgtcatcgcc gtacctctgc cgtggctcca aatggaggct ctttactgag   360
cggtttcgga aacccgtcgt cgcttcgggc gaggagaccg tcaccgattt catcacgagg   420
agattcaacc gcgaaatagc ggagtatgtg ttcgaccctg ttctaagtgg gatctacgcc   480
gggaacccgg accaaatgag tattgctgag gtgttgcctg ccttgcctag gtgggaaagg   540
gagtacggat cagtgaccaa gggccttatg aaggataagg gtgcgatggg aggtcgaaag   600
atcatcagct ttaagggtgg caaccagcta cttacaaacc gcttacagca gctactcact   660
actccggtga gattcaattg caaggtgaca gggattacag ccagcaatgg cgggtacatc   720
gtgagcgctg ttgaggacgg cgtatctgag agctacaccg catctcgtgt gatcttgacc   780
acacccgctt actcagcagc ggctaccata actaaccttg atgcagccac tgcggcactg   840
ttgaacgaaa tccattatcc acgtatgggc gtgttacact tgggctttga tgcaactgcc   900
ttgccacagc cgctggacgg gttcggattt ctagtgccga acgcggagaa catgcacttc   960
ctgggagcca tctgcaatgc agccatcttc ccggacaagg ctccgcccgg caagatcctg  1020
tttacagtgt cctcggagg cgcacgccag gagtcgctct tcgatcagat gactcctgag  1080
gctcttcagc agcaagtcgt tagtgaggtg atgagcttgt tgcacttgtc agctccaccg  1140
gtgatgcagc acttctcctc ctggaacaag gccatccctc aattgaacgt cgggcacgtg  1200
aagttgcggc gcgcgtaga ggcgttcgag aagaaatacc ctggaatcca tctctcgggc  1260
aactacctcc agggagttgc aataccagct ttactccagc acgccgcagc tttagctgct  1320
tctcttaaga agaactga                                                 1338

<210> SEQ ID NO 40
<211> LENGTH: 1338
<212> TYPE: DNA
<213> ORGANISM: Artificial Sequence
<220> FEATURE:
<223> OTHER INFORMATION: Recombinant

<400> SEQUENCE: 40
cagcccgtcc tcatcgttgg agctggtctc tccgggctct caatcgctta cgaactacag    60
aagctgcaag tcccttacca agtgctggag gtttctggac attctggtgg agtcatgaag   120
tcactccgga aggacggatt tgaactcgac gctggtgcca acaccatagc cacgtctccc   180
gagattcttg cgtactttac ctcactaggt cttgagaatg agatcctcca ggcgactgct   240
gcttctaaac accgcttctt ggtgcggcga aggcaactgc acgccgtgag cccgcacccg   300
ttcaagatca tgtcatcgcc gtacctcagc cgtggctcca aatggcggct ctttactgag   360
cggtttcgga agcccgtcgt cgcttcgggc gaggagaccg tcaccgattt catcacgagg   420
agattcaacc gcgaaatagc ggagtatgtg ttcgaccctg ttctaagcgg gatctacgcc   480
gggaacccgg accaaatgag tattgctgag gtgttgcctg ccttgcctag gtgggaaagg   540
gagtacggat cagtgaccaa gggccttatg aaggataagg gtgcgatggg aggtcgaaag   600
atcatcagct ttaagggtgg caaccagcta cttacaaacc gcttacagca gctactcact   660
actccggtga gattcaattg caaggtgaca gggattacag ccagcaatgg cgggtacatc   720
```

```
gtgagcgctg ttgaggacgg cgtatctgag agctacaccg catctcgtgt gatcttgacc    780 acaccgctt actcagcagc ggctaccata actaaccttg atgcagccac tgcggcactg     840
ttgaacgaaa tccattatcc acgtatgggc gtgttacact tgggctttga tgcaactgcc    900
ttgccacagc cgctggacgg gttcggattt ctagtgccga acgcggagaa catgcacttc    960
ctgggagcca tctgcaatgc agccatcttc ccggacaagg ctccgcccgg caagatcctg   1020
tttacagtgt cctcggagg cgcacgccag gagtcgctct tcgatcagat gactcctgag    1080
gctcttcagc agcaagtcgt tagtgaggtg atgagcttgt tgcacttgtc agctccaccg   1140
gtgatgcagc acttctcctc ctggaacaag gccatccctc aattgaacgt cgggcacgtg   1200
aagttgcggc gcgcggtaga ggcgttcgag aagaaatacc ctggaatcca tctctcgggc   1260
aactacctcc agggagttgc aataccagct ttactccagc acgccgcagc tttagctgct   1320
tctcttaaga agaactga                                                 1338
```

<210> SEQ ID NO 41
<211> LENGTH: 1338
<212> TYPE: DNA
<213> ORGANISM: Artificial Sequence
<220> FEATURE:
<223> OTHER INFORMATION: Recombinant

<400> SEQUENCE: 41

```
cagcccgtcc tcatcgttgg agctggtctc tccgggctct caatcgctta cgaactacag     60
aagctgcaag tcccttacca agtgctggag gtttctggac attctggtgg agtcatgaag    120
tcactccgga aggacggatt tgaactcgac gctggtgcca acaccatagc cacgtctccc    180
gagattcttg cgtactttac ctcactaggt cttgagaatg agatcctcca ggcgactgct    240
acttctaaac accgcttctt ggtgcggcga aggcaactgc acgccgtgag cccgcacccg    300
ttcaagatca tgtcatcgcc gtacctctgc cgtggctcca aatggaggct ctttactgag    360
cggtttcgga aacccgtcgt cgcttcgggc gaggagaccg tcaccgattt catcacgagg    420
agattcaacc gcgaaatagc ggagtatgtg ttcgaccctg ttctaagtgg gatctacgcc    480
gggaacccgg accaaatgag tattgctgag gtgttgcctg ccttgcctag gtgggaaagg    540
gagtacggat cagtgaccaa gggccttatg aaggataagg gtgcgatggg aggtcgaaag    600
atcatcagct ttaagggtgg caaccagcta cttacaaacc gcttacagca gctactcact    660
actccggtga gattcaattg caaggtgaca gggattacag ccagcaatgg cgggtacatc    720
gtgagcgctg ttgaggacgg cgtatctgag agctacaccg catctcgtgt gatcttgacc    780 acaccgctt actcagcagc ggctaccata actaaccttg atgcagccac tgcggcactg     840
ttgaacgaaa tccattatcc acgtatgggc gtattacact tgggctttga tgcaactgcc    900
ttgccacagc cgctggacgg gttcggattt ctagtgccga acgcggagaa catgcacttc    960
ctgggagcca tctgcaatgc agccatcttc ccggacaagg ctccgcccgg caagatcctg   1020
tttacagtgt cctcggagg cgcacgccag gagtcgctct tcgatcagat gactcctgag    1080
gctcttcagc agcaagtcgt tagtgaggtg atgagcttgt tgcacttgtc agctccaccg   1140
gtgatgcagc acttctcctc ctggaacaag gccatccctc aattgaacgt cgggcacgtg   1200
aagttgcggc gcgcggtaga ggcgttcgag aagaaatacc ctggaatcca tctctcgggc   1260
aactacctcc agggagttgc aataccagct ttactccagc acgccgcagc tttagctgct   1320
tctcttaaga agaactga                                                 1338
```

<210> SEQ ID NO 42
<211> LENGTH: 1338
<212> TYPE: DNA
<213> ORGANISM: Artificial Sequence
<220> FEATURE:
<223> OTHER INFORMATION: Recombinant

<400> SEQUENCE: 42

| | | | | | |
|---|---|---|---|---|---|
| cagcccgtcc | tcatcgttgg | agctggtctc | tccgggctct | caatcgctta | cgaactacag | 60 |
| aagctgcaag | tcccttacca | agtgctggag | gtttctggac | attctggtgg | agtcatgaag | 120 |
| tcactccgga | aggacggatt | tgaactcgac | gctggtgcca | acaccatagc | cacgtctccc | 180 |
| gagattcttg | cgtactttac | ctcactaggt | cttgagaatg | agatcctcca | ggcgactgct | 240 |
| acttctaaac | accgcttctt | ggtgcggcga | aggcaactgc | acgccgtgag | cccgcacccg | 300 |
| ttcaagatca | tgtcatcgcc | gtacctctgc | cgtggctcca | aatggaggct | ctttactgag | 360 |
| cggtttcgga | aacccgtcgt | cgcttcgggc | gaggagaccg | tcaccgattt | catcacgagg | 420 |
| agattcaacc | gcgaaatagc | ggagtatgtg | ttcgaccctg | ttctaagtgg | gatctacgcc | 480 |
| gggaacccgg | accaaatgag | tattgctgag | gtgttgcctg | ccttgcctag | gtgggaaagg | 540 |
| gagtacggat | cagtgaccaa | gggccttatg | aaggataagg | gtgcgatggg | aggtcgaaag | 600 |
| atcatcagct | ttaagggtgg | caaccagcta | cttacaaacc | gcttacagca | gctactcact | 660 |
| actccggtga | gattcaatta | caaggtgaca | gggattacag | ccagcaatgg | cgggtacatc | 720 |
| gtgagcgctg | ttgaggacgg | cgtatctgag | agctacaccg | catctcgtgt | gatcttgacc | 780 |
| acacccgctt | actcagcagc | ggctaccata | actaaccttg | atgcagccac | tgcggcactg | 840 |
| ttgaacgaaa | tccattatcc | acgtatgggc | gtgttacact | gggctttga | tgcaactgcc | 900 |
| ttgccacagc | cgctggacgg | gttcggattt | ctagtgccga | acgcggagaa | catgcacttc | 960 |
| ctgggagcca | tctgcaatgc | agccatcttc | ccggacaagg | ctccgcccgg | caagatcctg | 1020 |
| tttacagtgt | tcctcggagg | cgcacgccag | gagtcgctct | tcgatcagat | gactcctgag | 1080 |
| gctcttcagc | agcaagtcgt | tagtgaggtg | atgagcttgt | tgcacttgtc | agctccaccg | 1140 |
| gtgatgcagc | acttctcctc | ctggaacaag | gccatccctc | aattgaacgt | cgggcacgtg | 1200 |
| aagttgcggc | gcgcggtaga | ggcgttcgag | aagaaatacc | ctggaatcca | tctctcgggc | 1260 |
| aactacctcc | agggagttgc | aataccagct | ttactccagc | acgccgcagc | tttagctgct | 1320 |
| tctcttaaga | agaactga | | | | | 1338 |

<210> SEQ ID NO 43
<211> LENGTH: 1338
<212> TYPE: DNA
<213> ORGANISM: Artificial Sequence
<220> FEATURE:
<223> OTHER INFORMATION: Recombinant

<400> SEQUENCE: 43

| | | | | | |
|---|---|---|---|---|---|
| cagcccgtcc | tcatcgttgg | agctggtctc | tccgggctct | caatcgctta | cgaactacag | 60 |
| aagctgcaag | tcccttacca | agtgctggag | gtttctggac | attctggtgg | agtcatgaag | 120 |
| tcactccgga | aggacggatt | tgaactcgac | gctggtgcca | acaccatagc | cacgtctccc | 180 |
| gagattcttg | cgtactttac | ctcactaggt | cttgagaatg | agatcctcca | ggcgactgct | 240 |
| acttctaaac | accgcttctt | ggtgcggcga | aggcaactgc | acgccgtgag | cccgcacccg | 300 |
| ttcaagatca | tgtcatcgcc | gtacctctgc | cgtggctcca | aatggaggct | ctttactgag | 360 |
| cggtttcgga | aacccgtcgt | cgcttcgggc | gaggagaccg | tcaccgattt | catcacgagg | 420 |

```
agattcaacc gcgaaatagc ggagtatgtg ttcgaccctg ttctaagtgg gatctacgcc    480
gggaacccgg accaaatgag tattgctgag gtgttgcctg ccttgcctag gtgggaaagg    540
gagtacggat cagtgaccaa gggccttatg aaggataagg gtgcgatggg aggtcgaaag    600
atcatcagct ttaagggtgg caaccagcta cttacaaacc gcttacagca gctactcact    660
actccggtga gattcaattg caaggtgaca gggattacag ccagcaatgg cgggtacatc    720
gtgagcgctg ttgaggacgg cgtatctgag agctacaccg catctcgtgt gatcttgacc    780
acaccgcatt actcagcagc ggctaccata actaaccttg atgcagccac tgcggcactg    840
ttgaacgaaa tccattatcc acgtatgggc gtgttacact gggctttga tgcaactgcc    900 ttgccacagc cgctggacgg gttcggattt ctagtgccga acgcggagaa catgcacttc    960
ctgggagcca tctgcaatgc agccatcttc ccggacaagg ctccgcccgg caagatcctg   1020
tttacagtgt tcctcggagg cgcacgccag gagtcgctct tcgatcagat gactcctgag   1080
gctcttcagc agcaagtcgt tagtgaggtg atgagcttgt tgcacttgtc agctccaccg   1140
gtgatgcagc acttctcctc ctggaacaag gccatccctc aattgaacgt cgggcacgtg   1200
aagttgcggc gcgcggtaga ggcgttcgag aagaaatacc ctggaatcca tctctcgggc   1260
aactacctcc agggagttgc aataccagct ttactccagc acgccgcagc tttagctgct   1320
tctcttaaga agaactga                                                 1338
```

<210> SEQ ID NO 44
<211> LENGTH: 1338
<212> TYPE: DNA
<213> ORGANISM: Artificial Sequence
<220> FEATURE:
<223> OTHER INFORMATION: Recombinant

<400> SEQUENCE: 44

```
cagcccgtcc tcatcgttgg agctggtctc tccgggctct caatcgctta cgaactacag     60
aagctgcaag tcccttacca agtgctggag gtttctggac attctggtgg agtcatgaag    120
tcactccgga aggacggatt tgaactcgac gctggtgcca acaccatagc cacgtctccc    180
gagattcttg cgtactttac ctcactaggt cttgagaatg agatcctcca ggcgactgct    240
acttctaaac accgcttctt ggtgcggcga aggcaactgc acgccgtgag cccgcacccg    300
ttcaagatca tgtcatcgcc gtacctctgc cgtggctcca aatggaggct ctttactgag    360
cggtttcgga aacccgtcgt cgcttcgggc gaggagaccg tcaccgattt catcacgagg    420
agattcaacc gcgaaatagc ggagtatgtg ttcgaccctg ttctaagtgg gatctacgcc    480
gggaacccgg accaaatgag tattgctgag gtgttgcctg ccttgcctag gtgggaaagg    540
gagtacggat cagtgaccaa gggccttatg aaggataagg gtgcgatggg aggtcgaaag    600
atcatcagct ttaagggtgg caaccagcta cttacaaacc gcttacagca gctactcact    660
actccggtga gattcaattg caaggtgaca gggattacag ccagcaatgg cgggtacatc    720
gtgagcgctg ttgaggacgg cgtatctgag agctacaccg catctcgtgt gatcttgacc    780
acaccgcatt actcagcagc ggctaccata actaaccttg atgcagccac tgcggcactg    840
ttgaacgaaa tccattatcc acgtatgggc gtgttacact gggctttga tgcaactgcc    900 ttgccacagc cgctggacgg gttcggattt ctagtgccga acgcggagaa catgcacttc    960
ctgggagcca tctgcaatgc agccatcttc ccggacaagg ctccgcccgg caagatcctg   1020
tttacagtgt tcctcggagg cgcacgccag gagtcgctct tcgatcagat gactcctgag   1080
```

```
gctcttcagc agcaagtcgt tagtgaggtg atgagcttgt tgcacttgtc agctccaccg   1140
gtgatgcagc acttctcctc ctggaacaag gccatccctc aattgaacgt cgggcacgtg   1200
aagttgcggc gcgcggtaga ggcgttcgag aagaaatacc ctggaatcca tctctcgggc   1260
aactacctcc agggagttgc aataccagct ttactccagc acgccgcagc tttagctgct   1320
tctcttaaga agaactga                                                1338
```

<210> SEQ ID NO 45
<211> LENGTH: 1338
<212> TYPE: DNA
<213> ORGANISM: Artificial Sequence
<220> FEATURE:
<223> OTHER INFORMATION: Recombinant

<400> SEQUENCE: 45

```
cagcccgtcc tcatcgttgg agctggtctc tccgggctct caatcgctta cgaactacag     60
aagctgcaag tcccttacca agtgctgagg gtttctggac attctggtgg agtcatgaag   120
tcactccgga aggacggatt tgaactcgac gctggtgcca acaccatagc cacgtctccc   180
gagattcttg cgtactttac ctcactaggt cttgagaatg agatcctcca ggcgactgct   240
acttctaaac accgcttctt ggtgcggcga aggcaactgc acgccgtgag cccgcacccg   300
ttcaagatca tgtcatcgcc gtacctctgc cgtggctcca aatggaggct ctttactgag   360
cggtttcgga aacccgtcgt cgcttcgggc gaggagaccg tcaccgattt catcacgagg   420
agattcaacc gcgaaatagc ggagtatgtg ttcgaccctg ttctaagtgg gatctacgcc   480
gggaacccgg accaaatgag tattgctgag gtgttgcctg ccttgcctag gtgggaaagg   540
gagtacggat cagtgaccaa gggccttatg aaggataagg gtgcgatggg aggtcgaaag   600
atcatcagct ttaagggtgg caaccagcta cttacaaacc gcttacagca gctactcact   660
actccggtga gattcaattg caaggtgaca gggattacag ccagcaatgg cgggtacatc   720
gtgagcgctg ttgaggacgg cgtatctgag agctacaccg catctcgtgt gatcttgacc   780 acaccegctt actcagcagc ggctaccata actaaccttg atgcagccac tgcggcactg   840
ttgaacgaaa tccattatcc acgtatgggc gtgttacact tgggctttga tgcaactgcc   900
ttgccacagc cgctggacgg gttcggattt ctagtgccga acgcggagaa catgcacttc   960
ctgggagcca tctgcaatgc agccatcttc ccggacaagg ctccgcccgg caagatcctg   1020
tttacagtgt tcctcggagg cgcacgccag gagtcgctct tcgatcagat gactcctgag   1080
gctcttcagc agcaagtcgt tagtgaggtg atgagcttgt tgcacttgtc agctccaccg   1140
gtgatgcagc acttctcctc ctggaacaag gccatccctc aattgaacgt cgggcacgtg   1200
aagttgcggc gcgcggtaga ggcgttcgag aagaaatacc ctggaatcca tctctcgggc   1260
aactacctcc agggagttgc aataccagct ttactccagc acgccgcagc tttagctgct   1320
tctcttaaga agaactga                                                1338
```

<210> SEQ ID NO 46
<211> LENGTH: 1338
<212> TYPE: DNA
<213> ORGANISM: Artificial Sequence
<220> FEATURE:
<223> OTHER INFORMATION: Recombinant

<400> SEQUENCE: 46

```
cagcccgtcc tcatcgttgg agctggtctc tccgggctct caatcgctta cgaactacag     60
aagctgcaag tcccttacca agtgctggag gtttctggac attctggtgg agtcatgaag   120
```

| | |
|---|---|
| tcactccgga aggacggatt tgaactcgac gctggtgcca acaccatagc cacgtctccc | 180 |
| gagattcttg cgtactttac ctcactaggt cttgagaatg agatcctcca ggcgactgct | 240 |
| acttctaaac accgcttctt ggtgcggcga aggcaactgc acgccgtgag cccgcacccg | 300 |
| ttcaagatca tgtcatcgcc gtacctctgc cgtggctcca aatggaggct ctttactgag | 360 |
| cggtttcgga aacccgtcgt cgcttcgggc gaggagaccg tcaccgattt catcacgagg | 420 |
| agattcaacc gcgaaatagc ggagtatgtg ttcgaccctg ttctaagtgg gatctacgcc | 480 |
| gggaacccgg accaaatgag tattgctgag gtgttgcctg ccttgcctag gtgggaaagg | 540 |
| gagtacggat cagtgaccaa gggccttatg aaggataagg gtgcgatggg aggtcgaaag | 600 |
| atcatcagct ttaagggtgg caaccagcta cttacaaacc gcttacagca gctactcact | 660 |
| actccggtga gattcaattg caaggtgaca gggattacag ccagcaatgg cgggtacatc | 720 |
| gtgagcgctg ttgaggacgg cgtatctgag agctacaccg catctcgtgt gatcttgacc | 780 |
| acacccgctt actcagcagc ggctaccata actaaccttg atgcagccac tgcggcactg | 840 |
| ttgaacgaaa tccattatcc acgtatgggc gtgttacact gggctttga tgcaactgcc | 900 |
| ttgccacagc cgctggacgg gttcggattt ctagtgccga acgcggagaa catgcacttc | 960 |
| ctgggagcca tctgcaatgc agccatcttc ccggacaagg ctccgcccgg caagatcctg | 1020 |
| tttacagtgt tcctcggagg cgcacgccag gagtcgctct cgatcagat gactcctgag | 1080 |
| gctcttcagc agcaagtcgt tagtgaggtg atgagcttgt tgcacttgtc agctccaccg | 1140 |
| gtgatgcagc acttctcctc ctggaacaag gccatccctc aattgaacgt cgggcacgtg | 1200 |
| aagttgcggc gcgcggtaga ggcgttcgag aagaaatacc ctggaatcca tctctcgggc | 1260 |
| aactacctcc agggagttgc aataccagct ttactccagc acgccgcagc tttagctgct | 1320 |
| tctcttaaga agaactga | 1338 |

<210> SEQ ID NO 47
<211> LENGTH: 1329
<212> TYPE: DNA
<213> ORGANISM: Artificial Sequence
<220> FEATURE:
<223> OTHER INFORMATION: Recombinant

<400> SEQUENCE: 47

| | |
|---|---|
| atgcaaacgc aaccagtgat aatcgcgggc gctggcatcg ccggactttc cattgcgtac | 60 |
| gagctccagc agaagggtat cccgtacgag atcatggagg caagttccta tgccggcggc | 120 |
| gtcgtcaagt cactgcacat cgacgggtac gagctggacg cgggacccaa cagcctagcc | 180 |
| gcttccgctg ccttcatggc gtacatcgac cagctggggc tccaagacca agtcctcgag | 240 |
| gctgccgcgg cgagtaaaaa tcgctttctc gtgaggaacg acaagcttca cgctgtgtca | 300 |
| ccgcacccct tcaaaatact tcaaagcgcc tacatctcgg gcggtgctaa gtggcggtta | 360 |
| ttcacggagc gttttaggaa ggccgccgct cccgaaggtg aggagactgt ttcctctttc | 420 |
| gtcacacgca ggttcggaaa ggagatcaac gattatctct ttgagcctgt tctcagcgga | 480 |
| atatacgccg gcaacccaga ccttatgagc gtcggagagg ttctccctat gctgccgcaa | 540 |
| tgggagcaaa agtatggttc tgtgacccaa ggcctactga agaataaggg ggcgatgggc | 600 |
| ggaagaaaga taattgcatt caaggggggt aatgccaccc ttacaaatcg cctgcaaagc | 660 |
| cttttgtcgg gaaaaatccg tttcaattgt gccgtcaccg tgttacaag aggcgcagat | 720 |
| gattacatcg ttcagtacac cgagaacggt aataccgcca tgctaaacgc atctagggtg | 780 |

```
attttcacaa ccccggccta ctcaactgcc gtcgccatcc aagccctcga cgccagcctg   840
gccactcatc tcagtgatgt gccttaccct cgtatggggg tattacatct tggcttcggg   900
gccgaagcgc gacagaaagc ccccgctgga tttggcttcc tagtccctca cgccgccggt   960
aaacattttc ttggcgccat ctgtaactcc gcaatcttcc catccagagt gcctactggc  1020
aaggttctgt ttactgtgtt cctgggcggt gcccgccagg agcagctatt cgaccaatta  1080
ggcccagaaa agctccaaca aaccgttgtg aaggaactaa tggagttgct cggactgacg  1140
acaccacccg agatgcagag gttttctgag tggaaccgcg cgattccaca actcaacgtc  1200
gggtacgccc agacccggca acagataggg gtttttcgagc agcgctatcc aggcattcga  1260
cttgctggta attacgtcac aggagtcgct gtgccagcca aatacaagc tgcaaagggg  1320 tattgctga                                                         1329
```

<210> SEQ ID NO 48
<211> LENGTH: 1347
<212> TYPE: DNA
<213> ORGANISM: Artificial Sequence
<220> FEATURE:
<223> OTHER INFORMATION: Recombinant

<400> SEQUENCE: 48

```
atgtcagacc aaccagtctt gattgttggg gccggcctct ctggcctgtc gattgcctac    60
gaactgcaga agctccaggt gccgtaccaa gtcctggagg tgtcgggcca tagcggcggt   120
gtcatgaaat cgctgcgtaa ggacggcttc gagttggacg cgggcgcgaa cacaatcgcg   180
gctagcccag aaatacttgc ttactttaca agtctgggtc tggagaatga gatcctccag   240
gctacagccg ctagcaaaca tcgattcctg gtgcgcaggc gacaactgca cgccgtcagt   300
ccacatccat tcaagataat gtcgagcccc tatttaagcc gcgggtccaa gtggaggctc   360
tttactgaaa gatttcgaaa accggtcgtc gctagcggag aagaaactgt tacagatttt   420
attactcgca ggttcaacag ggagattgca gaatatgtct tcgatccagt tctctcagga   480
atttacgcgg gcaacccaga ccagatgagc atcgctgaag tcctgcccgc gctccctcgg   540
tgggaacgag aatatggaag cgtcaccaaa ggtctcatga aggacaaggg ggccatgggc   600
ggtcggaaga tcatatcgtt taaaggcggg aaccagcttc tgactaaccg gctgcaacag   660
ctgctcacta caccagtgcg gtttaattgc aaagtcacag gtataacggc tagtaatggc   720
ggctacattg tttcagcggt cgaagatggt gtgagcgagt catacaccgc ctcccgcgtg   780
atccttacca caccggccta ctcggcggca gctacaatca ccaatcttga cgcggctaca   840
gccgcattac tcaacgagat tcattatccc aggatggggg tcctccatct gggcttcgac   900
gcgacagctc ttccccagcc cttggatggc ttcgggtttc tggtcccgaa cgccgaaaac   960
atgcattttc tcggcgccat ttgcaacgcc gcgatcttcc cggataaggc cccgcctgga  1020
aaaatattgt tcactgtctt tcttggcggc gcacgccagg agtccctgtt cgaccaaatg  1080
accccagagg ctctgcagca gcaggtggtc tctgaggtga tgtcacttct gcacctttct  1140
gcacctccag tgatgcagca cttctcaagc tggaataaag ctatccccca gttgaacgtc  1200
ggccacgtga agcttcgtag ggcggtcgaa gcgttcgaaa agaagtatcc aggcattcac  1260
ctgtccggca actatctgca gggcgtcgca atcccggcgc tactccagca cgccgctgcg  1320
ctagccgcgt ctcttaagaa gaattag                                     1347
```

<210> SEQ ID NO 49
<211> LENGTH: 1413

```
<212> TYPE: DNA
<213> ORGANISM: Artificial Sequence
<220> FEATURE:
<223> OTHER INFORMATION: Recombinant

<400> SEQUENCE: 49
atgagtgacg ggaagaagca cgttgtgata atcggaggcg ggataaccgg cctcgccgcc        60
gccttctata tggagaagga aattaaggag aaaaacctcc cgctagagct gacgttggtg       120
gaagcgtcac caagggtcgg cggtaagatc cagaccgtca aaaaggatgg ctacatcatc       180
gagcgcggcc cggacagctt cctcgagcgg aagaagtccg caccccagtt agtcaaagac       240
ctcggcttgg aacacctttt ggtcaacaac gcgacaggtc agtcctatgt gcttgtgaat       300
cggacgctgc acccgatgcc taagggcgct gtcatgggta tccccacgaa gatcgcgccg       360
ttcgtatcga ccgcctgtt ctccctatca ggtaaggccc gcgctgccat ggactttatc       420
ctccctgcct cgaaaactaa agacgatcag tcactaggcg agttctttcg gcggcgagtg       480
ggtgacgagg tggtggagaa cctcatagaa cccctgctgt ccgggatcta cgctggagac       540
atcgacaagc tgagcctcat gtctactttt ccgcaatttt atcagaccga gcagaaacac       600
agatctctta tccttggcat gaagaagacc aggcctcagg ggtcgggtca acagctcaca       660
gcaaagaagc aagggcagtt ccaaaccctg agcacaggct gcagaccct ggtcgaagaa        720
attgagaagc agctgaaatt aacgaaggtt tacaagggaa ccaaggtcac caaacttagt       780
cacagcggct cgggctacag cctagagctt gacaacggag tgactctgga cgcagacagc       840
gtgatcgtga cggcgcccca caaggctgcg gcgggaatgc tgagtgagct ccccgccata       900
agtcatctca agaacatgca ctcgacgtcg gtagccaatg tcgcgttggg gtttcccgag       960
ggtagcgtcc aaatggaaca cgaaggaact ggtttcgtca tatcccggaa ctctgacttc      1020
gcgatcacag cgtgcacttg gacgaataaa agtggccgc acgcagcgcc tgaggggaag       1080
accctttctc gagcgtatgt gggcaaagcg ggcgatgaaa gcattgtgga tttatcggac      1140
aacgacatta tcaacatcgt actggaagac ctaaagaaag tcatgaacat aaacggcgaa      1200
ccggagatga catgcgtcac taggtggcac gagagcatgc cgcagtacca cgtggggcac      1260
aagcagcgca tcaaggaatt gagggaggcc ctcgctagcg cgtaccctgg agtttacatg      1320
accggcgcca gttttgaggg tgtcggtatc cctgactgta tcgaccaggg taaggccgcg      1380
gtaagcgacg cattgacgta cctgttctca tga                                  1413

<210> SEQ ID NO 50
<211> LENGTH: 1413
<212> TYPE: DNA
<213> ORGANISM: Artificial Sequence
<220> FEATURE:
<223> OTHER INFORMATION: Recombinant

<400> SEQUENCE: 50
atgcacgaca accagaagca tctggtcatc attggcgggg gcatcacggg cttggcagcc        60
gccttctacc tggagaagga ggtcgaggag aagggccttc cgattcaaat atctctgatt       120
gaggcgtctc cccgactcgg cgggaagatc cagaccctct ataaagacgg ctatataatt       180
gagcggggac cagattcttt cctggagcga aaggtctcgg gccacagtt ggcgaaagat        240
gtcggcctct ccgatcaact cgtgaacaac gagaccgggc aggcctatgt tctggtgaac       300
gagaaattgc atcctatgcc taaggggcc gtcatgggaa taccaaccca aatatctccc        360
ttcataacaa ccggactgtt ctcggttgcc ggtaaggcca gggccgcgat ggacttcgtc       420
```

```
ctgccaaagt ctaagcagac ggaggaccag tccctcgggg aattttttccg ccgccgggtc      480
ggcgacgagg ttgtggaaaa cctgattgag ccgttgctgt ctggcatcta cgcaggcgat      540
atcgacaggc tgagccttat gtctacgttc ccgcaatttt atcagaccga gcagcagcac      600
cggtctctga tacttggcat gaagaaatca acagcacg ccaaagcaca acaggttact         660
gctaagaagc aaggacaatt ccagacaatc aaccaagggt tgcagtccct cgtggaggcg      720
gtagaaggca aattgaaact caccaccgtc tacaagggca cgaaagttaa gcagatcgag      780
aaaacggatg gcgggtacgg tctccagctc gatagcggcc agacactgtt cgccgactca      840
gcgatcgtca ccaccccca ccagtccatc tacagcatgt tccctaagga ggcggggtta       900
gaatacttac atgacatgac ctccacctcc gtcgccacag tagctctcgg cttcaaggac      960
gaggacgtgc acaacgaata cgacggtacc gggttcgtga tctcgcggaa ttcggacttc     1020
agtattactg cctgcacctg gacgaacaag aagtggccac acacagcacc caaaggtaag     1080
accttgctga gggcttatgt gggtaaggcg ggggacgaga gcatagtgga gcagtctgac     1140
tcgcagatcg tcagcatcgt actggaagac ctgaagaaga tcatggacat caaggccgac     1200
ccggagttga ccaccgtcac acggtggaaa acctcaatgc cacaatatca tgtcggacat     1260
cagaaggcca tctccaacat gcgcgagacc ttcaagcagt cttacccggg cgtgtatatc     1320
accggagcgg ctttcgaggg ggtcggcatc cctgactgca tagaccaggg gaaggcggcc     1380
atcagcgagg ctgtgtcgta cctttttctcg tga                                 1413
```

<210> SEQ ID NO 51
<211> LENGTH: 1413
<212> TYPE: DNA
<213> ORGANISM: Artificial Sequence
<220> FEATURE:
<223> OTHER INFORMATION: Recombinant

<400> SEQUENCE: 51

```
atgcatgaca accagaagca cctggttatc attggcggtg gcataaccgg gctcgccgcc       60
gcctttttacc tggagaagga ggtggaggaa aaaggcctcc caatccagat cagtttgata      120
gaggcgagtc cgcgcttggg gggcaagatc cagactctgt ataaagatgg atacattatc      180
gagagggggtc cagacagctt cctggagcgc aaggtctccg ggcctcagtt ggcgaaggat      240
gttgggtttgt cagatcagct cgtgaacaac gaaacgggcc aggcgtatgt gttagtcaat      300
gaaactctgc accccatgcc caagggcgcg gtgatgggga tacccacccca gatcagtccc      360
ttcatcacaa ccgtctgtt ctcggtcgca gggaaggccc gagcggcgat ggattttgtc       420
ctgcccaagt cgaagcagac cgaggaccag agcctcgggg agttttttcag gcgcagagtt      480
ggcgatgagg tcgtcgagaa cctcattgag ccgcttctca gcgggattta tgcgggagac      540
atcgacaggc tctccctgat gtcaactttt ccgcagttct accagacgga gcaaaagcac      600
aggagcctga ttctgggaat gaagaagtca acaacatg ctaaagccca gcaggtaact         660
gcaaagaagc agggtcagtt ccaaacaatc aatcaaggtc tccaggcact cgtcgaggcc      720
gtggagtcaa agctaaagct gaccaccata tacaagggta ccaaagtgaa acaaatcgag      780
aagcagacgg gcggttacgg agtgcagctt gactccggcc agaccctcct cgccgactct      840
gcgatcgtga ccacgccgca ccagtccatc tactctatgt tccccaagga ggccgggctc      900
gaatatttgc acgatatgac cagcaccagc gtcgctacgg tagcactcgg gttcaaggag      960
gaggacgtcc acaacgagta cgatggcact ggcttcgtga tcagccgtaa ctctgatttc     1020
agcatcactg catgcacatg gactaataag aaatggcccc acactgcacc caagggcaag     1080
```

```
acgctgctgc gagcctacgt cgggaaggcc ggggacgagt ctattgtaga gcagagcgat    1140
caccagattg tgagtatcgt actggaggac ctgaaaaaga tcatggatat aaaggcggac    1200
ccagagctga ctaccgtgac ccgctggaaa acatccatgc cgcaatacca tgtgggccac    1260
caaaaagcga tctccaacat gcgggagacg ttcaagcaat cttatcccgg cgtgtacatc    1320
acgggagccg cgttcgaggg cgtgggcatc ccggattgca tcgatcaggg taaggctgcg    1380
atatcggagg ctgtcagtta cctgttttct tag                                1413
```

<210> SEQ ID NO 52
<211> LENGTH: 1434
<212> TYPE: DNA
<213> ORGANISM: Paenibacillus macerans

<400> SEQUENCE: 52

```
gtgagcaaaa aaatcgccgt catcggcgga ggcataaccg ggttaagcgt ggcttattac     60
gtgcgtaaat tgctgcgtga acaggggta  acgctgggg ttaccctcgt ggaacagtcc    120
gatcggctgg gcggcaaaat ccgttcccta cgacgtgacg gctttacgat agaacagggc    180
ccggattcaa tgatcgcgcg caagcccgcc gcgctggaat tgatccggga actcgggctg    240
gaggataagc tggcgggaac gaatccgcag gcgaagcgaa gttatatatt gcatcgcggc    300
aaattccatc ccatgccgcc ggggctgatg ctcggcatac cgacgcaaat gtggccgatg    360
gtcaagacgg gctgctctc  tccggccggc aagctgcggg ccgcgatgga tctgctgctt    420
cccgcgcggc gcggcggcgg cgacgaatcg ctcggcggct tcatccgccg ccggctcggc    480
agagaagtgc tggagcagat gacggagccg cttctagccg gcatatatgc cggggacacc    540
gaacagctta gcttgaaagc gacgtttccg cagtttatgg agatggagcg caagcaccgc    600
agcctgatcc ttgggctgct ggccggcaaa aagcagccgc cgcggccggg gggaagccag    660
gtcccgctgc cgaaggccgc gcaaaccagc atgtttctga cgttgacggg cggtttggag    720
ggactgacgg aagcgctgga ggaatcgcta agcgaagaga aaataattac cggccaggcg    780
gtaaccggac tgtcgcagca agaggcgggt tatgagctta acttaagcgg gggcgagcgt    840
ttgaacgcgg acggagtcat tttggcagtt cctgcttttg ctgcggcccg gctattggat    900
ggcgttcccg aagccgctta cctggagcgg atccgttatg tgtccgtggc caatttagcc    960
ttcgcctacc ggcgggaaga cgttccgcac gatttgaacg gctccggcgt gcttatcccg   1020
cgcggggagg ggcgaatgat tacggccatt acctgggttt cttcgaaatg gctgcattcg   1080
gctcccggcg ataaagcgct gctgcgagcc tatatcggcc gctgggcga cgaggcatgg   1140 accgcgatgt gcagggccga catcgagcgc cgggtggccg ccgagctgcg cgatttgctg   1200
ggcatcgccg ccagcccgct gttttgcgag ctcgccgctt tgccggagtc gatgccccaa   1260
tatccggtcg gcatgtcga  gcggcttgag gcgctgcgcg gggcattgtg ccgggcgaag   1320
ccggggctgc tgctgtgcgg cgcgggatat gccggcgtag gcattcccga ctgcatccgg   1380
cagggcaagg aagccgctga aagcatggcg gcttatttga gggatggacg gtga         1434
```

<210> SEQ ID NO 53
<211> LENGTH: 1482
<212> TYPE: DNA
<213> ORGANISM: Paenibacillus thiaminolyticus

<400> SEQUENCE: 53

```
atgaaagctc tgcggaaact tgtcgttatc ggtggcggaa ttacgggatt gagcgcggcg     60
```

-continued

| | |
|---|---|
| ttctatgcgc tgaagcaggc ggatgaagag gggcagccca tctccgttac catcatagag | 120 |
| caatcggacc gtctcggcgg gaagatacag accctgcgga aggaagggtg tgtcattgag | 180 |
| aaaggcccgg actccttcct cgcccggaag ctgccgatga tcgatttggc gcgcgacctc | 240 |
| ggaatggatt ctgaattggt cgccacgaat ccgcatgcca aaaaaacata tatattgcgc | 300 |
| cggggcaagc tgtaccggat gccgcccggc ctcgtgctgg gcatcccgac ggagctgggg | 360 |
| ccgttcgcga agacagggct catctccccg tggggaagc tgcgcgcggc tatggatctg | 420 |
| ttcatcaagc cgcatccggc ggatgaagat gaatccgttg gcgcgttcct ggacagacgg | 480 |
| ctcggacgcg aagtgacgga gcatattgcc gagccgctgc ttgccggcat ttatgccgga | 540 |
| gatttgcagg cgctgagcct gcaggccacc ttcccgcagt tcgcgcaggt ggagcggaag | 600 |
| cacggtggcc tgatacgcgg aatgaaggcg agccgccaag caggccaatc ggtaccgggg | 660 |
| ctgccggatg tcgccaaagg aacgatgttc ctgacattcc gcaacggctt gacctcgctc | 720 |
| gtcgaacggc tggaggagac gctgcgggac cgggccgaat tgtgccttgg catcggcgcg | 780 |
| gaaggattcg agaagcggga ggacggaacg tatctggtgc gcttgagcga tgggagcagg | 840 |
| ctgcaggcgg atgccgtcat cgtgacgacg ccttcgtatc atgcggcatc cttgctcgag | 900 |
| gagcatgtcg atgcgagcgc cttgcaggcg atccgtcatg tatccgtcgc gaatgtcgtc | 960 |
| agcgtgttcg atcgcaagca ggtcaataat cagttcgacg gcacagggtt cgtcatctcg | 1020 |
| cgccgggaag gccgggcgat tacgcctgc acgtggacct cggtgaagtg gccgcatacg | 1080 |
| agccgcgggg acaagcttat tatccgctgc tacattggcc gggccggtga cgaggaacgg | 1140 |
| gtggactggc cggacgaggc gctcaagcgg acggtgcgca gcgagctgcg ggagctgctt | 1200 |
| gatatcgata tcgacccgga gttcgtcgag attacgcgcc ttcgccactc gatgccccag | 1260 |
| tatccggtcg gccatgtgca ggcgatccgc tcgctgaggg acgaggtggg gcgcacgctc | 1320 |
| ccaggcgtgt tcctggcagg acagccgtac gaaggggtcg gcatgcccga ttgcgttcgc | 1380 |
| agccgccgcg atgcgcggga agccgcggtt agcgcgatgc aggccatgag tacggagcca | 1440 |
| gaggcgccag ccgaggatgc cgctactgga acggcggggt aa | 1482 |

<210> SEQ ID NO 54
<211> LENGTH: 1425
<212> TYPE: DNA
<213> ORGANISM: Paenibacillus polymyxa

<400> SEQUENCE: 54

| | |
|---|---|
| atgggtgata agaaacgccg tgttgttgtt gtcggcggtg gccttaccgg cctcagcgcg | 60 |
| gcatttttata tccgcaagca ttaccgggaa gcaggagttg aacctgtgat tactttggtc | 120 |
| gagaaaagct cgtccatggg aggcatgatt gagacactgc accgggatgg atttgtgatt | 180 |
| gaaaaagggc ccgattcgtt cctggctcgc aaaacggcaa tgattgatct ggccaaagaa | 240 |
| ttggagatcg atcatgagct ggtaagtcag aatccggagt cgaagaaaac gtatatcatg | 300 |
| cagcgtggca agcttcatcc tatgccagca ggacttgttc tcggtattcc gacagaacta | 360 |
| agaccattct tgagaagtgg tttggtttct ccggcaggca aactgcgggc gttgatggat | 420 |
| tttgtcatcc cgccgcgtcg tacaacagag gatgaatcgc tcggttatat gattgaacgc | 480 |
| cgtcttggag cagaagtgct ggagaacttg acggaaccac tgctcgcagg aatctatgca | 540 |
| ggtgatatgc ggcgattgag cctccaggct accttcccgc agttcggaga agtagagcgc | 600 |
| gattacggca gcttgatccg gggcatgatg acggggcgca aaccggctga gacgcatacc | 660 |
| ggaacaaaac ggagcgcttt tttgaacttt cgccagggac ttcagagcct tgttcatgca | 720 |

```
ctcgtccatg agttgcagga tgtggatcaa cgtctgaaca ctgcggtgaa atcgctgcaa    780
cgccttgatg gagcgcagac cagataccgt gttgaacttg gtaatggcga atgcttgaa     840
gccgatgatg tagtggttac tgtgccgaca tatgtcgcgt cggagctgtt gaagcctcac    900
gtggacacag cggcactgga tgcgattaac tatgtgtctg tagccaatgt agtgctcgct    960
tttgagaaaa agaggtgga gcatgtattc gacggatcgg gtttcctcgt tccgcggaaa    1020
gagggtcgga atattacggc ttgcacgtgg acatcgacga aatggctgca taccagcccg   1080
gatgataaag tactgcttcg ctgttatgtt ggtcgctccg gtgacgaaca gaacgtagag   1140
cttccggatg aagcgctgac gaatctcgtt ctcaaagatc tgagagagac gatgggtatt   1200
gaagcagtgc cgatcttctc cgagattaca aggcttcgta atccatgcc acagtatccg    1260
gtgggacacc ttcaacatat tgccgctctc cgtgaggagc ttggcagcaa attaccgggt   1320
gtgtacattg caggtgcagg ttatgagggc gtaggcttgc ctgattgcat cagacaagcg   1380
aaggaaatgt ctgttcaggc tacacaagag cttgcagcag attaa                   1425
```

<210> SEQ ID NO 55
<211> LENGTH: 1413
<212> TYPE: DNA
<213> ORGANISM: Bacillus atrophaeus

<400> SEQUENCE: 55

```
atgagtgacg gcaaaaagca tcttgtcatc atcggcggcg gcatcacggg attggcctcc     60
gccttctata tggaaaaaga atcagagag aaaaatttgc ctctttctgt gacgttagtc     120
gaagcaagcc cgagagttgg cgggaaaatt caaacggccc gcaaggacgg ttatattatt    180
gaaagagggc cggactcatt tttagaaaga aaaaaaagcg caccggagct tgtcgaagat    240
ttaggccttg agcatttgct tgtcaacaat gcgacggggc agtcttatgt gctggttaac    300
gaaacgcttc acccgatgcc aaagggcgct gttatgggca tacctactaa aatagcgcca    360
tttatgtcta ccggcttatt ttcattttcc ggcaaagcgc gcgcggctat ggatttcgtt    420
ttgcccgcaa gcaagccgaa ggaagatcag tccctgggtg aattcttccg caggcgtgtc    480
ggtgacgaag ttgttgaaaa tttgattgag ccgctattat ccggcattta tgcgggtgac    540
attgacaggc tcagcctgat gtcgacgttc ccgcagtttt atcagaccga acaaaagcac    600
agaagcttga tcctcggcat gaaaaaaaca aggcctcagg gctccggaca gcggttaacg    660
gctaaaaaac aagggcaatt ccaaacctta aagaccggct tgcagacact cgtcgaagag    720
ctggaaaacc agctgaagct gacgaaggta tacaagggta caaagtaac caatatcagc    780
cgcggggaaa agggctgctc catcgctctt gataacggga tgacgctgga tgccgatgca    840
gcgattgtaa cctcaccgca caaatcggct gccggaatgt tccggatct gccagctgtc    900
agtcagttaa aagacatgca ctctacctct gtggcgaatg tcgcgcttgg ctttccacaa    960
gaggctgtcc aaatgaaca tgaaggaacg ggtttttgtca tctcaagaaa cagtgatttt   1020
tcaataacgg cctgtacttg gacgaataaa aaatggccgc actctgctcc ggaaggcaaa   1080
acgctcctca gggcttatgt cggaaaagcg ggtgatgaat caatcgtcga actgtctgat   1140
aatgagatta tcaaaattgt attagaagac ctaaagaaag tcatgaaaat caaggcgaa    1200
cctgaaatga cgtgcgtcac acgctggaat gagagtatgc cccaatatca tgtcggccac   1260
aaacagcgta taaaaaaagt gcgcgaagca ctggctgctt cctatccggg agtttacatg   1320
acgggcgctt cattcgaagg cgttgggatt ccggactgta tcgatcaagg gaaaagcgcc   1380
```

```
gtttcagacg tacttgctta tttattcggt tga              1413
```

<210> SEQ ID NO 56
<211> LENGTH: 1413
<212> TYPE: DNA
<213> ORGANISM: Bacillus atrophaeus

<400> SEQUENCE: 56

```
atgagtgacg gcaaaaagca tcttgtcatc atcggcggcg gcatcacggg attggcctcc    60
gccttctata tggaaaaaga atcagagag aaaaatttgc ctctttctgt gacgttagtc   120
gaagcaagcc cgagagttgg cgggaaaatt caaacggccc gcaaggacgg ttatattatt   180
gaaagagggc cggactcatt tttagaaaga aaaaaagcg caccggagct tgtcgaagat   240
ttaggacttg agcatttgct tgtcaacaat gcgacggggc agtcttatgt gctggttaac   300
gaaacgcttc acccgatgcc aaagggcgct gttatgggca tacctactaa aatagcgcca   360
tttatgtcta cccgcttatt ttcatttttcc ggcaaagcgc gcgcggctat ggatttcgtt   420
ttgcccgcaa gcaagccgaa ggaagatcag tccctgggtg aattcttccg caggcgtgtc   480
ggtgacgaag ttgttgaaaa tttgattgag ccgctattat ccggcattta tgcgggtgac   540
attgacagac tcagcctgat gtcgacgttc ccgcagtttt atcagaccga acaaaagcac   600
agaagcttga tcctcggcat gaaaaaaaca aggcctcagg gctccggaca gcagttaacg   660
gctaaaaaac aagggcaatt ccaaaccta agaccggct tgcagacact cgtcgaagag   720
ctggaaaacc agctgaaact gacgaaggta tacaagggta caaaagtaac caatatcagc   780
cgcgggaaa agggctgctc catcgctctt gataacggga tgacgctgga tgccgatgcc   840
gcgattgtga cctcaccgca caaatcggct gccggaatgt ttccggatct gccagctgtc   900
agccagttaa aagacatgca ctctacctct gtggcgaatg tcgcgcttgg cttttccacaa   960
gaggctgtcc aaatggaaca tgaaggaacg ggttttgtca tctcaagaaa cagtgatttt  1020
tcaataacgg cctgtacttg gacgaataaa aaatggccgc actctgctcc ggaaggcaaa  1080
acgctcctca gggcttatgt cggaaaagcg ggtgatgaat caatcgtcga actgtctgat  1140
aatgagatta tcaaaattgt attagaagac taaagaaag tcatgaaaat caaaggcgaa  1200
cctgaaatga cgtgcgtcac acgctggaat gagagtatgc cccaatatca tgtcggccac  1260
aaacagcgta taaaaaaagt gcgcgaagca ctggctgctt cctatccggg agtttacatg  1320
acgggcgctt cattcgaagg cgttgggatt ccggactgta tcgaccaagg gaaaagcgcc  1380
gtttcagacg tacttgctta tttattcgaa tga                             1413
```

<210> SEQ ID NO 57
<211> LENGTH: 1434
<212> TYPE: DNA
<213> ORGANISM: Artificial Sequence
<220> FEATURE:
<223> OTHER INFORMATION: Recombinant

<400> SEQUENCE: 57

```
atgtcaaaga agattgcagt cattggtggt gggataacag ggttgtccgt ggcctactac    60
gtgaggaagc tgcttcggga gcaaggcgtt aatgcgggcg ttaccctcgt cgagcaatcc   120
gaccgcctcg gcgggaagat tagatccttg agacgagacg gctttaccat tgagcaaggc   180
cctgactcta tgattgcacg taagcccgca gctctcgaac ttatccgtga gcttggtctg   240
gaggacaagt tggcgggcac aaaccctcaa gccaaacgct cctacatact gcaccgtggc   300
aagtttcatc cgatgccacc tgggctgatg ctcgggattc ccactcaaat gtggccaatg   360
```

```
gtcaagaccg ggctgctatc tccggccgga aagctacggg ctgcgatgga cctacttctt    420
cctgcaaggc gcggaggcgg cgacgaatca cttggtgggt ttatccggag gcggcttgga    480
cgtgaggtgt tggagcagat gaccgaacca ctccttgctg gaatctatgc tggcgacaca    540
gaacagcttt cacttaaagc gacctttcct caattcatgg agatggaaag gaaacatcgc    600
agtctcatcc ttggactatt ggctgggaag aaacagccac cgcgtcccgg tggtagccaa    660
gtgccgctcc caaggccgc tcagaccagt atgttcttga cactcaccgg cgggttggaa    720
ggtctgaccg aagcactaga ggaaagccta tcagaggaga agataattac tggccaagca    780
gttaccggac tttcgcagca agaggccggg tatgagttaa atctctctgg cggagagaga    840
cttaatgcag acggagtgat cctcgcagtc ccagcgttcg ctgccgcccg acttcttgac    900
ggcgtgcctg aggccgccta cctagagcgc atccgctatg tcagtgttgc taatttggcg    960
ttcgcttaca ggcgtgagga cgtgcctcat gatctgaatg ggtccggcgt gttaatccct   1020
agaggtgaag ggaggatgat tacgccata acttgggttt cgtccaaatg gttgcattca   1080
gcacccggtg acaaggcact gctgagagcg tacattgggc gactaggtga tgaggcttgg   1140
acagccatgt gtagggccga catcgagcgt agagtcgccg ctgaactccg cgatctacta   1200
ggaattgccg ctagtccttt gttctgtgaa ctagccgcac tcccagaatc tatgccgcag   1260
tatccagtgg gtcacgtcga acgactcgaa gccttgcgag gagcattgtg tcgcgctaaa   1320
ccagggttgt tgttgtgtgg tgccgggtac gctggcgttg gcattccaga ctgcattcgg   1380
caaggcaaag aagccgctga gtcgatggcg gcttatttga gggacggacg ctag         1434
```

```
<210> SEQ ID NO 58
<211> LENGTH: 1482
<212> TYPE: DNA
<213> ORGANISM: Artificial Sequence
<220> FEATURE:
<223> OTHER INFORMATION: Recombinant

<400> SEQUENCE: 58
```

```
atgaaggctc tgaggaaact tgtggtcatc ggcggaggga tcactgggct ttcggccgcc     60
ttctatgcac taaagcaagc cgatgaggaa gggcagccca tctcggtcac cataattgaa    120
cagagcgata ggctcggcgg aaagatccag acactccgca aggagggctg cgtaattgag    180
aagggcccgg attccttcct cgctaggaag ttgccgatga ttgatctagc tcgggatctt    240
ggcatggact ccgaattggt ggcgactaat ccgcacgcaa agaagactta catcttgagg    300
cgcggaaagc tctaccggat gcctccaggc ttagtgcttg gcataccta cggaactagga    360 ccattcgcta agacagggct cattagccct tggggcaaac tccgcgccgc tatggatttg    420
ttcattaagc tcatccagc cgatgaagac gaaagtgttg gcgctttcct ggacagacgt    480
ctcggtaggg aagtgaccga gcacattgcg gaacctttat ggcgggcat ctacgcgggc     540 gacttgcaag cct taagcct tcaagccact ttcccacagt ttgcacaagt agagcgcaag    600
cacggagggc tgatacgcgg tatgaaggcc agcagacagg ccggtcagtc cgtgcctggg    660
ctgccggacg tcgccaaggg tacgatgttc cttacctttc gcaacgggct taccagctta    720
gttgaaaggt tggaggaaac tctcagagac agggctgaac tctgtctggg catcggcgca    780
gaagggtttg agaaacgtga agatggaaca taccttgttc gactaagcga tggttcgagg    840
ctccaggccg acgcagtaat tgtcactacg ccgagctatc atgcggcatc cctgttggag    900
gagcatgtgg atgcttcggc cctccaggcc attcgtcatg taagcgttgc aaatgtcgtt    960
```

| | |
|---|---|
| agcgtcttcg accgaaagca agtgaataac cagttcgacg gcacagggtt tgttatctca | 1020 |
| cggcgagaag gtcgcgcaat caccgcctgt acctggacat ccgtgaaatg gccgcatact | 1080 |
| tcgcgcggcg acaaactgat tatccggtgc tacatcggta gggctggcga cgaggagcga | 1140 |
| gtggattggc ccgatgaagc tctcaagcgt actgtaagat cagaactgcg tgagttgctg | 1200 |
| gacattgaca ttgatccgga atttgtggag attacacgac tcaggcactc tatgcctcaa | 1260 |
| tacccagtcg gccacgtcca ggctatccgc tctttgaggg acgaggtcgg taggactta | 1320 |
| ccgggcgtgt tccttgctgg gcaaccctac gaaggtgtgg gaatgcctga ctgtgtgagg | 1380 |
| tccggccggg atgccgccga agcagcagta agtgctatgc aagcaatgag tacagaacca | 1440 |
| gaagcaccgg cagaggacgc cgctactgga acggcgggtt ga | 1482 |

<210> SEQ ID NO 59
<211> LENGTH: 1425
<212> TYPE: DNA
<213> ORGANISM: Artificial Sequence
<220> FEATURE:
<223> OTHER INFORMATION: Recombinant

<400> SEQUENCE: 59

| | |
|---|---|
| atgggagaca agaagcggag agttgttgtt gttggcggcg gcttgactgg cctaagcgcc | 60 |
| gccttctaca tccggaaaca ttatcgagaa gctggagttg agcccgtcat cacgcttgtt | 120 |
| gagaaatcta gctcgatggg agggatgatt gagacccttc ataggacgg gtttgtcatc | 180 |
| gagaagggcc cggacagttt cttggcacgg aagaccgcaa tgattgatct ggcgaaagag | 240 |
| ctggagattg accacgagtt ggtcagccag aatccagaat cgaagaagac ctacataatg | 300 |
| caacgtggaa agctgcaccc tatgccagcg ggacttgttc tgggcattcc caccgaattg | 360 |
| cgtccctttc tccggagcgg gcttgtctca cccgctggga agttgcgggc gctgatggac | 420 |
| ttcgtaatac cgccacgaag gacgaccgaa gatgagtcac tcgggtacat gatcgagcgc | 480 |
| cgactgggtg ccgaggtgtt ggagaacctc acagagccgt tgctcgctgg aatctacgct | 540 |
| ggcgacatga aagattgtc cctccaggct acgtttccgc agttcggtga ggtggagcgc | 600 |
| gactacggct ccttaatcag aggaatgatg accggacgta agcctgcgga cacacacaca | 660 |
| gggaccaaga ggtctgcctt tctcaatttc agacagggtc tgcaatcact ggttcacgcc | 720 |
| ttagtccatg aactccagga tgtagatcag aggttaaata ctgcggtgaa gtcgcttcag | 780 |
| aggcttgacg gcgcacaaac ccgttatcgc gttgaactcg gcaatggcga atgcttgag | 840 |
| gctgacgacg tggtggttac tgtaccaacc tacgtggcga gcgagcttct taagccgcac | 900 |
| gtggacacgg cggcgttaga cgctattaac tatgtgtcgg tggctaatgt agttcttgca | 960 |
| ttcgagaaga aggaagtaga gcacgtcttc gatggatcgg gcttcttggt gcctcggaag | 1020 |
| gagggaagga acataaccgc ctgcacctgg acttcgacca gtggctcca cacatcacca | 1080 |
| gatgacaagg ttctgttacg ttgttacgtg ggcagaagtg gagatgagca gaatgtggaa | 1140 |
| ctcccggatg aggcactcac taatctggtg cttaaggatc tgagagagac gatgggcatc | 1200 |
| gaggcggttc caatcttctc agagattacc cggctccgca agtcaatgcc gcagtaccca | 1260 |
| gtaggacatc tccagcacat cgccgcattg cgcgaggaac tcggctctaa gctaccagga | 1320 |
| gtgtacatcg ccggagcggg ctacgagggc gttggtcttc cggattgcat tcgccaggcc | 1380 |
| aaagaaatgt cagtccaggc aacgcaagaa ctcgctgccg actga | 1425 |

<210> SEQ ID NO 60
<211> LENGTH: 1413

```
<212> TYPE: DNA
<213> ORGANISM: Artificial Sequence
<220> FEATURE:
<223> OTHER INFORMATION: Recombinant

<400> SEQUENCE: 60
atgagtgacg ggaagaagca cttggttata atcgggggg gaataaccgg cctggccagc      60
gctttctata tggagaagga gatccgggag aagaacttac ctctcagcgt gaccttggtg     120
gaggcatccc cgcgggtagg ggggaagatc cagactgctc gaaaggacgg ctatatcata     180
gagcggggcc cggacagctt cctggagcgc aagaagtcgg cgcccgagtt agtcgaggac     240
ctcggtctcg agcacttact cgtaaacaac gctacaggc agtcttacgt cctcgtcaac      300
gaaacactgc acccgatgcc caaaggcgcg gtgatgggaa tccccactaa gattgcacct     360
ttcatgtcga ctggccttt cagcttcagt gggaaggcga gggcggcaat ggacttcgtc      420
ctgcccgcgt ccaagccgaa ggaggatcag agcctcggcg agttttccg caggcgagtt      480
ggggatgagg tcgtggaaaa cctcattgag cccttgctat ccggaatcta tgccggagac     540
atcgacaggc tcagccttat gtctactttc ccccagttct accagacaga gcaaaagcac     600
cgaagtttga tcctcgggat gaagaagacg cgtcctcagg ttctggtca gaggctaaca      660
gcaaagaagc agggtcaatt ccagacgctt aaaacagggc ttcaaacact tgtggaggaa     720
ctcgagaatc agcttaaact aaccaaagtg tacaagggca cgaaggtaac taacatcagc     780
cgcggtgaaa agggctgcag catcgcactt gacaacggga tgacactgga cgcggacgca     840
gcaatcgtca cgagccccca caaatcagcg gcgggaatgt ccccgaccct tccggcggtc     900
agccagctga agacatgca ctccacctcc gtcgcaaacg tcgcgctcgg cttcccgcag      960
gaggctgtcc agatggagca tgagggact ggcttcgtta tcagcagaaa ttcggacttc     1020
agtatcacag cgtgcacttg acaaacaag aaatggcctc acagcgcacc tgaggggaag     1080
acacttttgc gagcgtacgt ggggaaagct ggggacgagt ccatagttga actaagcgac     1140
aacgagataa ttaagatcgt gcttgaggac cttaagaaag tgatgaagat aaagggcgag     1200
cccgaaatga catgcgtaac tagatggaat gagtccatgc cacagtacca cgtcgggcac     1260
aagcagcgta tcaaaaaggt cagggaggct ttggcggcct catacccggg cgtatacatg     1320
accggtgcat ccttcgaggg ggtggggata ccagactgca tcgaccaagg caaatccgca     1380
gtctcagacg ttttggcata cttgttcggc tag                                  1413

<210> SEQ ID NO 61
<211> LENGTH: 1413
<212> TYPE: DNA
<213> ORGANISM: Artificial Sequence
<220> FEATURE:
<223> OTHER INFORMATION: Recombinant

<400> SEQUENCE: 61
atgtcggatg caagaagca cctcgtcatc atcggcgggg gtatcaccgg acttgcgtcc       60
gcgttctaca tggagaagga gatcagggag aagaacttgc ccctctcagt gaccctggtg     120
gaggcctcgc cccgtgttgg tggtaagatc cagacagcgc gaaaagacgg ctacattatc     180
gagcggggc ccgactcctt cctcgagagg aagaagtctg ccccgagct tgtggaggac       240
ttggggcttg agcacctcct cgtgaacaat gcgaccgggc agagctacgt tttggtgaac     300
gagacccctgc acccgatgcc caagggagcc gtgatgggga tccctaccaa gatcgcgcct     360
ttcatgagca ctcgactttt ttcattcagc ggcaaggcca gagccgctat ggactttgtt     420
```

```
ctcccggctt ctaagcctaa ggaagaccag agtctaggcg aattcttcag gcgaagagtc      480
ggcgatgagg ttgttgagaa ccttatagag ccattattgt caggtatata cgcaggagac      540
attgacaggc tgtctctcat gagtaccttc cctcaattct accagacgga gcagaaacac      600
aggagcctca tattggggat gaagaagacg cgtcctcaag gaagcggaca gcagttgacg      660
gccaagaagc agggccagtt ccaaacgctc aagaccggac ttcagaccct cgtcgaggag      720
cttgagaacc agctaaagtt gacgaaggtt tacaagggca ctaaggtcac aaacatctcg      780
aggggcgaga agggatgcag catcgcgtta gacaacggga tgaccctaga cgctgacgca      840
gctattgtga ctagccccca taagtccgca gccggcatgt ttccagactt gccggccgtt      900
agccagttga aggacatgca ctcgaccagc gtggcaaacg tcgcattggg cttcccacag      960
gaggcggtgc agatggagca tgaggggacc ggattcgtga tctcaaggaa ttccgatttc     1020
tccattacgg catgtacctg gacaaacaaa aaatggcccc acagcgcccc agaagggaaa     1080
acactcctac gcgcttatgt tggcaaggcc ggcgatgagt caattgtgga gctctccgac     1140
aatgagatca tcaaaatcgt tcttgaagat cttaagaagg taatgaagat taaggggaa      1200 ccggaaatga cgtgtgtgac aaggtggaac gagagtatgc cccaatatca cgtgggccac     1260
aagcagagga taaagaaggt gagggaggcg ttggcggcgt cttaccccgg cgtgtacatg     1320 acggggctt cattcgaggg ggtgggcatc cccgactgca ttgaccaagg caaaagcgcg     1380
gtgtctgacg tgctcgcgta cctgttcgag tag                                 1413

<210> SEQ ID NO 62
<211> LENGTH: 1413
<212> TYPE: DNA
<213> ORGANISM: Artificial Sequence
<220> FEATURE:
<223> OTHER INFORMATION: Recombinant

<400> SEQUENCE: 62
atgtccgacg ggaagaagca cctggtaatc atcggtggtg ggatcaccgg tctggcttca       60
gcgttctaca tggaaaagga gatccgggag aagaacttgc ccctttcggt gactctagtg      120
gaggcctctc cacgggtggg gggcaagatt cagaccgcgc gcaaggatgg ctacatcata      180
gagcgaggac cagactcatt cctagagcgt aagaagtccg ccccagagct cgtcgaggat      240
ctcggtctag agcacttgct agtgaataac gctacaggac agtcctacgt gctcgtgaac      300
gagacactac acccgatgcc taagggggct gtcatgggta taccgaccaa gatcgccccg      360
ttcatgtcca ctcgcctttt ctcgttctcg gcaaagctc gggccgctat ggatttcgtc      420
ttgcctgcct cgaaaccgaa ggaggaccag tccttaggag agttcttccg ccggagggtc      480
ggcgacgagg tggtggagaa cttaatcgaa cccttgctct cggggatcta cgctggagac      540
attgatcgac tatcgcttat gtctacgttt cctcaatttt accagacgga gcagaagcac      600
cgtagcctca ttttgggtat gaagaagaca cggcctcaag gttcggggca gcagcttact      660
gccaagaagc agggccaatt ccagacactc aagaccggct tgcagactct agtggaggag      720
ctggagaatc aattgaagct gacaaaggtc tacaagggta ccaaggtgac aaacatatcg      780
cgtggcgaaa agggatgctc cattgccctc gacaacggta tgaccctcga cgccgacgca      840
gcgattgtga cgagcccaca caagagcgcc gcgggcatgt tcccggactt gcctgcagtg      900
tcacagctga aagacatgca ttctacatcc gtcgccaacg tcgccctggg cttttccccag      960 gaggctgtgc agatggagca cgaggggacg ggcttcgtta tcagccgcaa ctccgacttt     1020
tctattaccg cgtgcacatg gaccaacaag aagtggccgc acagcgctcc ggaggggaaa     1080
```

```
acacttctcc gagcatacgt aggcaaggcc ggggacgagt caattgttga gctctccgac    1140
aatgaaatca ttaaaatagt tctggaggat cttaagaagg taatgaagat aaaggggaa     1200 cctgaaatga cgtgtgttac ccgctggaat gagtcaatgc cccagtacca tgtgggacac    1260
aagcagagga taaagaaggt gagggaggcg ctcgctgcgt cctacccagg ggtctacatg    1320
acaggagcga gttttgaggg ggtgggtatt cccgactgta tcgaccaggg taagtcggca    1380
gtgtctgacg tgctcgctta cctattcgag tag                                 1413
```

<210> SEQ ID NO 63
<211> LENGTH: 1434
<212> TYPE: DNA
<213> ORGANISM: Artificial Sequence
<220> FEATURE:
<223> OTHER INFORMATION: Recombinant

<400> SEQUENCE: 63

```
atgtcgaaga agatcgccgt tatcggtgga ggcattacag ggctctcggt cgcctactac     60
gtgcgtaagc tgcttcgtga gcaaggcgtc aacgctggtg tgacgctggt tgagcagtct    120
gatcgcctcg gtggaaaaat ccgtagcctt cgcagagacg ggttcacgat tgaacaagga    180
ccagattcca tgatcgcgcg caaacccgcg gcgttggagc taattcgaga actcggactc    240
gaggacaagc tcgccggcac taacccacag gcaaagcggt cgtacatcct tcaccgcggg    300
aagttccacc cgatgccccc aggcctgatg ctcggcatcc cgacccagat gtggccgatg    360
gtcaagaccg gctcctgtc tcccgcgggg aaactaaggg ccgctatgga cctcctcctc    420
cctgctcgga ggggcggcgg tgatgagagt ctcggggat ttatcaggcg gagattaggc     480
cgcgaggtac ttgagcaaat gaccgaacca ctgctcgcag gtatctatgc aggcgatacg    540
gaacaactgt ccttgaaagc aacatttcca caattcatgg agatggaaag aaaacatagg    600
tccctcatac tcggtcttct tgctggaaaa aagcaacctc cgagacccgg tggttcacaa    660
gtgcctctgc ctaaagcggc gcaaacttca atgttcctga ctctgacagg cgggctcgaa    720
ggccttaccg aagctctaga ggaatccttg tctgaggaaa aaataatcac cggccaggct    780
gttaccgggc ttagccaaca ggaagccggt tatgaactga ccctttcagg tggagagagg    840
ttgaacgccg atgggtcat attggctgta ccggcgttcg ccgcggctcg cctgctggac     900
ggcgtccctg aggccgcgta tttggagcgc atacgctatg tttctgttgc gaacctcgct    960
tttgcatata gacgggaaga tgtgcccat gatcttaatg gttccggagt gttgatccca    1020
cgcggggagg gtcgaatgat aacggcaatt acttgggttt ccagcaagtg gttacattcg    1080
gctcctgggg ataaagctct tttgcgggca tacatcggac gtctcggcga cgaagcctgg    1140
acggccatgt gcagagccga cattgagcga cgggtcgctg cagagctgag agacttgttg    1200
ggcatagctg catctccatt gttctgcgag ctggctgcat tgcctgaaag catgccgcaa    1260
tatccagtag gcatgtgga gcgcctcgaa gctctccgag gcgcgttgtg tagggcgaaa    1320
cctggactgc tgctctgcgg tgccggctat gcaggtgtgg gaattcctga ctgtatcagg    1380
caaggtaaag aagcggcaga gtccatggcc gcttaccta gggatgggcg ctag          1434
```

<210> SEQ ID NO 64
<211> LENGTH: 1482
<212> TYPE: DNA
<213> ORGANISM: Artificial Sequence
<220> FEATURE:
<223> OTHER INFORMATION: Recombinant

<400> SEQUENCE: 64

```
atgaaggcgc tgcggaagct ggtggtaatc ggggggggga tcacgggct gtcggccgcg      60
ttctacgcac tcaagcaggc cgacgaagag ggtcagccaa tttccgtaac gattatcgag     120
caatccgatc gacttggcgg caagatacag accctgagaa aggagggatg cgtcattgaa     180
aagggaccag attcatttct ggcgaggaag ctccccatga tcgatctggc gagagactta     240
ggcatggact cggagctggt ggccacaaat cctcatgcaa aaagactta catcctacgg      300
cgcggtaagt tgtaccgcat gccaccgggc ctggtgttgg ggattcctac cgagttagga    360
cccttcgcga aaccggact catcagcccc tgggggaaac ttcgagccgc gatggacctt     420
ttcatcaaac cacatccagc cgatgaagat gagtctgtgg gagctttttt agatagacgt    480
ttaggtcgcg aggtgacgga gcacatcgca gagccgctgc tcgccgggat atacgcaggc    540
gatcttcaag ctttgtcctt gcaagctacg ttccctcagt tcgcgcaagt ggaacgcaaa    600
cacggaggtc tcatcagagg tatgaaagcg ctctcgccaag ctggacagtc agtcccaggg   660
ctcccagatg tggccaaggg taccatgttt cttactttca gaaatggttt gactagcctg    720
gtggagcgtc tcgaagaaac ccttcgagat agagccgagc tctgtctggg tatcggtgca    780
gaggggtttg aaaaacggga agacggcacg taccttgttc gattatctga tggctccaga   840
ttgcaagccg acgccgttat agttaccaca ccatcatacc atgccgcctc cctactggag    900
gagcacgtcg acgccagcgc gttacaggct atccgcacg tatctgtagc caacgtggtg    960
agcgttttcg ataggaagca ggttaacaat cagtttgatg ggacaggttt tgttatctca   1020
agacgcgaag gcagggctat cactgcttgc acttggacct cagttaagtg gccgcatacc   1080
agccgggggg ataagttgat aatccggtgt tacattggtc gtgcaggaga tgaggagcgc   1140
gtggattggc cagacgaagc gctaaagcgg accgtgagaa gtgagcttcg cgagctgtta   1200
gacatagaca tagatcccga attcgtggaa attacacggt tgaggcactc tatgccacaa   1260
taccctgttg gtcatgtgca agctatacgg tccctgcgcg acgaagtagg ccggaccttg   1320
ccgggcgtgt ttcttgcggg tcagccgtat gagggggttg ggatgccaga ttgtgtgcgt   1380
tctggccgcg acgcggcaga ggctgccgta tcagccatgc aagccatgtc gacagaaccc   1440
gaagccccgg cggaagatgc agcgacagga actgcaggtt ag                      1482
```

<210> SEQ ID NO 65
<211> LENGTH: 1425
<212> TYPE: DNA
<213> ORGANISM: Artificial Sequence
<220> FEATURE:
<223> OTHER INFORMATION: Recombinant

<400> SEQUENCE: 65

```
atgggggata agaagaggag ggtcgttgtc gtgggtgggg gactgaccgg actatcagcc     60
gcgttctaca ttagaaagca ctaccgagag gccggcgtgg agccggtgat cacgctggtc    120
gagaagtcga gttcgatggg cggaatgatc gagaccctac acagggacgg ctttgtgatt    180
gagaagggac cagatagctt ccttgcacgc aagacagcca tgatcgatct cgcaaaagag    240
ctcgagatag accacgaact ggtgtctcag aacccggagt ccaagaagac atatatcatg    300
cagagaggta aactacaccc catgccagcc gggttggttc taggaatacc taccgagctc    360
cgcccgtttt tgcgtagcgg tctcgtgagc cccgccggga agctgcgtgc gctaatggac   420
ttcgtgatcc cgcctcggcg aacgaccgaa gacgaatcgc tggatacat gattgaacgg    480
cgattgggcg ctgaggtgct tgaaaatctt acggagcctc tgcttgcagg gatttatgcg    540
```

```
ggtgatatga ggcggttgtc tctccaggca acgttccacc agttcggtga ggtagaacgc    600
gattacggct cactgatacg gggcatgatg accggtcgca agcctgccga gacacacacc    660
ggtacaaaaa ggtcagcctt tcttaatttc cggcaagggt tacagtcact tgttcatgca    720
cttgtacacg aattgcagga cgtcgatcaa agacttaata ccgcagtgaa gagcctgcag    780
cgcctggatg gggcccaaac taggtaccgt gtggaattag caatggaga gatgctggag     840 gccgatgacg tggtggtcac cgtcccaacg tacgtagctt ctgagctcct caagccccac    900
gttgacaccg cagctctgga tgcaatcaat tatgtgagcg tggctaatgt cgtcctggcc    960
tttgagaaga aggaagtgga gcatgtgttc gacggatcag ggttcttggt tccgagaaaa   1020
gagggcagga atatcacggc gtgcacttgg acttcgacaa aatggctcca cacctccccg    1080
gatgacaaag tacttctgcg atgctatgtg ggccgaagtg gtgatgagca gaatgtagag   1140
ctccccgacg aggcactgac caacctcgtc ctcaaggacc taagggagac tatgggcatt   1200
gaggccgtgc caattttctc tgaaataaca cgcctgcgca agtccatgcc ccaatacect   1260 gtgggccatc ttcaacacat tgcggccctg cgggaagaac ttgggtctaa gctgccgggc   1320
gtgtacatag cgggcgccgg ttacgagggt gtcgggttgc ctgactgtat tagacaggca   1380
aaggaaatgt ccgtgcaagc aacccaagaa cttgctgctg actga                   1425
```

<210> SEQ ID NO 66
<211> LENGTH: 1413
<212> TYPE: DNA
<213> ORGANISM: Artificial Sequence
<220> FEATURE:
<223> OTHER INFORMATION: Recombinant

<400> SEQUENCE: 66

```
atgagtgacg gtaagaagca tttggtcatc atcggcggcg gcatcaccgg cttagcctcc    60
gccttctaca tggaaaagga gattcgggag aagaaccttc ccttgtcagt taccctggtg   120
gaggcctcgc cacgggtcgg gggtaaaatc cagacggccc ggaaggatgg ttatattatc   180
gagcgcggac ccgactcgtt cctcgagcgc aagaagagcg cacccgaact cgttgaggac   240
cttggcctcg aacatctcct cgttaacaat gcaactggtc agtcgtacgt cctggtcaac   300
gagacactcc atcccatgcc caagggcgcg gtgatgggca ttccgacgaa gattgcccct   360
tttatgtcga ctggccttt cagcttctcg ggaaaggccc gtgccgctat ggacttcgtc    420
ctccctgcct cgaaaccgaa ggaggaccag tctcttggag aattttttag gcgcagagtg    480
ggggacgagg ttgtggagaa tctgatcgaa ccgcttctga gcggaatcta tgcgggcgac    540
attgaccgcc tctcactcat gagcaccttc ccacaattct accagacgga gcagaagcat    600
cggtcactca tcctggggat gaaaaaaccc ggcctcaag gatcaggaca aaggcttaca     660
gctaaaaagc aggggcagtt tcaaactctc aagacgggcc tgcagactct agtcgaggag    720
ttagaaaacc agttgaagtt gaccaaggta tacaagggca cgaaagtgac aaacatcagc    780
cggggcgaaa agggttgttc aatcgcgttg gacaacggca tgaccctgga cgcagacgca    840
gcaatcgtga catcgcccca caagagtgct gcgggcatgt tccctgatct gccggcggtc    900
agccagctta aggatatgca ctcaacctcg gtggctaacg tggccttggg cttccctcag    960
gaggccgtcc aaatggagca cgaaggaacc ggctttgtta tcagccgtaa cagtgacttc   1020
tcgattaccg cttgtacctg gacgaacaag aagtggcctc acagcgcgcc agaagggaag   1080
accctcctgc gagcctacgt cggcaaggct ggtgacgagt cgatcgttga gttgtctgac   1140
```

| | |
|---|---:|
| aacgagatta tcaagatcgt acttgaagat ctcaagaagg tcatgaagat aaagggtgaa | 1200 |
| cccgagatga cttgcgttac tagatggaac gagtctatgc ctcagtatca cgtggggcac | 1260 |
| aagcagagga tcaagaaggt ccgggaggcc ttggctgcct cgtatccggg agtctacatg | 1320 |
| accggggcct catttgaggg agtcggtatc cccgactgca tcgaccaagg aaagtccgcc | 1380 |
| gtctctgacg tgttggctta tctattcggc tag | 1413 |

<210> SEQ ID NO 67
<211> LENGTH: 1413
<212> TYPE: DNA
<213> ORGANISM: Artificial Sequence
<220> FEATURE:
<223> OTHER INFORMATION: Recombinant

<400> SEQUENCE: 67

| | |
|---|---:|
| atgagcgacg gaaagaaaca tctcgtgatc atcgggggcg gaataacagg cctagcctcg | 60 |
| gcattctaca tggagaagga gatcagagag aaaaaacctcc cgctctctgt gaccctggtg | 120 |
| gaggcttcac cgagagtggg cgggaagata cagacgcgc gcaaggatgg ctacataata | 180 |
| gagcggggcc cagattcttt cctggagaga aaaaaagcg ccccggaatt ggtggaggac | 240 |
| ctcggcctcg aacacctcct ggtgaataac gcaacagggc aaagctacgt actcgttaat | 300 |
| gagactctcc accccatgcc aaaggggcc gtgatgggaa tccccacaaa gatcgctcca | 360 |
| ttcatgagca ccaggttatt ctctttctct ggtaaagcta gggcagccat ggacttcgtc | 420 |
| ctgccagcct ccaaaccgaa agaagaccaa agcctcgggg aattcttccg ccggagggtg | 480 |
| ggcgacgagg tggttgagaa tttaattgaa cctctcctct caggtatata cgcaggggac | 540 |
| atcgaccgct tgtcgctgat gagcaccttt ccgcagttct accagacgga gcagaagcat | 600 |
| cgctcactca ttcttggtat gaagaagact cgtccgcaag gtctggcca gcagctgaca | 660 |
| gccaagaaac aggggcagtt ccaaactctt aagaccggcc tacagactct ggtggaggag | 720 |
| ctcgagaacc agctgaagct cacaaaggtt tacaagggca caaaggtgac aaacatctca | 780 |
| aggggggaga agggttgctc catcgcgctc gataacggca tgacactcga tgctgatgcg | 840 |
| gcgatagtaa ctagcccgca caagtcggcc gcgggaatgt tccccgacct ccccgcggtc | 900 |
| tcgcaactga aggacatgca ttccaccagc gtcgccaacg tagctctagg cttttcctcag | 960 |
| gaggcagtcc aaatggaaca cgagggcacg ggtttcgtaa tctcccgcaa cagcgacttc | 1020 |
| tcaatcactg cttgcacgtg gactaacaag aagtggccgc attcggcccc cgagggcaag | 1080 |
| acgcttcttc gagcatacgt gggtaaggct ggtgatgaga gtatcgtcga gctctcggac | 1140 |
| aacgagatca ttaagatcgt gttggaggac ttgaagaagg tgatgaaaat caaggggag | 1200 |
| ccggaaatga cttgcgtgac tcgctggaac gagagcatgc cgcagtacca cgttgggcat | 1260 |
| aagcagagga taagaaagt tcgcgaagcg ctggccgcgt cttaccctgg agtgtatatg | 1320 |
| acggagcct cctttgaggg tgtggggatc ccggactgca tcgaccaggg aaagtcagct | 1380 |
| gtctccgacg tgctggccta cttattcgag tga | 1413 |

<210> SEQ ID NO 68
<211> LENGTH: 1428
<212> TYPE: DNA
<213> ORGANISM: Artificial Sequence
<220> FEATURE:
<223> OTHER INFORMATION: Recombinant

<400> SEQUENCE: 68

| | |
|---|---:|
| aagaagattg cagtcattgg tggtgggata acagggttgt ccgtggccta ctacgtgagg | 60 |

```
aagctgcttc gggagcaagg cgttaatgcg ggcgttaccc tcgtcgagca atccgaccgc    120
ctcggcggga agattagatc cttgagacga gacggcttta ccattgagca aggccctgac    180
tctatgattg cacgtaagcc cgcagctctc gaacttatcc gtgagcttgg tctggaggac    240
aagttggcgc gcacaaaccc tcaagccaaa cgctcctaca tactgcaccg tggcaagttt    300
catccgatgc cacctgggct gatgctcggg attcccactc aaatgtggcc aatggtcaag    360
accgggctgc tatctccggc cggaaagcta cgggctgcga tggacctact tcttcctgca    420
aggcgcggag gcggcgacga atcacttggt gggtttatcc ggaggcggct tggacgtgag    480
gtgttggagc agatgaccga accactcctt gctggaatct atgctggcga cacagaacag    540 cttttcactta aagcgacctt tcctcaattc atggagatgg aaaggaaaca tcgcagtctc    600
atccttggac tattggctgg gaagaaacag ccaccgcgtc ccggtggtag ccaagtgccg    660
ctcccaaagg ccgctcagac cagtatgttc ttgacactca ccggcgggtt ggaaggtctg    720
accgaagcac tagaggaaag cctatcagag gagaagataa ttactggcca agcagttacc    780
ggactttcgc agcaagaggc cgggtatgag ttaaatctct ctggcggaga gagacttaat    840
gcagacggag tgatcctcgc agtcccagcg ttcgctgccg cccgacttct tgacggcgtg    900
cctgaggccg cctacctaga gcgcatccgc tatgtcagtg ttgctaattt ggcgttcgct    960
tacaggcgtg aggacgtgcc tcatgatctg aatgggtccg gcgtgttaat ccctagaggt   1020
gaagggagga tgattacggc cataacttgg gtttcgtcca aatggttgca ttcagcaccc   1080
ggtgacaagg cactgctgag agcgtacatt gggcgactag gtgatgaggc ttggacagcc   1140
atgtgtaggg ccgacatcga gcgtagagtc gccgctgaac tccgcgatct actaggaatt   1200
gccgctagtc ctttgttctg tgaactagcc gcactcccag aatctatgcc gcagtatcca   1260
gtgggtcacg tcgaacgact cgaagccttg cgaggagcat tgtgtcgcgc taaaccaggg   1320
ttgttgttgt gtggtgccgg gtacgctggc gttggcattc cagactgcat tcggcaaggc   1380
aaagaagccg ctgagtcgat ggcggcttat ttgagggacg gacgctag             1428
```

<210> SEQ ID NO 69
<211> LENGTH: 1470
<212> TYPE: DNA
<213> ORGANISM: Artificial Sequence
<220> FEATURE:
<223> OTHER INFORMATION: Recombinant

<400> SEQUENCE: 69

```
aggaaacttg tggtcatcgg cggagggatc actgggcttt cggccgcctt ctatgcacta     60
aagcaagccg atgaggaagg gcagcccatc tcggtcacca taattgaaca gagcgatagg    120
ctcggcggaa agatccagac actccgcaag agggctgcg taattgagaa gggcccggat    180
tccttcctcg ctaggaagtt gccgatgatt gatctagctc gggatcttgg catggactcc    240
gaattggtgg cgactaatcc gcacgcaaag aagacttaca tcttgaggcg cggaaagctc    300
taccggatgc ctccaggctt agtgcttggc ataccctacgg aactaggacc attcgctaag    360
acagggctca ttagcccttg gggcaaactc cgcgccgcta tggatttgtt cattaagcct    420
catccagccg atgaagacga aagtgttggc gctttcctgg acagacgtct cggtagggaa    480
gtgaccgagc acattgcgga acctttattg gcgggcatct acgcgggcga cttgcaagcc    540
ttaagccttc aagccacttt cccacagttt gcacaagtag agcgcaagca cggagggctg    600
atacgcggta tgaaggccag cagacaggcc ggtcagtccg tgcctgggct gccggacgtc    660
```

| | |
|---|---|
| gccaagggta cgatgttcct tacctttcgc aacgggctta ccagcttagt tgaaaggttg | 720 |
| gaggaaactc tcagagacag ggctgaactc tgtctgggca tcggcgcaga agggtttgag | 780 |
| aaacgtgaag atggaacata ccttgttcga ctaagcgatg gttcgaggct ccaggccgac | 840 |
| gcagtaattg tcactacgcc gagctatcat gcggcatccc tgttggagga gcatgtggat | 900 |
| gcttcggccc tccaggccat tcgtcatgta agcgttgcaa atgtcgttag cgtcttcgac | 960 |
| cgaaagcaag tgaataacca gttcgacggc acagggtttg ttatctcacg gcagaaggt | 1020 |
| cgcgcaatca ccgcctgtac ctggacatcc gtgaaatggc cgcatacttc gcgcggcgac | 1080 |
| aaactgatta tccggtgcta catcggtagg gctggcgacg aggagcgagt ggattggccc | 1140 |
| gatgaagctc tcaagcgtac tgtaagatca gaactgcgtg agttgctgga cattgacatt | 1200 |
| gatccggaat ttgtggagat tacacgactc aggcactcta tgcctcaata cccagtcggc | 1260 |
| cacgtccagg ctatccgctc tttgagggac gaggtcggta ggactttacc gggcgtgttc | 1320 |
| cttgctgggc aaccctacga aggtgtggga atgcctgact gtgtgaggtc cggccgggat | 1380 |
| gccgccaag cagcagtaag tgctatgcaa gcaatgagta cagaaccaga agcaccggca | 1440 |
| gaggacgccg ctactggaac ggcgggttga | 1470 |

<210> SEQ ID NO 70
<211> LENGTH: 1410
<212> TYPE: DNA
<213> ORGANISM: Artificial Sequence
<220> FEATURE:
<223> OTHER INFORMATION: Recombinant

<400> SEQUENCE: 70

| | |
|---|---|
| cggagagttg ttgttgttgg cggcggcttg actggcctaa gcgccgcctt ctacatccgg | 60 |
| aaacattatc gagaagctgg agttgagccc gtcatcacgc ttgttgagaa atctagctcg | 120 |
| atgggaggga tgattgagac ccttcatagg gacgggtttg tcatcgagaa gggcccggac | 180 |
| agtttcttgg cacggaagac cgcaatgatt gatctggcga aagagctgga gattgaccac | 240 |
| gagttggtca gccagaatcc agaatcgaag aagacctaca taatgcaacg tggaaagctg | 300 |
| caccctatgc cagcgggact tgttctgggc attcccaccg aattgcgtcc ctttctccgg | 360 |
| agcgggcttg tctcacccgc tgggaagttg cgggcgctga tggacttcgt aataccgcca | 420 |
| cgaaggacga ccgaagatga gtcactcggg tacatgatcg agcgccgact gggtgccgag | 480 |
| gtgttggaga acctcacaga gccgttgctc gctggaatct acgctggcga catgagaaga | 540 |
| ttgtccctcc aggctacgtt tccgcagttc ggtgaggtgg agcgcgacta cggctcctta | 600 |
| atcagaggaa tgatgaccgg acgtaagcct gcggagacac acacagggac caagaggtct | 660 |
| gcctttctca atttcagaca gggtctgcaa tcactggttc acgccttagt ccatgaactc | 720 |
| caggatgtag atcagaggtt aaatactgcg gtgaagtcgc ttcagaggct tgacggcgca | 780 |
| caaacccgtt atcgcgttga actcggcaat ggcgaaatgc ttgaggctga cgacgtggtg | 840 |
| gttactgtac caacctacgt ggcgagcgag cttcttaagc cgcacgtgga cacggcggcg | 900 |
| ttagacgcta ttaactatgt gtcggtggct aatgtagttc ttgcattcga gaagaaggaa | 960 |
| gtagagcacg tcttcgatgg atcggcttc ttggtgcctc ggaaggaggg aaggaacata | 1020 |
| accgcctgca cctggacttc gaccaagtgg ctccacacat caccagatga caaggttctg | 1080 |
| ttacgttgtt acgtgggcag aagtggagat gagcagaatg tggaactccc ggatgaggca | 1140 |
| ctcactaatc tggtgcttaa ggatctgaga gagacgatgg gcatcgaggc ggttccaatc | 1200 |
| ttctcagaga ttacccggct ccgcaagtca atgccgcagt acccagtagg acatctccag | 1260 |

| | |
|---|---|
| cacatcgccg cattgcgcga ggaactcggc tctaagctac caggagtgta catcgccgga | 1320 |
| gcgggctacg agggcgttgg tcttccggat tgcattcgcc aggccaaaga aatgtcagtc | 1380 |
| caggcaacgc aagaactcgc tgccgactga | 1410 |

<210> SEQ ID NO 71
<211> LENGTH: 1398
<212> TYPE: DNA
<213> ORGANISM: Artificial Sequence
<220> FEATURE:
<223> OTHER INFORMATION: Recombinant

<400> SEQUENCE: 71

| | |
|---|---|
| aagcacctgg taatcatcgg tggtgggatc accggtctgg cttcagcgtt ctacatggaa | 60 |
| aaggagatcc gggagaagaa cttgccccct tcggtgactc tagtggaggc ctctccacgg | 120 |
| gtgggggggca agattcagac cgcgcgcaag gatggctaca tcatagagcg aggaccagac | 180 |
| tcattcctag agcgtaagaa gtccgcccca gagctcgtcg aggatctcgg tctagagcac | 240 |
| ttgctagtga ataacgctac aggacagtcc tacgtgctcg tgaacgagac actacacccg | 300 |
| atgcctaagg gggctgtcat gggtataccg accaagatcg ccccgttcat gtccactcgc | 360 |
| cttttctcgt tctcgggcaa agctcgggcc gctatggatt tcgtcttgcc tgcctcgaaa | 420 |
| ccgaaggagg accagtcctt aggagagttc ttccgccgga gggtcggcga cgaggtggtg | 480 |
| gagaacttaa tcgaacccct gctctcgggg atctacgctg gagacattga tcgactatcg | 540 |
| cttatgtcta cgtttcctca attttaccag acggagcaga agcaccgtag cctcattttg | 600 |
| ggtatgaaga agacacggcc tcaaggttcg gggcagcagc ttactgccaa gaagcagggc | 660 |
| caattccaga cactcaagac cggcttgcag actctagtgg aggagctgga gaatcaattg | 720 |
| aagctgacaa aggtctacaa gggtaccaag gtgacaaaca tatcgcgtgg cgaaaaggga | 780 |
| tgctccattg ccctcgacaa cggtatgacc ctcgacgccg acgcagcgat tgtgacgagc | 840 |
| ccacacaaga gcgccgcggg catgttcccg gacttgcctg cagtgtcaca gctgaaagac | 900 |
| atgcattcta catccgtcgc caacgtcgcc ctgggctttc cccaggaggc tgtgcagatg | 960 |
| gagcacgagg ggacgggctt cgttatcagc cgcaactccg acttttctat taccgcgtgc | 1020 |
| acatggacca acaagaagtg gccgcacagc gctccggagg ggaaaacact tctccgagca | 1080 |
| tacgtaggca aggccgggga cgagtcaatt gttgagctct ccgacaatga aatcattaaa | 1140 |
| atagttctgg aggatcttaa gaaggtaatg aagataaagg gggaacctga aatgacgtgt | 1200 |
| gttacccgct ggaatgagtc aatgcccag taccatgtgg acacaagca gaggataaag | 1260 |
| aaggtgaggg aggcgctcgc tgcgtcctac ccagggtct acatgacagg agcgagtttt | 1320 |
| gaggggggtgg gtattcccga ctgtatcgac cagggtaagt cggcagtgtc tgacgtgctc | 1380 |
| gcttacctat tcgagtag | 1398 |

<210> SEQ ID NO 72
<211> LENGTH: 1422
<212> TYPE: DNA
<213> ORGANISM: Artificial Sequence
<220> FEATURE:
<223> OTHER INFORMATION: Recombinant

<400> SEQUENCE: 72

| | |
|---|---|
| attgcagtca ttggtggtgg gataacaggg ttgtccgtgg cctactacgt gaggaagctg | 60 |
| cttcgggagc aaggcgttaa tgcgggcgtt accctcgtcg agcaatccga ccgcctcggc | 120 |

| | |
|---|---|
| gggaagatta gatccttgag acgagacggc tttaccattg agcaaggccc tgactctatg | 180 |
| attgcacgta agcccgcagc tctcgaactt atccgtgagc ttggtctgga ggacaagttg | 240 |
| gcgggcacaa accctcaagc caaacgctcc tacatactgc accgtggcaa gtttcatccg | 300 |
| atgccacctg ggctgatgct cgggattccc actcaaatgt ggccaatggt caagaccggg | 360 |
| ctgctatctc cggccggaaa gctacgggct gcgatggacc tacttcttcc tgcaaggcgc | 420 |
| ggaggcggcg acgaatcact tggtgggttt atccggaggc ggcttggacg tgaggtgttg | 480 |
| gagcagatga ccgaaccact ccttgctgga atctatgctg gcgacacaga acagctttca | 540 |
| cttaaagcga cctttcctca attcatggag atggaaagga acatcgcag tctcatcctt | 600 |
| ggactattgg ctgggaagaa acagccaccg cgtcccggtg gtagccaagt gccgctccca | 660 |
| aaggccgctc agaccagtat gttcttgaca ctcaccggcg ggttggaagg tctgaccgaa | 720 |
| gcactagagg aaagcctatc agaggagaag ataattactg gccaagcagt taccggactt | 780 |
| tcgcagcaag aggccgggta tgagttaaat ctctctggcg gagagagact taatgcagac | 840 |
| ggagtgatcc tcgcagtccc agcgttcgct gccgcccgac ttcttgacgg cgtgcctgag | 900 |
| gccgcctacc tagagcgcat ccgctatgtc agtgttgcta atttggcgtt cgcttacagg | 960 |
| cgtgaggacg tgcctcatga tctgaatggg tccggcgtgt taatccctag aggtgaaggg | 1020 |
| aggatgatta cggccataac ttgggttttcg tccaaatggt tgcattcagc acccggtgac | 1080 |
| aaggcactgc tgagagcgta cattgggcga ctaggtgatg aggcttggac agccatgtgt | 1140 |
| agggccgaca tcgagcgtag agtcgccgct gaactccgcg atctactagg aattgccgct | 1200 |
| agtcctttgt tctgtgaact agccgcactc ccagaatcta tgccgcagta tccagtgggt | 1260 |
| cacgtcgaac gactcgaagc cttgcgagga gcattgtgtc gcgctaaacc agggttgttg | 1320 |
| ttgtgtggtg ccgggtacgc tggcgttggc attccagact gcattcggca aggcaaagaa | 1380 |
| gccgctgagt cgatggcggc ttatttgagg gacggacgct ag | 1422 |

<210> SEQ ID NO 73
<211> LENGTH: 1464
<212> TYPE: DNA
<213> ORGANISM: Artificial Sequence
<220> FEATURE:
<223> OTHER INFORMATION: Recombinant

<400> SEQUENCE: 73

| | |
|---|---|
| cttgtggtca tcggcggagg gatcactggg cttttcggccg ccttctatgc actaaagcaa | 60 |
| gccgatgagg aagggcagcc catctcggtc accataattg aacagagcga taggctcggc | 120 |
| ggaaagatcc agacactccg caaggagggc tgcgtaattg agaagggccc ggattccttc | 180 |
| ctcgctagga agttgccgat gattgatcta gctcgggatc ttggcatgga ctccgaattg | 240 |
| gtggcgacta atccgcacgc aaagaagact tacatcttga ggcgcggaaa gctctaccgg | 300 |
| atgcctccag gcttagtgct tggcataccct acggaactag gaccattcgc taagacaggg | 360 |
| ctcattagcc cttgggcaa actccgcgcc gctatggatt tgttcattaa gcctcatcca | 420 |
| gccgatgaag acgaaagtgt tggcgctttc ctggacagac gtctcggtag ggaagtgacc | 480 |
| gagcacattg cggaaccttt attggcgggc atctacgcgg gcgacttgca agccttaagc | 540 |
| cttcaagcca cttctcccaca gtttgcacaa gtagagcgca agcacggagg gctgatacgc | 600 |
| ggtatgaagg ccagcagaca ggccggtcag tccgtgcctg ggctgccgga cgtcgccaag | 660 |
| ggtacgatgt tccttacctt tcgcaacggg cttaccagct tagttgaaag gttggaggaa | 720 |
| actctcagag acagggctga actctgtctg ggcatcggcg cagaagggtt tgagaaacgt | 780 |

| | |
|---|---|
| gaagatggaa cataccttgt tcgactaagc gatggttcga ggctccaggc cgacgcagta | 840 |
| attgtcacta cgccgagcta tcatgcggca tccctgttgg aggagcatgt ggatgcttcg | 900 |
| gccctccagg ccattcgtca tgtaagcgtt gcaaatgtcg ttagcgtctt cgaccgaaag | 960 |
| caagtgaata accagttcga cggcacaggg tttgttatct cacggcgaga aggtcgcgca | 1020 |
| atcaccgcct gtacctggac atccgtgaaa tggccgcata cttcgcgcgg cgacaaactg | 1080 |
| attatccggt gctacatcgg tagggctggc gacgaggagc gagtggattg cccgatgaa | 1140 |
| gctctcaagc gtactgtaag atcagaactg cgtgagttgc tggacattga cattgatccg | 1200 |
| gaatttgtgg agattacacg actcaggcac tctatgcctc aatacccagt cggccacgtc | 1260 |
| caggctatcc gctctttgag ggacgaggtc ggtaggactt taccgggcgt gttccttgct | 1320 |
| gggcaaccct acgaaggtgt gggaatgcct gactgtgtga ggtccggccg ggatgccgcc | 1380 |
| gaagcagcag taagtgctat gcaagcaatg agtacagaac cagaagcacc ggcagaggac | 1440 |
| gccgctactg aacggcggg ttga | 1464 |

<210> SEQ ID NO 74
<211> LENGTH: 1404
<212> TYPE: DNA
<213> ORGANISM: Artificial Sequence
<220> FEATURE:
<223> OTHER INFORMATION: Recombinant

<400> SEQUENCE: 74

| | |
|---|---|
| gttgttgttg ttggcggcgg cttgactggc ctaagcgccg ccttctacat ccggaaacat | 60 |
| tatcgagaag ctggagttga gcccgtcatc acgcttgttg agaaatctag ctcgatggga | 120 |
| gggatgattg agaccttca tagggacggg tttgtcatcg agaagggccc ggacagtttc | 180 |
| ttggcacgga agaccgcaat gattgatctg gcgaaagagc tggagattga ccacgagttg | 240 |
| gtcagccaga atccagaatc gaagaagacc tacataatgc aacgtggaaa gctgcacct | 300 |
| atgccagcgg gacttgttct gggcattccc accgaattgc gtcccttct ccggagcggg | 360 |
| cttgtctcac ccgctgggaa gttgcggcg ctgatggact tcgtaatacc gccacgaagg | 420 |
| acgaccgaag atgagtcact cgggtacatg atcgagcgcc gactgggtgc cgaggtgttg | 480 |
| gagaacctca cagagccgtt gctcgctgga atctacgctg gcgacatgag aagattgtcc | 540 |
| ctccaggcta cgtttccgca gttcggtgag gtggagcgcg actacggctc cttaatcaga | 600 |
| ggaatgatga ccggacgtaa gcctgcggag acacacacag ggaccaagag gtctgccttt | 660 |
| ctcaatttca gacagggtct gcaatcactg gttcacgcct tagtccatga actccaggat | 720 |
| gtagatcaga ggttaaatac tgcggtgaag tcgcttcaga ggcttgacgg cgcacaaacc | 780 |
| cgttatcgcg ttgaactcgg caatggcgaa atgcttgagg ctgacgacgt ggtggttact | 840 |
| gtaccaacct acgtggcgag cgagcttctt aagccgcacg tggacacggc ggcgttagac | 900 |
| gctattaact atgtgtcggt ggctaatgta gttcttgcat tcgagaagaa ggaagtagag | 960 |
| cacgtcttcg atggatcggg cttcttggtg cctcggaagg agggaaggaa cataaccgcc | 1020 |
| tgcacctgga cttcgaccaa gtggctccac acatcaccag atgacaaggt tctgttacgt | 1080 |
| tgttacgtgg gcagaagtgg agatgagcag aatgtggaac tcccggatga ggcactcact | 1140 |
| aatctggtgc ttaaggatct gagagagacg atgggcatcg aggcggttcc aatcttctca | 1200 |
| gagattaccc ggctccgcaa gtcaatgccg cagtacccag taggacatct ccagcacatc | 1260 |
| gccgcattgc gcgaggaact cggctctaag ctaccaggag tgtacatcgc cggagcgggc | 1320 | tacgagggcg ttggtcttcc ggattgcatt cgccaggcca agaaatgtc agtccaggca 1380 acgcaagaac tcgctgccga ctga 1404

<210> SEQ ID NO 75
<211> LENGTH: 1398
<212> TYPE: DNA
<213> ORGANISM: Artificial Sequence
<220> FEATURE:
<223> OTHER INFORMATION: Recombinant

<400> SEQUENCE: 75
aagcacctgg taatcatcgg tggtgggatc accggtctgg cttcagcgtt ctacatggaa 60
aaggagatcc gggagaagaa cttgcccctt cggtgactc tagtggaggc ctctccacgg 120 gtgggggca agattcagac cgcgcgcaag gatggctaca tcatagagcg aggaccagac 180
tcattcctag agcgtaagaa gtccgcccca gagctcgtcg aggatctcgg tctagagcac 240
ttgctagtga ataacgctac aggacagtcc tacgtgctcg tgaacgagac actcacccg 300 atgcctaagg gggctgtcat gggtataccg accaagatcg ccccgttcat gtccactcgc 360
cttttctcgt tctcgggcaa agctcgggcc gctatggatt tcgtcttgcc tgcctcgaaa 420
ccgaaggagg accagtcctt aggagagttc ttccgccgga gggtcggcga cgaggtggtg 480
gagaacttaa tcgaacccct gctctcgggg atctacgctg agacattga tcgactatcg 540 cttatgtcta cgtttcctca atttttaccag acggagcaga agcaccgtag cctcattttg 600
ggtatgaaga agacacggcc tcaaggttcg gggcagcagc ttactgccaa gaagcagggc 660
caattccaga cactcaagac cggcttgcag actctagtgg aggagctgga gaatcaattg 720
aagctgacaa aggtctacaa gggtaccaag gtgacaaaca tatcgcgtgg cgaaaaggga 780
tgctccattg ccctcgacaa cggtatgacc ctcgacgccg acgcagcgat gtgtgacgagc 840 ccacacaaga gcgccgcggg catgttcccg gacttgcctg cagtgtcaca gctgaaagac 900
atgcattcta catccgtcgc caacgtcgcc ctgggctttc cccaggaggc tgtgcagatg 960
gagcacgagg ggacgggctt cgttatcagc cgcaactccg actttctat accgcgtgc 1020 acatggacca caagaagtg gccgcacagc gctccggagg ggaaaacact tctccgagca 1080
tacgtaggca aggccgggga cgagtcaatt gttgagctct ccgacaatga aatcattaaa 1140
atagttctgg aggatcttaa gaaggtaatg aagataaagg gggaacctga atgacgtgt 1200 gttacccgct ggaatgagtc aatgccccag taccatgtgg gacacaagca gaggataaag 1260
aaggtgaggg aggcgctcgc tgcgtcctac ccaggggtct acatgacagg agcgagtttt 1320 gaggggtgg gtattcccga ctgtatcgac cagggtaagt cggcagtgtc tgacgtgctc 1380
gcttacctat tcgagtag 1398

<210> SEQ ID NO 76
<211> LENGTH: 181
<212> TYPE: PRT
<213> ORGANISM: Escherichia coli

<400> SEQUENCE: 76

Met Lys Thr Leu Ile Leu Phe Ser Thr Arg Asp Gly Gln Thr Arg Glu
1               5                   10                  15

Ile Ala Ser Tyr Leu Ala Ser Glu Leu Lys Glu Leu Gly Ile Gln Ala
                20                  25                  30

Asp Val Ala Asn Val His Arg Ile Glu Glu Pro Gln Trp Glu Asn Tyr
            35                  40                  45

```
Asp Arg Val Val Ile Gly Ala Ser Ile Arg Tyr Gly His Tyr His Ser
 50                  55                  60
Ala Phe Gln Glu Phe Val Lys Lys His Ala Thr Arg Leu Asn Ser Met
 65                  70                  75                  80
Pro Ser Ala Phe Tyr Ser Val Asn Leu Val Ala Arg Lys Pro Glu Lys
                 85                  90                  95
Arg Thr Pro Gln Thr Asn Ser Tyr Ala Arg Lys Phe Leu Met Asn Ser
            100                 105                 110
Gln Trp Arg Pro Asp Arg Cys Ala Val Ile Ala Gly Ala Leu Arg Tyr
        115                 120                 125
Pro Arg Tyr Arg Trp Tyr Asp Arg Phe Met Ile Lys Leu Ile Met Lys
    130                 135                 140
Met Ser Gly Gly Glu Thr Asp Thr Arg Lys Glu Val Val Tyr Thr Asp
145                 150                 155                 160
Trp Glu Gln Val Ala Asn Phe Ala Arg Glu Ile Ala His Leu Thr Asp
                165                 170                 175
Lys Pro Thr Leu Lys
            180
```

<210> SEQ ID NO 77
<211> LENGTH: 546
<212> TYPE: DNA
<213> ORGANISM: Escherichia coli

<400> SEQUENCE: 77

```
gtgaaaacat taattctttt ctcaacaagg gacggacaaa cgcgcgagat tgcctcctac      60
ctggcttcgg aactgaaaga actggggatc caggcggatg tcgccaatgt gcaccgcatt     120
gaagaaccac agtgggaaaa ctatgaccgt gtggtcattg gtgcttctat tcgctatggt     180
cactaccatt cagcgttcca ggaatttgtc aaaaaacatg cgacgcggct gaattcgatg     240
ccgagcgcct tttactccgt gaatctggtg gcgcgcaaac cggagaagcg tactccacag     300
accaacagct acgcgcgcaa gtttctgatg aactcgcaat ggcgtcccga tcgctgcgcg     360
gtcattgccg gggcgctgcg ttacccacgt tatcgctggt acgaccgttt tatgatcaag     420
ctgattatga agatgtcagg cggtgaaacg gatacgcgca agaagttgt ctataccgat      480
tgggagcagg tggcgaattt cgcccgagaa atcgcccatt taaccgacaa accgacgctg     540
aaataa                                                                546
```

<210> SEQ ID NO 78
<211> LENGTH: 546
<212> TYPE: DNA
<213> ORGANISM: Artificial Sequence
<220> FEATURE:
<223> OTHER INFORMATION: Recombinant

<400> SEQUENCE: 78

```
atgaagacct tgattctatt ctccacaagg gacggccaga ctagggagat cgcttcctac      60
ctggccagcg agctaaagga gcttggcatt caggcagacg tggctaacgt gcaccgaatt     120
gaggagccgc agtgggagaa ctacgatcgg gtcgtgatcg gcgccagcat ccggtatgga     180
cactaccaca gcgcgttcca ggagttcgtg aaaaagcacg cgacccgtct gaatagcatg     240
ccatcagcgt tctactcggt caacctcgtg gctcgtaagc ccgagaagcg gacaccccag     300
accaactcgt atgccaggaa gttccttatg aactcgcagt ggcgaccgga ccgctgcgcg     360
gtgatcgccg gtgcgctcag gtaccctcgt tataggtggt acgacaggtt tatgattaaa     420
```

```
cttataatga aaatgagcgg cggagagacc gacaccagaa agaggtggt ttacacagac    480 tgggagcagg tagcaaactt cgctagggag attgctcacc tcaccgacaa gccgaccttg   540
aagtaa                                                              546
```

<210> SEQ ID NO 79
<211> LENGTH: 546
<212> TYPE: DNA
<213> ORGANISM: Artificial Sequence
<220> FEATURE:
<223> OTHER INFORMATION: Recombinant

<400> SEQUENCE: 79

```
atgaaaaccc taatactgtt ctcgacccgc gacggccaga cgcgtgagat tgcgagctac    60
ctggcctccg agctcaagga gctgggatc caagccgatg tcgcgaacgt gcaccgcatt    120
gaggagccgc agtgggagaa ttacgatcgc gttgtgatag gggccagcat ccgctatggc   180
cactaccact cggcctttca ggagtttgta aagaaacacg ccacaagatt aaactccatg   240
cctagcgcct tctactccgt caaccttgtc gcgcgcaagc cggagaagcg gacacctcag   300
acgaactcct acgcgcggaa gttcctgatg aacagccagt ggcggccgga cagatgtgct   360
gttattgcgg gagccctgag atacccgagg taccggtggt acgataggtt tatgattaaa   420
cttattatga gatgtctgg tggggagact gacaccagga aggaggtggt atatacagac    480
tgggagcagg tcgccaattt cgctcgggaa atcgcgcatc tgacagacaa gcctacactg   540
aagtag                                                              546
```

<210> SEQ ID NO 80
<211> LENGTH: 504
<212> TYPE: PRT
<213> ORGANISM: Amaranthus tuberculatus

<400> SEQUENCE: 80

```
Met Gly Asn Ile Ser Glu Arg Glu Pro Thr Ser Ala Lys Arg Val
1               5                   10                  15

Ala Val Val Gly Ala Gly Val Ser Gly Leu Ala Ala Ala Tyr Lys Leu
            20                  25                  30

Lys Ser His Gly Leu Ser Val Thr Leu Phe Glu Ala Asp Ser Arg Ala
        35                  40                  45

Gly Gly Lys Leu Lys Thr Val Lys Lys Asp Gly Phe Ile Trp Asp Glu
    50                  55                  60

Gly Ala Asn Thr Met Thr Glu Ser Glu Ala Glu Val Ser Ser Leu Ile
65                  70                  75                  80

Asp Asp Leu Gly Leu Arg Glu Lys Gln Gln Leu Pro Ile Ser Gln Asn
                85                  90                  95

Lys Arg Tyr Ile Ala Arg Asp Gly Leu Pro Val Leu Leu Pro Ser Asn
            100                 105                 110

Pro Ala Ala Leu Leu Thr Ser Asn Ile Leu Ser Ala Lys Ser Lys Leu
        115                 120                 125

Gln Ile Met Leu Glu Pro Phe Leu Trp Arg Lys His Asn Ala Thr Glu
    130                 135                 140

Leu Ser Asp Glu His Val Gln Glu Ser Val Gly Glu Phe Phe Glu Arg
145                 150                 155                 160

His Phe Gly Lys Glu Phe Val Asp Tyr Val Ile Asp Pro Phe Val Ala
                165                 170                 175

Gly Thr Cys Gly Gly Asp Pro Gln Ser Leu Ser Met His His Thr Phe
            180                 185                 190
```

Pro Glu Val Trp Asn Ile Glu Lys Arg Phe Gly Ser Val Phe Ala Gly
        195                 200                 205

Leu Ile Gln Ser Thr Leu Leu Ser Lys Lys Glu Lys Gly Gly Glu Asn
    210                 215                 220

Ala Ser Ile Lys Lys Pro Arg Val Arg Gly Ser Phe Ser Phe Gln Gly
225                 230                 235                 240

Gly Met Gln Thr Leu Val Asp Thr Met Cys Lys Gln Leu Gly Glu Asp
                245                 250                 255

Glu Leu Lys Leu Gln Cys Glu Val Leu Ser Leu Ser Tyr Asn Gln Lys
            260                 265                 270

Gly Ile Pro Ser Leu Gly Asn Trp Ser Val Ser Met Ser Asn Asn
        275                 280                 285

Thr Ser Glu Asp Gln Ser Tyr Asp Ala Val Val Thr Ala Pro Ile
    290                 295                 300

Arg Asn Val Lys Glu Met Lys Ile Met Lys Phe Gly Asn Pro Phe Ser
305                 310                 315                 320

Leu Asp Phe Ile Pro Glu Val Thr Tyr Val Pro Leu Ser Val Met Ile
                325                 330                 335

Thr Ala Phe Lys Lys Asp Lys Val Lys Arg Pro Leu Glu Gly Phe Gly
            340                 345                 350

Val Leu Ile Pro Ser Lys Glu Gln His Asn Gly Leu Lys Thr Leu Gly
        355                 360                 365

Thr Leu Phe Ser Ser Met Met Phe Pro Asp Arg Ala Pro Ser Asp Met
    370                 375                 380

Cys Leu Phe Thr Thr Phe Val Gly Gly Ser Arg Asn Arg Lys Leu Ala
385                 390                 395                 400

Asn Ala Ser Thr Asp Glu Leu Lys Gln Ile Val Ser Ser Asp Leu Gln
                405                 410                 415

Gln Leu Leu Gly Thr Glu Asp Glu Pro Ser Phe Val Asn His Leu Phe
            420                 425                 430

Trp Ser Asn Ala Phe Pro Leu Tyr Gly His Asn Tyr Asp Ser Val Leu
        435                 440                 445

Arg Ala Ile Asp Lys Met Glu Lys Asp Leu Pro Gly Phe Phe Tyr Ala
    450                 455                 460

Gly Asn His Lys Gly Gly Leu Ser Val Gly Lys Ala Met Ala Ser Gly
465                 470                 475                 480

Cys Lys Ala Ala Glu Leu Val Ile Ser Tyr Leu Asp Ser His Ile Tyr
                485                 490                 495

Val Lys Met Asp Glu Lys Thr Ala
            500

<210> SEQ ID NO 81
<211> LENGTH: 1515
<212> TYPE: DNA
<213> ORGANISM: Artificial Sequence
<220> FEATURE:
<223> OTHER INFORMATION: Recombinant

<400> SEQUENCE: 81
atgggcaaca ttagcgaacg cgaagaaccg accagcgcga aacgcgtggc ggtggtgggc    60
gcgggcgtga gcggcctggc ggcggcgtat aagctgaaga gccatggact gagtgtaacc   120
ctgttcgaag cggatagccg cgcaggcggc aagctgaaga ccgtgaagaa ggatggcttc   180
atatgggatg aaggcgcgaa caccatgacc gagagcgagg cggaggtgag cagtctgata   240

-continued

```
gatgatcttg gccttcgcga gaagcagcaa ctgccgatta gccagaacaa acgctatatt    300
gcgcgcgatg gcctgccggt gctgctgccg agcaacccgg cggcgctgct gaccagcaac    360
attctgagcg cgaaaagcaa actgcagatt atgctggaac cgtttctgtg gcgcaaacat    420
aacgcgaccg aactgagcga tgaacatgtg caggaaagcg tgggcgaatt ttttgaacgc    480
cattttggca aagaatttgt ggattatgtg attgatccgt ttgtggcggg cacctgcggc    540
ggcgatccgc agagcctgag catgcatcat acctttccgg aagtgtggaa cattgaaaaa    600
cgctttggca gcgtgtttgc gggcctgatt cagagcacgc tgctgagcaa gaaagagaaa    660
ggaggcgaga acgcgagcat taaaaaaccg cgcgtgcgcg gcagctttag ctttcagggc    720
ggcatgcaga ccctggtgga taccatgtgc aaacagctgg gcgaagatga actgaaactg    780
cagtgcgaag tgctgagcct gagctataac cagaaaggca ttccgagcct gggcaactgg    840
agcgtgagca gcatgagcaa caacaccagc gaagatcaga gctatgatgc ggtggtggtg    900
accgcgccga ttcgcaacgt gaaagagatg aagattatga agttcggcaa cccgttcagc    960
ctggatttta ttccggaagt gacctatgtg ccgctgagcg tgatgattac cgcgtttaaa   1020
aaagataaag tgaaacgccc gctggaaggc ttcggcgtgc tgataccgag caaggagcag   1080
cacaatggcc ttaagaccct tggcactctg ttcagcagta tgatgttccc ggatcgcgca   1140
ccgagcgata tgtgcctgtt taccaccttt gtgggcggca gccgcaaccg caagctggcg   1200
aacgcgagca ccgatgaact gaagcagatt gtgagcagcg atctgcagca actgctgggc   1260
accgaagatg aaccgagctt tgtgaaccat ctgttctgga gcaacgcgtt tccgctgtat   1320
ggccataact atgatagcgt gctgcgcgca attgataaga tggaaaagga tctgccgggc   1380
ttcttctatg cgggcaacca taaaggcggc ctgagcgtgg gcaaagcgat ggcgagcggc   1440
tgcaaagcgg cggaactggt gattagctat ctggatagcc atatttatgt gaaaatggat   1500
gagaagaccg cgtga                                                    1515
```

METHODS AND COMPOSITIONS FOR PPO HERBICIDE TOLERANCE IN PLANTS

CROSS-REFERENCE TO RELATED APPLICATIONS

This application is a divisional of U.S. application Ser. No. 15/228,993, filed Aug. 4, 2016 (pending), which application claims the benefit of priority of U.S. Provisional Application Ser. No. 62/212,716, filed Sep. 1, 2015, and U.S. Provisional Application Ser. No. 62/323,852, filed Apr. 18, 2016, the disclosures of each of which are hereby incorporated by reference in their entirety.

INCORPORATION OF SEQUENCE LISTING

The sequence listing that is contained in the file named MONS384US_sequence_listing.txt, which is 204 kilobytes (measured in MS-Windows) and created on Aug. 3, 2016, is filed herewith by electronic submission and incorporated herein by reference.

BACKGROUND

Field of the Invention

The present invention relates to the field of biotechnology. More specifically, the invention relates to recombinant DNA molecules encoding enzymes that provide tolerance to herbicides that inhibit protoporphyrinogen oxidase.

Related Art

Agricultural crop production often utilizes transgenic traits created using the methods of biotechnology. A heterologous gene, also known as a transgene, can be introduced into a plant to produce a transgenic trait. Expression of the transgene in the plant confers a trait, such as herbicide tolerance, on the plant. Examples of transgenic herbicide tolerance traits include glyphosate tolerance, glufosinate tolerance, and dicamba tolerance. With the increase of weed species resistant to the commonly used herbicides, new herbicide tolerance traits are needed in the field. Herbicides of particular interest include herbicides that inhibit protoporphyrinogen oxidase (PPO, EC 1.3.3.4), referred to as PPO herbicides. PPO herbicides provide control of a spectrum of herbicide-resistant weeds, thus making a trait conferring tolerance to these herbicides particularly useful in a cropping system combined with one or more other herbicide-tolerance trait(s).

Protoporphyrinogen oxidase functions in both chlorophyll and heme biosynthesis pathways where it converts protoporphyrinogen IX to protoporphyrin IX. Following production of protoporphyrin IX, the chlorophyll and heme biosynthetic pathways diverge with different metal ions being incorporated (iron for heme and magnesium for chlorophyll). Segments of this pathway are conserved across prokaryotes and eukaryotes, and many of the PPO enzymes found across prokaryotes and eukaryotes are relatively similar. Some prokaryotes (e.g., cyanobacteria) use this pathway for chlorophyll and heme production while other prokaryotes (e.g., *Escherichia coli*) use this pathway for heme production.

Herbicide-insensitive protoporphyrinogen oxidases (iPPOs) have been isolated from a number of prokaryotes and eukaryotes. On a structural basis, it is believed that there are at least three distinct subclasses of PPO enzymes: HemY (M Hansson and L Hederstedt, "Cloning and characterization of the *Bacillus subtilis* hemEHY gene cluster, which encodes protoheme IX biosynthetic enzymes" *Journal of Bacteriology* 174(24):8081-8093 (1992)), HemG (A Sasarman, et al., "Mapping of a new hem gene in *Escherichia coli* K12" *Microbiology* 113:297-303 (1979)), and HemJ (TO Boynton, et al., "Discovery of a gene involved in a third bacterial protoporphyrinogen oxidase activity through comparative genomic analysis and functional complementation" *Applied and Environmental Microbiology* 77(14):4795-4801 (2011)). This invention provides novel recombinant iPPOs that are members of the HemY family. Despite over twenty years of research and the number of iPPOs identified to date, a transgenic crop plant comprising a recombinant iPPO has yet to be commercialized. A strong weed control platform depends, in part, on continued development of herbicide tolerance trait packages. Identifying and utilizing iPPOs to create transgenic crop traits therefore represents an advance to agriculture.

SUMMARY OF THE INVENTION

In one aspect, the invention provides a recombinant DNA molecule comprising a heterologous promoter operably linked to a nucleic acid sequence encoding a polypeptide that has at least 85% sequence identity to an amino acid sequence chosen from SEQ ID NOs:1-2 and SEQ ID NOs: 6-12, wherein the polypeptide has herbicide-insensitive protoporphyrinogen oxidase activity. In certain embodiments, the polypeptide has at least about 85% sequence identity, at least about 90% sequence identity, at least 95% sequence identity, at least 96% sequence identity, at least 97% sequence identity, at least 98% sequence identity, or at least 99% sequence identity to an amino acid sequence chosen from among SEQ ID NOs:1-2 and SEQ ID NOs:6-12 and has herbicide-insensitive protoporphyrinogen oxidase activity. In some embodiments there is provided a recombinant DNA molecule, wherein the nucleic acid sequence is selected from the group consisting of SEQ ID NOs:26-27, 31-32, 36-46, and 47-48. In particular embodiments the recombinant DNA molecule encodes a polypeptide comprising an amino acid sequence selected from the group consisting of SEQ ID NOs:1-2 and SEQ ID NOs:6-12. A recombinant polypeptide that comprises at least 85% sequence identity to the full length of an amino acid sequence chosen from among SEQ ID NOs:1-2 and SEQ ID NOs:6-12, wherein the polypeptide has herbicide-insensitive protoporphyrinogen oxidase activity is therefore provided by the invention.

In certain embodiments a heterologous promoter, for instance, a promoter functional in a plant cell, is operably linked to the nucleic acid sequence encoding a polypeptide that has at least 85% sequence identity to an amino acid sequence of the invention, for instance an amino acid sequence chosen from SEQ ID NOs:1-2 and SEQ ID NOs: 6-12, wherein the polypeptide has herbicide-insensitive protoporphyrinogen oxidase activity. Such a resulting DNA molecule may further comprise a targeting sequence that functions to localize the polypeptide within a cell.

In one aspect, the invention provides a DNA construct comprising a recombinant DNA molecule of the invention. In one embodiment, such a DNA construct comprises, in operable linkage to a nucleic acid sequence of the invention, a targeting sequence that functions to localize the polypeptide within a cell. The DNA construct may be present in the genome of a transgenic plant, seed, or cell. In certain embodiments, the polypeptide confers herbicide tolerance to the cell, plant, seed, or plant part.

Another aspect of the invention provides a transgenic plant, seed, cell, or plant part comprising a recombinant DNA molecule of the invention or a recombinant polypeptide of the invention. The transgenic plant, seed, cell, or plant part may thus comprise, i.e. display, tolerance to at least one PPO herbicide. In some embodiments, the transgenic plant, seed, cell, or plant part comprises an additional transgenic herbicide tolerance trait.

Another aspect of the invention provides a method for conferring herbicide tolerance to a plant, seed, cell, or plant part comprising: heterologously expressing a recombinant polypeptide of the invention in the plant, seed, cell, or plant part. In some embodiments of the method, the plant, seed, cell, or plant part comprises protoporphyrinogen oxidase activity conferred by the recombinant polypeptide. In some embodiments, the herbicide tolerance is to at least one PPO herbicide selected from the group consisting of acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil and S-3100.

Another aspect of the invention relates to a method of plant transformation, comprising the steps of: a) introducing a recombinant DNA molecule of the invention into a plant cell; and b) regenerating a transgenic plant therefrom that comprises the recombinant DNA molecule. The method may further comprise the step of selecting a plant that is tolerant to at least one PPO herbicide. The method may also further comprise a step of crossing the regenerated plant with itself or with a second plant and collecting seed from the cross.

Yet another aspect of the invention provides a method for controlling weeds in a plant growth area, comprising contacting a plant growth area comprising the transgenic plant or seed with at least one PPO herbicide, wherein the transgenic plant or seed is tolerant to the PPO herbicide and wherein weeds are controlled in the plant growth area.

Also provided is a method of identifying a nucleotide sequence encoding a protein having protoporphyrinogen oxidase activity, the method comprising: a) transforming an *E. coli* strain having a gene knockout for the native *E. coli* PPO enzyme with a bacterial expression vector comprising a recombinant DNA molecule encoding a candidate herbicide tolerance protein; and b) growing said transformed *E. coli* using a heme-free bacterial medium, wherein growth using said bacterial medium identifies a protein having protoporphyrinogen oxidase activity.

Further provided by the invention is a method of identifying a nucleotide sequence encoding a protein having herbicide-insensitive protoporphyrinogen oxidase activity, the method comprising: a) transforming an *E. coli* strain having a gene knockout for the native *E. coli* PPO enzyme with a bacterial expression vector comprising a recombinant DNA molecule encoding a recombinant protein; and b) growing said transformed *E. coli* using a bacterial medium containing at least one PPO herbicide, wherein growth of bacteria identifies a protein having herbicide-insensitive protoporphyrinogen oxidase activity.

Another aspect of the invention relates to a method of screening for a herbicide tolerance gene comprising: a) expressing a recombinant DNA molecule of the invention in a plant cell; and b) identifying a plant cell that displays tolerance to a PPO herbicide.

Further, the invention provides methods of screening for a herbicide tolerance gene comprising: a) expressing a recombinant DNA molecule of the invention in a bacterial cell lacking HemG, wherein the bacterial cell is grown in a heme-free medium in the presence of a PPO herbicide; and b) identifying a bacterial cell that displays tolerance to a PPO herbicide.

In another aspect, the invention provides a method of producing a plant tolerant to a PPO herbicide and at least one other herbicide comprising: a) obtaining a plant comprising a recombinant DNA molecule of the invention; b) crossing the transgenic plant with a second plant comprising tolerance to the at least one other herbicide, and c) selecting a progeny plant resulting from said crossing that comprises tolerance to a PPO herbicide and the at least one other herbicide is another aspect of the invention.

The invention also provides, in another aspect, a method for reducing the development of herbicide tolerant weeds comprising: a) cultivating in a crop growing environment a plant of the present invention that comprises tolerance to a PPO herbicide, for instance by comprising a DNA molecule of the present invention, and comprises tolerance to at least one other herbicide; and b) applying a PPO herbicide and at least one other herbicide to the crop growing environment, wherein the crop plant is tolerant to the PPO herbicide and the at least one other herbicide. In certain embodiments of the method, the PPO herbicide may be selected from the group consisting of acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil and S-3100. In some embodiments of the method, the at least one other herbicide is selected from the group consisting of: an ACCase inhibitor, an ALS inhibitor, an EPSPS inhibitor, a synthetic auxin, a photosynthesis inhibitor, a glutamine synthesis inhibitor, a HPPD inhibitor, a PPO inhibitor, and a long-chain fatty acid inhibitor. In particular embodiments, the ACCase inhibitor is an aryloxyphenoxy propionate or a cyclohexanedione; the ALS inhibitor is a sulfonylurea, imidazolinone, triazoloyrimidine, or a triazolinone; the EPSPS inhibitor is glyphosate; the synthetic auxin is a phenoxy herbicide, a benzoic acid, a carboxylic acid, or a semicarbazone; the photosynthesis inhibitor is a triazine, a triazinone, a nitrile, a benzothiadiazole, or a urea; the glutamine synthesis inhibitor is glufosinate; the HPPD inhibitor is an isoxazole, a pyrazolone, or a triketone; the PPO inhibitor is a diphenylether, a N-phenylphthalimide, an aryl triazinone, or a pyrimidinedione; or the long-chain fatty acid inhibitor is a chloroacetamide, an oxyacetamide, or a pyrazole.

BRIEF DESCRIPTION OF THE SEQUENCES

Figure 1:
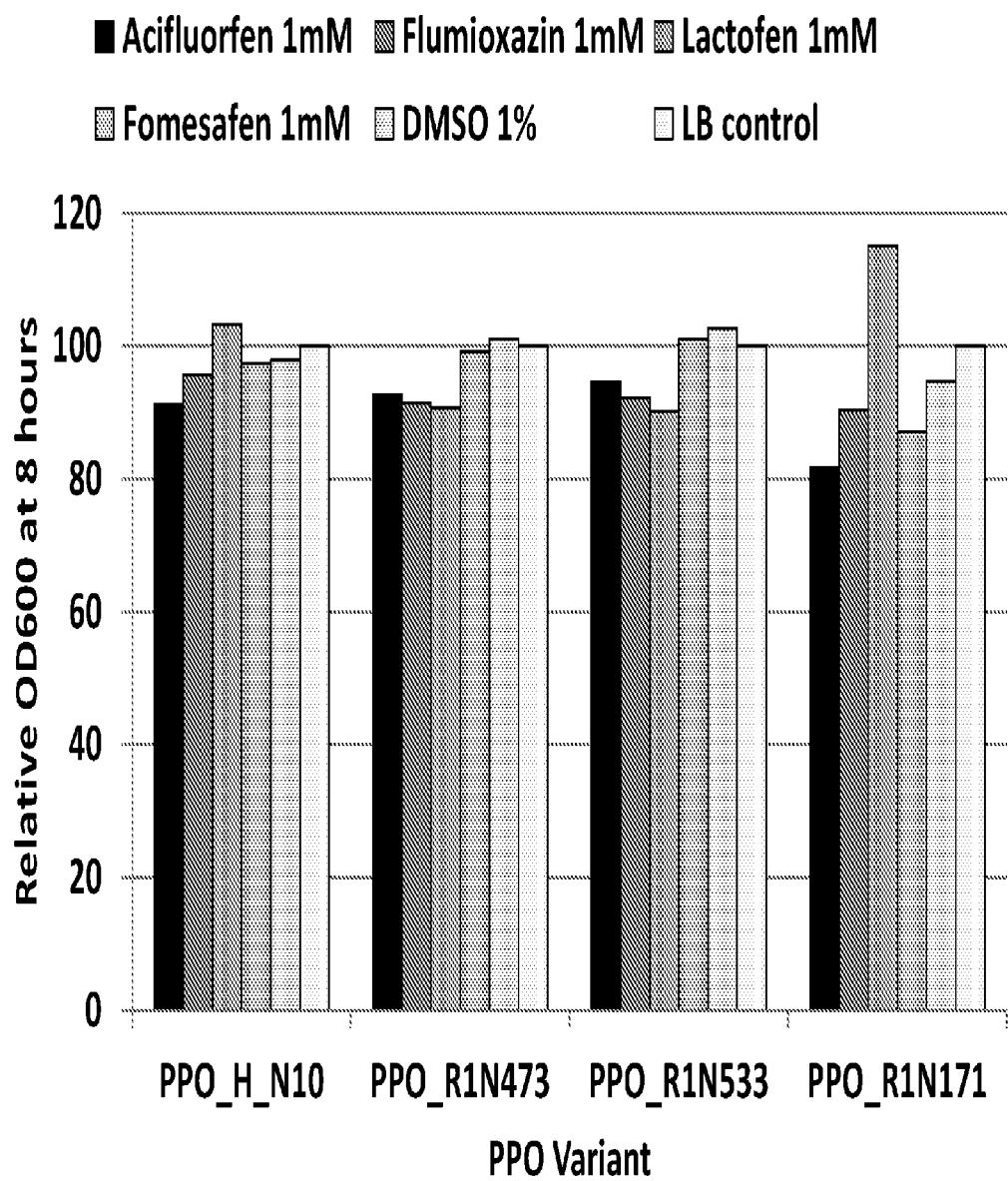
FIG. 1. Assay results from herbicide bacterial screening system with PPO herbicides. Assay of *E. coli* HemG (H_N10) (SEQ ID NO:76), HemY PPO R1N473 (SEQ ID NO:13), HemY PPO R1N533 (SEQ ID NO:14); or HemY PPO R1N171 (SEQ ID NO:15) in the presence of acifluorfen, flumioxazin, lactofen, or fomesafen PPO herbicides.

SEQ ID NO:1 is the amino acid sequence of R2N30.
SEQ ID NO:2 is the amino acid sequence of R2N40.

SEQ ID NO:3 is the amino acid sequence of R2N70.
SEQ ID NO:4 is the amino acid sequence of R2N90.
SEQ ID NO:5 is the amino acid sequence of R2N100.
SEQ ID NO:6 is the amino acid sequence of a variant of SEQ ID NO:1 (R2N30).
SEQ ID NOs:7-12 are the amino acid sequences of variants of SEQ ID NO:2 (R2N40).
SEQ ID NO:13 is the amino acid sequence of R1N473.
SEQ ID NO:14 is the amino acid sequence of R1N533.
SEQ ID NO:15 is the amino acid sequence of R1N171.
SEQ ID NO:16 is the amino acid sequence of R1N311.
SEQ ID NO:17 is the amino acid sequence of R1N333.
SEQ ID NO:18 is a truncated amino acid sequence of R1N473.
SEQ ID NO:19 is a truncated amino acid sequence of R1N533.
SEQ ID NO:20 is a truncated amino acid sequence of R1N171.
SEQ ID NO:21 is a truncated amino acid sequence of R1N333.
SEQ ID NO:22 is a truncated amino acid sequence of R1N473.
SEQ ID NO:23 is a truncated amino acid sequence of R1N533.
SEQ ID NO:24 is a truncated amino acid sequence of R1N171.
SEQ ID NO:25 is a truncated amino acid sequence of R1N333.
SEQ ID NOs:26-30 are the native bacterial nucleotide sequences encoding SEQ ID NOs:1 through SEQ ID NO:5, respectively.
SEQ ID NOs:31-35 are nucleotide sequences encoding SEQ ID NOs:1-5, respectively, codon optimized for dicot expression.
SEQ ID NOs:36-42 are nucleotide sequences encoding SEQ ID NOs:6-12, respectively, codon optimized for dicot expression.
SEQ ID NOs:43-46 are nucleotide sequences encoding SEQ ID NO:9, codon optimized for dicot expression.
SEQ ID NOs:47-51 are nucleotide sequences encoding SEQ ID NOs:1-5, respectively, codon optimized for monocot expression.
SEQ ID NOs:52-56 are the native bacterial nucleotide sequences encoding SEQ ID NOs:13-17.
SEQ ID NOs:57-62 are the nucleotide sequences encoding the amino acid sequences represented by SEQ ID NOs:13-17, codon optimized for dicot expression.
SEQ ID NOs:63-67 are the nucleotide sequences encoding the amino acid sequences represented by SEQ ID NOs:13-17, codon optimized for monocot expression.
SEQ ID NOs:68-75 are the nucleotide sequences encoding the amino acid sequences represented by SEQ ID NOs:18-25, respectively, codon optimized for dicot expression.
SEQ ID NO:76 is the amino acid sequence of E. coli PPO enzyme HemG (protoporphyrinogen IX dehydrogenase; GenBank Accession No. WP_021498199).
SEQ ID NOs:77-79 are the nucleotide sequences encoding the amino acid sequence represented by SEQ ID NO:76.
SEQ ID NO:80 is the amino acid sequence of the wild-type protoporphyrinogen oxidase from Amaranthus tuberculatus (WH).
SEQ ID NO:81 is the nucleotide sequence encoding the amino acid sequence represented by SEQ ID NO:80, codon optimized for bacterial E. coli expression.

DETAILED DESCRIPTION

The following descriptions and definitions are provided to better define the invention and to guide those of ordinary skill in the art in the practice of the invention. Unless otherwise noted, terms are to be understood according to conventional usage by those of ordinary skill in the relevant art.

The invention provides novel, recombinant DNA molecules and proteins that encode herbicide-insensitive protoporphyrinogen oxidases (iPPOs). For instance, the invention provides in one embodiment vectors and expression cassettes encoding microbially derived iPPOs for expression in cells and plants. Methods for producing cells and plants tolerant to PPO herbicides are also provided. The invention further provides methods and compositions for using protein engineering and bioinformatic tools to obtain and improve iPPOs.

In specific aspects, the invention provides recombinant DNA molecules and proteins. As used herein, the term "recombinant" refers to a non-naturally occurring DNA, protein, cell, seed, or organism that is the result of genetic engineering and as such would not normally be found in nature. A "recombinant DNA molecule" is a DNA molecule comprising a DNA sequence that does not naturally occur in nature and as such is the result of human intervention, such as a DNA molecule comprised of at least two DNA molecules heterologous to each other. An example of a recombinant DNA molecule is a DNA molecule provided herein encoding herbicide-insensitive protoporphyrinogen oxidase operably linked to a heterologous regulatory or other element, such as a heterologous promoter. A "recombinant protein" is a protein comprising an amino acid sequence that does not naturally occur and as such is the result of human intervention, such as an engineered protein or a chimeric protein. A recombinant cell, seed, or organism is a cell, seed, or organism comprising transgenic DNA, for example a transgenic cell, seed, plant, or plant part comprising a recombinant DNA molecule and therefore produced as a result of plant transformation.

As used herein, the term "genetic engineering" refers to the creation of a non-natural DNA, protein, or organism that would not normally be found in nature and therefore entails applying human intervention. Genetic engineering can be used to produce an engineered DNA, protein, or organism that was conceived of and created in the laboratory using one or more of the techniques of biotechnology such as molecular biology, protein biochemistry, bacterial transformation, and plant transformation. For example, genetic engineering can be used to create a chimeric gene comprising at least two DNA molecules heterologous to each other using one or more of the techniques of molecular biology, such as gene cloning, DNA ligation, and DNA synthesis. A chimeric gene may consist of two or more heterologous DNA molecules that are operably linked, such as a protein-coding sequence operably linked to a gene expression element such as a transit peptide-coding sequence or a heterologous promoter. Genetic engineering can be used to create an engineered protein whose amino acid sequence was created using one or more of the techniques of protein engineering, such as protein design using site-directed mutagenesis and directed evolution using random mutagenesis and DNA shuffling. An engineered protein may have one or more deletions, insertions, or substitutions relative to the coding sequence of the wild-type protein and each deletion, insertion, or substitution may consist of one or more amino acids. In another embodiment, an engineered protein may consist of two heterologous peptides that are operably linked, such as an enzyme operably linked to a transit peptide.

As used herein, "herbicide-insensitive" or "herbicide-insensitive protoporphyrinogen oxidase activity" means the ability of a protoporphyrinogen oxidase (PPO, EC 1.3.3.4) to maintain at least some of its protoporphyrinogen oxidase activity in the presence of one or more PPO herbicide(s). The term "protoporphyrinogen oxidase activity" means the ability to catalyze the six-electron oxidation (removal of electrons) of protoporphyrinogen IX to form protoporphyrin IX, that is, to catalyze the dehydrogenation of protoporphyrinogen to form protoporphyrin. Enzymatic activity of a protoporphyrinogen oxidase can be measured by any means known in the art, for example, by an enzymatic assay in which the production of the product of protoporphyrinogen oxidase or the consumption of the substrate of protoporphyrinogen oxidase in the presence of one or more PPO herbicide(s) is measured via fluorescence, high performance liquid chromatography (HPLC), or mass spectrometry (MS). Another example of an assay for measuring enzymatic activity of a protoporphyrinogen oxidase is a bacterial assay, such as the assays described herein, whereby a recombinant protoporphyrinogen oxidase is expressed in a bacterial cell otherwise lacking PPO activity and the ability of the recombinant protoporphyrinogen oxidase to complement this knockout phenotype is measured. Herbicide-insensitivity may be complete or partial insensitivity to a particular herbicide, and may be expressed as a percent (%) tolerance or insensitivity to a particular PPO herbicide. As used herein, an "herbicide-insensitive protoporphyrinogen oxidase" or "iPPO" exhibits herbicide-insensitivity in the presence of one or more PPO herbicide(s).

As used herein, a "hemG knockout strain" means an organism or cell of an organism, such as $E.$ $coli$, that lacks HemG activity to the extent that it is unable to grow on heme-free growth medium, or such that its growth is detectably impaired in the absence of heme relative to an otherwise isogenic strain comprising a functional HemG. A hemG knockout strain of, for instance, $E.$ $coli$ may be prepared in view of knowledge in the art, for instance in view of the $E.$ $coli$ hemG sequence (Ecogene Accession No. EG11485; Sasarman et al., "Nucleotide sequence of the hemG gene involved in the protoporphyrinogen oxidase activity of $E.$ $coli$ K12" Can J Microbiol 39:1155-1161, 1993).

As used herein, the term "transgene" refers to a DNA molecule artificially incorporated into an organism's genome because of human intervention, such as a plant transformation method. As used herein, the term "transgenic" means comprising a transgene, for example a "transgenic plant" refers to a plant comprising a transgene in its genome and a "transgenic trait" refers to a characteristic or phenotype conveyed or conferred by the presence of a transgene incorporated into the plant genome. Because of such genomic alteration, the transgenic plant is something distinctly different from the related wild-type plant and the transgenic trait is a trait not naturally found in the wild-type plant. Transgenic plants of the invention comprise the recombinant DNA molecules and engineered proteins provided by the invention.

As used herein, the term "heterologous" refers to the relationship between two or more items derived from different sources and thus not normally associated in nature. For example, a protein-coding recombinant DNA molecule is heterologous with respect to an operably linked promoter if such a combination is not normally found in nature. In another example, a protein-coding DNA molecule or a polypeptide may be heterologously expressed in a plant, seed, cell, or plant part if such protein-coding DNA molecule or polypeptide is not normally expressed in such a plant, seed, cell, or plant part in nature. A particular recombinant DNA molecule may be heterologous with respect to a cell, seed, or organism into which it is inserted when it would not naturally occur in that particular cell, seed, or organism. A particular polypeptide may be heterologous with respect to a cell, seed, or organism in which it is expressed when it would not naturally occur in that particular cell, seed, or organism.

As used herein, the term "isolated" refers to at least partially separating a molecule from other molecules typically associated with it in its natural state. In one embodiment, the term "isolated" refers to a DNA molecule that is separated from the nucleic acids that normally flank the DNA molecule in its natural state. For example, a DNA molecule encoding a protein that is naturally present in a bacterium would be an isolated DNA molecule if it was not within the DNA of the bacterium from which the DNA molecule encoding the protein is naturally found. Thus, a DNA molecule fused to or operably linked to one or more other DNA molecule(s) with which it would not be associated in nature, for example as the result of recombinant DNA or plant transformation techniques, is considered isolated herein. Such molecules are considered isolated even when integrated into the chromosome of a host cell or present in a nucleic acid solution with other DNA molecules.

As used herein, the term "protein-coding DNA molecule" refers to a DNA molecule comprising a nucleotide sequence that encodes a protein. A "protein-coding sequence" means a nucleic acid sequence that encodes a protein. A "sequence" means a sequential arrangement of nucleotides or amino acids. The boundaries of a protein-coding sequence may be determined by a translation start codon at the 5'-terminus and a translation stop codon at the 3'-terminus. A protein-coding molecule may comprise a nucleic acid sequence encoding an amino acid sequence. As used herein, "transgene expression", "expressing a transgene", "protein expression", and "expressing a protein" mean the production of a protein through the process of transcribing a DNA molecule into messenger RNA (mRNA) and translating the mRNA into polypeptide chains, which are ultimately folded into proteins. A protein-coding DNA molecule may be operably linked to a heterologous promoter in a DNA construct for use in expressing the protein in a cell transformed with the recombinant DNA molecule. As used herein, "operably linked" means two or more DNA molecules or two or more polypeptides linked in manner so that one may affect the function of the other. Operably-linked DNA molecules or operably-linked polypeptides may be part of a single contiguous molecule and may or may not be adjacent. For example, a promoter is operably linked with a protein-coding DNA molecule in a DNA construct where the two DNA molecules are so arranged that the promoter may affect the expression of the transgene.

As used herein, a "DNA construct" is a recombinant DNA molecule comprising two or more heterologous DNA sequences. DNA constructs are useful for transgene expression and may be comprised in vectors and plasmids. DNA constructs may be used in vectors for the purpose of transformation, that is the introduction of heterologous DNA into a host cell, to produce transgenic plants and cells, and as such may also be contained in the plastid DNA or genomic DNA of a transgenic plant, seed, cell, or plant part. As used herein, a "vector" means any recombinant DNA molecule that may be used for the purpose of bacterial or plant transformation. Recombinant DNA molecules as set forth in the sequence listing, can, for example, be inserted into a vector as part of a construct having the recombinant DNA molecule operably linked to a gene expression element that functions in a plant to affect expression of the engineered protein encoded by the recombinant DNA molecule. General methods useful for manipulating DNA molecules for making and using recombinant DNA constructs and plant transformation vectors are well known in the art and described in detail in, for example, handbooks and laboratory manuals including Michael R. Green and Joseph Sambrook, "Molecular Cloning: A Laboratory Manual" (Fourth Edition) ISBN:978-1-936113-42-2, Cold Spring Harbor Laboratory Press, NY (2012). The components for a DNA construct, or a vector comprising a DNA construct, include one or more gene expression elements operably linked to a transcribable nucleic acid sequence, such as the following: a promoter for the expression of an operably linked DNA, an operably linked protein-coding DNA molecule, and an operably linked 3' untranslated region (UTR). Gene expression elements useful in practicing the present invention include, but are not limited to, one or more of the following type of elements: promoter, 5' UTR, enhancer, leader, cis-acting element, intron, targeting sequence, 3' UTR, and one or more selectable marker transgenes.

The DNA constructs of the invention may include a promoter operably linked to a protein-coding DNA molecule provided by the invention, whereby the promoter drives expression of the recombinant protein molecule. Promoters useful in practicing the present invention include those that function in a cell for expression of an operably linked polynucleotide, such as a bacterial or plant promoter. Plant promoters are varied and well known in the art and include, for instance, those that are inducible, viral, synthetic, constitutive, temporally regulated, spatially regulated, and/or spatio-temporally regulated.

In one embodiment of the invention, a DNA construct provided herein includes a nucleic acid sequence encoding a targeting sequence that is operably linked to a heterologous nucleic acid sequence encoding a polypeptide molecule that has herbicide-insensitive protoporphyrinogen oxidase activity, whereby the targeting sequence facilitates localizing the polypeptide molecule within the cell. Targeting sequences are known in the art as signal sequences, targeting peptides, localization sequences, and transit peptides. An example of a targeting sequence is a chloroplast transit peptide (CTP), a mitochondrial targeting sequence (MTS), or a dual chloroplast and mitochondrial targeting peptide. By facilitating protein localization within the cell, the targeting sequence may increase the accumulation of recombinant protein, protect the protein from proteolytic degradation, and/or enhance the level of herbicide tolerance, and thereby reduce levels of injury in the transgenic cell, seed, or organism after herbicide application.

CTPs and other targeting molecules that may be used in connection with the present invention are known in the art and include, but are not limited to, the *Arabidopsis thaliana* EPSPS CTP (Klee et al., *Mol Gen Genet.* 210:437-442, 1987), the *Petunia hybrida* EPSPS CTP (della-Cioppa et al., *PNAS* 83:6873-6877, 1986), the maize cab-m7 signal sequence (Becker et al., *Plant Mol Biol.* 20:49-60, 1992; PCT WO 97/41228), a mitochondrial pre-sequence (e.g. Silva Filho et al., *Plant Mol Biol* 30:769-780, 1996), and the pea glutathione reductase signal sequence (Creissen et al., *Plant J.* 8:167-175, 1995; PCT WO 97/41228).

Recombinant DNA molecules of the present invention may be synthesized and modified by methods known in the art, either completely or in part, where it is desirable to provide sequences useful for DNA manipulation (such as restriction enzyme recognition sites or recombination-based cloning sites), plant-preferred sequences (such as plant-codon usage or Kozak consensus sequences), or sequences useful for DNA construct design (such as spacer or linker sequences). The present invention includes recombinant DNA molecules and engineered proteins having at least 70% sequence identity, at least 80% sequence identity, at least 85% sequence identity, at least 90% sequence identity, at least 95% sequence identity, at least 96% sequence identity, at least 97% sequence identity, at least 98% sequence identity, and at least 99% sequence identity to any of the recombinant DNA molecule or amino acid sequences provided herein, and having herbicide-insensitive protoporphyrinogen oxidase activity. As used herein, the term "percent sequence identity" or "% sequence identity" refers to the percentage of identical nucleotides or amino acids in a linear polynucleotide or amino acid sequence of a reference ("query") sequence (or its complementary strand) as compared to a test ("subject") sequence (or its complementary strand) when the two sequences are optimally aligned (with appropriate nucleotide or amino acid insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and by computerized implementations of these algorithms such as GAP, BESTFIT, FASTA, and TFASTA available as part of the Sequence Analysis software package of the GCG® Wisconsin Package® (Accelrys Inc., San Diego, Calif.), MEGAlign (DNAStar Inc., 1228 S. Park St., Madison, Wis. 53715), and MUSCLE (version 3.6) (RC Edgar, "MUSCLE: multiple sequence alignment with high accuracy and high throughput" Nucleic Acids Research 32(5):1792-7 (2004)) for instance with default parameters. An "identity fraction" for aligned segments of a test sequence and a reference sequence is the number of identical components that are shared by the two aligned sequences divided by the total number of components in the portion of the reference sequence segment being aligned, that is, the entire reference sequence or a smaller defined part of the reference sequence. Percent sequence identity is represented as the identity fraction multiplied by 100. The comparison of one or more sequences may be to a full-length sequence or a portion thereof, or to a longer sequence. Engineered proteins may be produced by changing (that is, modifying) a wild-type protein to produce a new protein with modified characteristic(s) e.g. a particular cellular localization pattern, such as targeted to the chloroplast or mitochondria, or a novel combination of useful protein characteristics, such as altered $V_{max}$, $K_m$, $K_i$, $IC_{50}$, substrate specificity, inhibitor/herbicide specificity, substrate selectivity, the ability to interact with other components in the cell such as partner proteins or membranes, and protein stability, among others. Modifications may be made at specific amino acid positions in a protein and may be a substitution of the amino acid found at that position in nature (that is, in the wild-type protein) with a different amino acid. Engineered proteins provided by the invention thus provide a new protein with one or more altered protein characteristics relative to a similar protein found in nature. In one embodiment of the invention, an engineered protein has altered protein characteristics, such as those that result in decreased sensitivity to one or more herbicides as compared to a similar wild-type protein or improved ability to confer herbicide tolerance on a transgenic plant expressing the engineered protein to one or more herbicides. In one embodiment, the invention provides an engineered protein, and the recombinant DNA molecule encoding it, comprising at least one amino acid substitution selected from Table 1 and having at least about 70% sequence identity, about 80% sequence identity, about 85% sequence identity, about 90% sequence identity, about 95% sequence identity, about 96% sequence identity, about 97% sequence identity, about 98% sequence identity, and about 99% sequence identity to any of the engineered amino acid sequences provided herein, including but not limited to SEQ ID NOs: 1-2 and 6-12. Amino acid mutations may be made as a single amino acid substitution in the protein or in combination with one or more other mutation(s), such as one or more other amino acid substitution(s), deletions, or additions. Mutations may be made by any method known to those of skill in the art.

TABLE 1

Amino Acid Substitutions.

| Residue | Conservative Substitutions | Residue | Conservative Substitutions |
|---|---|---|---|
| Ala | Ser | Leu | Ile; Val |
| Arg | Lys | Lys | Arg; Gln |
| Asn | Gln; His | Met | Leu; Ile |
| Asp | Glu | Phe | Met; Leu; Tyr |
| Gln | Asn | Ser | Thr; Gly |
| Cys | Ser | Thr | Ser; Val |
| Glu | Asp | Trp | Tyr |
| Gly | Pro | Tyr | Trp; Phe |
| His | Asn; Gln | Val | Ile; Leu |
| Ile | Leu; Val | | |

As used herein, "wild-type" means a naturally occurring similar, but not identical, version. A "wild-type DNA molecule" or "wild-type protein" is a naturally occurring version of the DNA molecule or protein, that is, a version of the DNA molecule or protein pre-existing in nature. An example of a wild-type protein useful for comparison with the engineered proteins provided by the invention is the protoporphyrinogen oxidase from *Arabidopsis thaliana*. A "wild-type plant" is a non-transgenic plant of the same type as the transgenic plant, and as such is genetically distinct from the transgenic plant comprising the herbicide tolerance trait. Examples of a wild-type plant useful for comparison with transgenic maize plants are non-transgenic LH244 maize (ATCC deposit number PTA-1173) and 01DKD2 inbred maize (1294213) (ATCC deposit number PTA-7859). For transgenic soybean plants an exemplary comparative line would be non-transgenic A3555 soy (ATCC deposit number PTA-10207), and for transgenic cotton plants an exemplary comparative line would be non-transgenic Coker 130 (Plant Variety Protection Number 8900252).

Transgenic Plants & Herbicides

One aspect of the invention includes transgenic plant cells, transgenic plant tissues, transgenic plants, and transgenic seeds that comprise the recombinant DNA molecules and engineered proteins provided by the invention. These cells, tissues, plants, and seeds comprising the recombinant DNA molecules and engineered proteins exhibit herbicide tolerance to one or more PPO herbicide(s), and, optionally, tolerance to one or more additional herbicide(s).

Suitable methods for transformation of host plant cells for use with the current invention include virtually any method by which DNA can be introduced into a cell (for example, where a recombinant DNA construct is stably integrated into a plant chromosome) and are well known in the art. An exemplary and widely utilized method for introducing a recombinant DNA construct into plants is the *Agrobacterium* transformation system, which is well known to those of skill in the art. Another exemplary method for introducing a recombinant DNA construct into plants is insertion of a recombinant DNA construct into a plant genome at a predetermined site by methods of site-directed integration. Site-directed integration may be accomplished by any method known in the art, for example, by use of zinc-finger nucleases, engineered or native meganucleases, TALE-endonucleases, or an RNA-guided endonuclease (for example a CRISPR/Cas9 system). Transgenic plants can be regenerated from a transformed plant cell by the methods of plant cell culture. A transgenic plant homozygous with respect to a transgene (that is, two allelic copies of the transgene) can be obtained by self-pollinating (selfing) a transgenic plant that contains a single transgene allele with itself, for example an R0 plant, to produce R1 seed. One fourth of the R1 seed produced will be homozygous with respect to the transgene. Plants grown from germinating R1 seed can be tested for zygosity, using a SNP assay, DNA sequencing, or a thermal amplification assay that allows for the distinction between heterozygotes and homozygotes, referred to as a zygosity assay.

As used herein, a "PPO inhibitor herbicide" or "PPO herbicide" is a chemical that targets and inhibits the enzymatic activity of a protoporphyrinogen oxidase (PPO), which catalyzes the dehydrogenation of protoporphyrinogen IX to form protoporphyrin IX, which is the precursor to heme and chlorophyll. Inhibition of protoporphyrinogen oxidase causes formation of reactive oxygen species, resulting in cell membrane disruption and ultimately the death of susceptible cells. PPO herbicides are well-known in the art and commercially available. Examples of PPO herbicides include, but are not limited to, diphenylethers (such as acifluorfen, its salts and esters, aclonifen, bifenox, its salts and esters, ethoxyfen, its salts and esters, fluoronitrofen, furyloxyfen, halosafen, chlomethoxyfen, fluoroglycofen, its salts and esters, lactofen, its salts and esters, oxyfluorfen, and fomesafen, its salts and esters); thiadiazoles (such as fluthiacet-methyl and thidiazimin); pyrimidinediones or phenyluracils (such as benzfendizone, butafenacil, ethyl [3-2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS Registry Number 353292-31-6 and referred to herein as S-3100), flupropacil, saflufenacil, and tiafenacil); phenylpyrazoles (such as fluazolate, pyraflufen and pyraflufen-ethyl); oxadiazoles (such as oxadiargyl and oxadiazon); triazolinones (such as azafenidin, bencarbazone, carfentrazone, its salts and esters, and sulfentrazone); oxazolidinediones (such as pentoxazone); N-phenylphthalimides (such as cinidon-ethyl, flumiclorac, flumiclorac-pentyl, and flumioxazin); benzoxazinone derivatives (such as 1,5-dimethyl-6-thioxo-3-(2,2,7-trifluoro-3,4-dihydro-3-oxo-4-prop-2-ynyl-2H-1,4-benzoxazin-6-yl)-1,3,5-triazinane-2,4-dione); flufenpyr and flufenpyr-ethyl; pyraclonil; and profluazol. Protoporphyrinogen oxidases and cells, seeds, plants, and plant parts provided by the invention exhibit herbicide tolerance to one or more PPO herbicide(s).

Herbicides may be applied to a plant growth area comprising the plants and seeds provided by the invention as a method for controlling weeds. Plants and seeds provided by the invention comprise an herbicide tolerance trait and as such are tolerant to the application of one or more PPO herbicides. The herbicide application may be the recommended commercial rate (1×) or any fraction or multiple thereof, such as twice the recommended commercial rate (2×). Herbicide rates may be expressed as acid equivalent per pound per acre (lb ae/acre) or acid equivalent per gram per hectare (g ae/ha) or as pounds active ingredient per acre (lb ai/acre) or grams active ingredient per hectare (g ai/ha), depending on the herbicide and the formulation. The herbicide application comprises at least one PPO herbicide. The plant growth area may or may not comprise weed plants at the time of herbicide application. A herbicidally effective dose of PPO herbicide(s) for use in an area for controlling weeds may consist of a range from about 0.1× to about 30× label rate(s) over a growing season. The 1× label rate for some exemplary PPO herbicides is provided in Table 2. One (1) acre is equivalent to 2.47105 hectares and one (1) pound is equivalent to 453.592 grams. Herbicide rates can be converted between English and metric as: (lb ai/ac) multiplied by 1.12=(kg ai/ha) and (kg ai/ha) multiplied by 0.89= (lb ai/ac).

TABLE 2

Exemplary PPO Herbicides

| PPO Herbicide | Chemical Family | 1X Rate |
| --- | --- | --- |
| aciflurofen | Diphenylethers | 420 g ai/ha |
| fomesafen | Diphenylethers | 420 g ai/ha |
| lactofen | Diphenylethers | 7-220 g ai/ha |
| fluoroglycofen-ethyl | Diphenylethers | 15-40 g ai/ha |
| oxyfluorfen | Diphenylethers | 0.28-2.24 kg ai/ha |
| flumioxazin | N-phenylphthalimide | 70 g ai/ha |
| azafenidin | Triazolinone | 240 g ai/ha |
| carfentrazone-ethyl | Triazolinone | 4-36 g ai/ha |
| sulfentrazone | Triazolinone | 0.1-0.42 kg ai/ha |
| fluthiacet-methyl | Thiadiazole | 3-15 g ai/ha |
| oxadiargyl | Oxadiazole | 50-150 g ai/ha |
| oxadiazon | Oxadiazole | 2.24-4.48 kg ai/ha |
| pyraflufen-ethyl | Phenylpyrazole | 6-12 g ai/ha |
| saflufenacil | Pyrimidine dione | 25-50 g/ha |
| S-3100 | Pyrimidine dione | 5-80 g/ha |

Herbicide applications may be sequentially or tank mixed with one, two, or a combination of several PPO herbicides or any other compatible herbicide. Multiple applications of one herbicide or of two or more herbicides, in combination or alone, may be used over a growing season to areas comprising transgenic plants of the invention for the control of a broad spectrum of dicot weeds, monocot weeds, or both, for example, two applications (such as a pre-planting application and a post-emergence application or a pre-emergence application and a post-emergence application) or three applications (such as a pre-planting application, a pre-emergence application, and a post-emergence application or a pre-emergence application and two post-emergence applications).

As used herein, "tolerance" or "herbicide tolerance" means a plant, seed, or cell's ability to resist the toxic effects of an herbicide when applied. Herbicide tolerant crops can continue to grow and are unaffected or minimally affected by the presence of the applied chemical. As used herein, an "herbicide tolerance trait" is a transgenic trait imparting improved herbicide tolerance to a plant as compared to the wild-type plant. Contemplated plants which might be produced with an herbicide tolerance trait of the present invention could include, for instance, any plant including crop plants such as soybean (e.g. *Glycine max*), corn (maize), cotton (*Gossypium* sp.), and canola, among others.

The transgenic plants, progeny, seeds, plant cells, and plant parts of the invention may also contain one or more additional transgenic traits. Additional transgenic traits may be introduced by crossing a plant containing a transgene comprising the recombinant DNA molecules provided by the invention with another plant containing one or more additional transgenic trait(s). As used herein, "crossing" means breeding two individual plants to produce a progeny plant. Two transgenic plants may thus be crossed to produce progeny that contain the transgenic traits from each parent. As used herein "progeny" means the offspring of any generation of a parent plant, and transgenic progeny comprise a DNA construct provided by the invention and inherited from at least one parent plant. Alternatively, additional transgenic trait(s) may be introduced by co-transforming a DNA construct for that additional transgenic trait(s) with a DNA construct comprising the recombinant DNA molecules provided by the invention (for example, with all the DNA constructs present as part of the same vector used for plant transformation) or by inserting the additional trait(s) into a transgenic plant comprising a DNA construct provided by the invention or vice versa (for example, by using any of the methods of plant transformation or gene editing on a transgenic plant or plant cell). Such additional transgenic traits include, but are not limited to, increased insect resistance, increased water use efficiency, increased yield performance, increased drought resistance, increased seed quality, improved nutritional quality, hybrid seed production, and herbicide tolerance, in which the trait is measured with respect to a wild-type plant. Exemplary additional herbicide tolerance traits may include transgenic or non-transgenic tolerance to one or more herbicides such as ACCase inhibitors (for example aryloxyphenoxy propionates and cyclohexanediones), ALS inhibitors (for example sulfonylureas, imidazolinones, triazoloyrimidines, and triazolinones) EPSPS inhibitors (for example glyphosate), synthetic auxins (for example phenoxys, benzoic acids, carboxylic acids, semicarbazones), photosynthesis inhibitors (for example triazines, triazinones, nitriles, benzothiadiazoles, and ureas), glutamine synthesis inhibitors (for example glufosinate), HPPD inhibitors (for example isoxazoles, pyrazolones, and triketones), PPO inhibitors (for example diphenylethers, N-phenylphthalimide, aryl triazinones, and pyrimidinediones), and long-chain fatty acid inhibitors (for example chloroacetamindes, oxyacetamides, and pyrazoles), among others. Exemplary insect resistance traits may include resistance to one or more insect members within one or more of the orders of Lepidoptera, Coleoptera, Hemiptera, and Homoptera, among others. Such additional transgenic traits are known to one of skill in the art; for example, a list of such traits is provided by the United States Department of Agriculture's (USDA) Animal and Plant Health Inspection Service (APHIS).

A cell transformed with a polynucleotide of the present invention, such as an expression construct, may be selected for the presence of the polynucleotide or its encoded enzymatic activity before or after regenerating such a cell into a transgenic plant. Transgenic plants comprising such a polynucleotide may thus be selected for instance by identifying a transgenic plant that comprises the polynucleotide or the encoded enzymatic activity, and/or displays an altered trait relative to an otherwise isogenic control plant. Such a trait may be, for example, tolerance to a PPO herbicide.

Transgenic plants and progeny that contain a transgenic trait provided by the invention may be used with any breeding methods that are known in the art. In plant lines comprising two or more transgenic traits, the transgenic traits may be independently segregating, linked, or a combination of both in plant lines comprising three or more transgenic traits. Back-crossing to a parental plant and out-crossing with a non-transgenic plant are also contemplated, as is vegetative propagation. Descriptions of breeding methods that are used for different traits and crops are well known to those of skill in the art. To confirm the presence of the transgene(s) in a particular plant or seed, a variety of assays may be performed. Such assays include, for example, molecular biology assays, such as Southern and northern blotting, PCR, and DNA sequencing; biochemical assays, such as detecting the presence of a protein product, for example, by immunological means (ELISAs and western blots) or by enzymatic function; plant part assays, such as leaf or root assays; and also, by analyzing the phenotype of the whole plant.

Introgression of a transgenic trait into a plant genotype is achieved as the result of the process of backcross conversion. A plant genotype into which a transgenic trait has been introgressed may be referred to as a backcross converted genotype, line, inbred, or hybrid. Similarly a plant genotype lacking the desired transgenic trait may be referred to as an unconverted genotype, line, inbred, or hybrid.

Having described the invention in detail, it will be apparent that modifications, variations, and equivalent embodiments are possible without departing the scope of the invention defined in the appended claims. Furthermore, it should be appreciated that the examples in the present disclosure are provided as non-limiting examples.

EXAMPLES

The following examples are included to demonstrate embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit, and scope of the invention. More specifically, it will be apparent that certain agents which are both chemically and physiologically related may be substituted for the agents described herein with the same or similar result achieved. All such similar substitutes and modifications apparent to those skilled in the art are deemed to be within the spirit, scope, and concept of the invention as defined by the appended claims.

Example 1: Microbial Protoporphyrinogen Oxidase Discovery

Novel protoporphyrinogen oxidases were identified from microbial sequence databases using bioinformatic methods and a novel protoporphyrinogen oxidase bacterial screening system. Three sequences representing a diverse range of HemY microbial protoporphyrinogen oxidases and the sequence for the PPO herbicide sensitive HemY protoporphyrinogen oxidase from *Arabidopsis thaliana* were used to identify new putative protoporphyrinogen oxidase sequences from microbial sequence databases. The use of these four diverse sequences with bioinformatic tools permitted skewing of search results toward sequences that are more similar to microbial protoporphyrinogen oxidases than plant protoporphyrinogen oxidases in order to increase the likelihood of identifying PPO herbicide tolerant protoporphyrinogen oxidases.

Ninety-nine putative protoporphyrinogen oxidases of the HemY PPO family were identified using this method. The sequences encoding these putative HemY PPO enzymes were compared using phylogenetic tree mapping. Forty-four putative HemY PPO enzymes were selected for further analysis due to their representation of individual unique clustered members on the phylogenetic tree. The coding sequences for the forty-four selected putative HemY PPO enzymes were cloned into bacterial expression vectors for analysis in a *E. coli* hemG knockout screen described below.

A protoporphyrinogen oxidase bacterial screening system was created to test recombinant proteins for protoporphyrinogen oxidase activity. This screening system used a functional rescue assay in an *E. coli* strain that contained a gene knockout for the *E. coli* PPO enzyme (HemG; SEQ ID NO: 76). The hemG knockout *E. coli* strain showed minimal growth on classical bacterial media (e.g., LB media), but growth rates recovered when the bacterial media was supplemented with free heme or when a recombinant protoporphyrinogen oxidase was expressed in the *E. coli*. The hemG knockout *E. coli* strain could thus be used with recombinant protein expression to quickly and easily assay proteins for protoporphyrinogen oxidase activity.

The hemG knockout *E. coli* strain was transformed with the bacterial expression vectors containing the putative protoporphyrinogen oxidases and plated on LB media. Recombinant proteins were expressed in *E. coli* and growth rates were measured. Growth of the transformed hemG knockout *E. coli* strain on LB media indicated an amino acid sequence that confirmed as a functioning protoporphyrinogen oxidase. Using this assay, a large number of novel or engineered proteins can be screened to confirm and measure protoporphyrinogen oxidase activity. Ten of the forty-four putative novel PPO enzymes rescued the hemG knockout *E. coli* strain, confirming their activity as protoporphyrinogen oxidases, and were selected for further characterization. Table 3 provides the SEQ ID NOs corresponding to the ten selected HemY PPO variants, the *E. coli* HemG, and the *A. tuberculatus* PPO.

TABLE 3

SEQ ID NOs corresponding to HemY PPO variants

| PPO | Protein | Bacterial DNA | Dicot codon optimized | Monocot codon optimized |
|---|---|---|---|---|
| R2N30 | 1, 6 | 26 | 31, 36 | 47 |
| R2N40 | 2, 7, 8, 9, 10, 11, 12 | 27 | 32, 37, 38, 39, 40, 41, 42, 43, 44, 45, 46 | 48 |
| R2N70 | 3 | 28 | 33 | 49 |
| R2N90 | 4 | 29 | 34 | 50 |
| R2N100 | 5 | 30 | 35 | 51 |
| R1N473 | 13, 18, 22 | 52 | 57, 68, 72 | 63 |
| R1N533 | 14, 19, 23 | 53 | 58, 69, 73 | 64 |
| R1N171 | 15, 20, 24 | 54 | 59, 70, 74 | 65 |
| R1N311 | 16 | 55 | 60 | 66 |
| R1N333 | 17, 21, 25 | 56 | 61, 62, 71, 75 | 67 |
| *E. coli* HemG | 76 | 77 | 78 | 79 |
| *A. tuberculatus* | 80 | 81 | n/a | n/a |

Example 2: Protoporphyrinogen Oxidase Inhibitor Insensitivity

Novel protoporphyrinogen oxidases that are tolerant to PPO herbicides were identified using an herbicide bacterial screening system. This screening system used a growth assay of the hemG knockout *E. coli* strain in LB liquid media supplemented with a PPO herbicide to identify protoporphyrinogen oxidases that were not sensitive to the PPO herbicide.

The hemG knockout *E. coli* strain was transformed with the bacterial expression vectors containing the confirmed protoporphyrinogen oxidases and cultured in LB liquid media. A saturating amount of the purified crystalline form of one of five different PPO herbicides (acifluorfen, flumioxazin, lactofen, fomesafen, and S-3100), representing three different PPO chemistry subclasses, was added to the media. Recombinant proteins were expressed and the *E. coli* growth rates were measured. Growth curves (OD600) were measured for the different variants in the presence and absence of the PPO herbicides at selected time-points (e.g., eight hours). The growth of a transformed hemG knockout *E. coli* strain on LB media in the presence of a PPO herbicide indicates a protoporphyrinogen oxidase that is an herbicide-insensitive protoporphyrinogen oxidase (iPPO).

Figure 2:
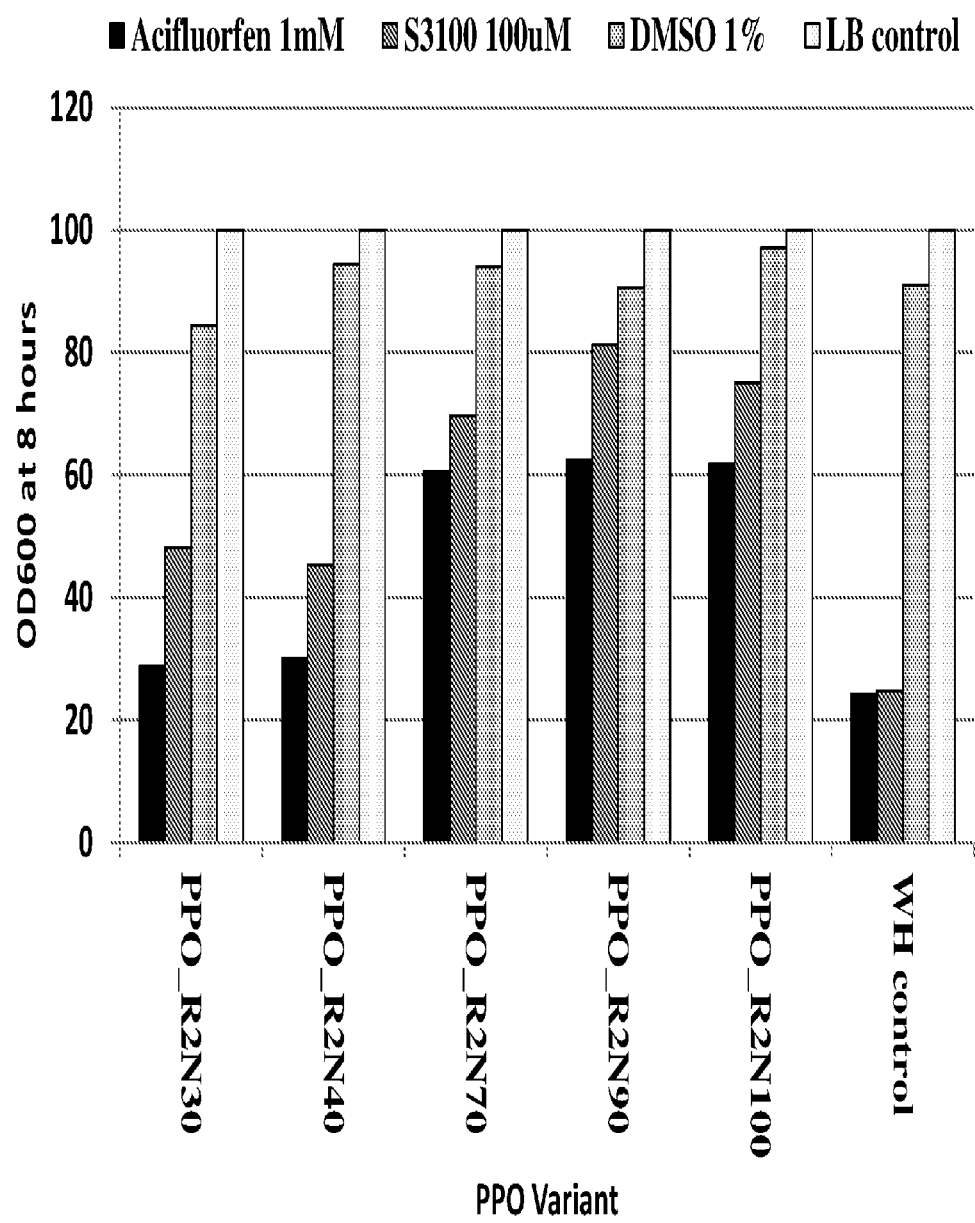
FIG. 2. Assay results from herbicide bacterial screening system with PPO herbicides. Assay of HemY R2N30 (SEQ ID NO:1), Hem Y R2N40 (SEQ ID NO:2), HemY R2N70 (SEQ ID NO:3), HemY R2N90 (SEQ ID NO:4), HemY R2N100 (SEQ ID NO:5), and negative control *Amaranthus tuberculatus* (WH) PPO (SEQ ID NO:80) in the presence of acifluorfen and S-3100 PPO herbicides

The novel putative protoporphyrinogen oxidases were used with this assay to test for insensitivity to PPO herbicides. Expression of *E. coli* HemG (SEQ ID NO: 76), HemY PPO R1N473 (SEQ ID NO: 13), HemY PPO R1N533 (SEQ ID NO: 14); or HemY PPO R1N171 (SEQ ID NO: 15) conferred normal growth rates on the hemG knockout *E. coli* strain in minimal media in the presence of acifluorfen, flumioxazin, lactofen, or fomesafen PPO herbicides, therefore indicating that these proteins were highly herbicide-insensitive protoporphyrinogen oxidases (iPPO). Data are provided in FIG. 1. Bacteria transformed with constructs encoding HemY PPO R1 N311 (SEQ ID NO:16) or HemY PPO R1 N333 (SEQ ID NO:17) did not grow in the presence of any of acifluorfen, flumioxazin, lactofen, or fomesafen, indicating that these proteins did not confer tolerance to any of these four PPO herbicides. Expression of HemY R2N30 (SEQ ID NO:1) or Hem Y R2N40 (SEQ ID NO:2) conferred normal growth rates on the hemG knockout *E. coli* strain in minimal media in the presence of acifluorfen and S-3100, but at higher levels these two enzymes showed sensitivity to both herbicides. The growth rate was slower for the hemG knockout *E. coli* strain containing HemY R2N70 (SEQ ID NO:3), HemY R2N90 (SEQ ID NO:4), or HemY R2N100 (SEQ ID NO:5), but tolerance to acifluorfen and S-3100 was much better than for the hemG knockout *E. coli* strain containing either the R2N30 (SEQ ID NO:1) and R2N40 (SEQ ID NO:2). Data are provided in FIG. 2. The hemG knockout *E. coli* strain expressing the *A. tuberculatus* PPO (SEQ ID NO:80) was used as a negative control and was sensitive to all of the PPO herbicides. Using this assay, a large number of novel or engineered proteins can be screened to confirm protoporphyrinogen oxidase activity in the presence of PPO herbicide(s).

Example 3: Protoporphyrinogen Oxidase (PPO) Enzyme Assay

Novel protoporphyrinogen oxidases were characterized using an enzyme assay. This assay used recombinant HemY PPO proteins with plant plastid extract and PPO substrate to identify protoporphyrinogen oxidases that had activity in the presence of a PPO herbicide.

Plant plastid extract was produced used etioplasts and chloroplasts that were prepared from etiolated cotyledons (soybean, *Glycine max*), etiolated leaves/coleoptiles (corn, *Zea mays*) and unfolded apical leaves (*A. tuberculatus*) generally by the procedure described by Grossmann (2010). Soybean (A3555) and corn (LH244) seeds were placed between two sheets of moist germination paper (Anchor Paper Company, Saint Paul, Minn.) in a beaker of water in continuous darkness for eight to ten days. *A. tuberculatus* plants were grown for 30 days in the greenhouse. Tissue was collected, placed between moist sheets of paper towels and ground to fine powder with a mortar and pestle in liquid nitrogen. Homogenization buffer (50 mM Tris-HCl, pH 7.4, 500 mM sucrose, 1 mM EDTA, 1 mM magnesium chloride, and 2 g/liter bovine serum albumin) was added to the frozen powder at 4:1 (ml homogenization buffer to g fresh weight tissue), mixed vigorously and filtered through four layers of pre-moistened Miracloth. The filtrate was centrifuged at 9299 g for five minutes. The pellet was resuspended in homogenization buffer and centrifuged at 150 g for two minutes. The supernatant solution was centrifuged at 4000 g for fifteen minutes. All centrifugation steps were carried out a 4° C. The pellet (intact plastid fraction) was resuspended in 50 mM Tris-HCl (pH 7.4), 2 mM EDTA and 20% (v/v) glycerin and stored in aliquots at −80° C. Total protein in plastid preparations was measured by the method of Bradford (1976) with bovine serum albumin as the standard.

Recombinant PPO enzymes were expressed in *E. coli* HemG knockout cell line and extracted for the enzyme assay. Bacterial cells from an overnight culture were used to inoculate 20 ml of fresh media. These cultures were allowed to grow for approximately 48 hrs at 20° C. to a dense culture. Bacterial cells were collected by centrifugation and the cell pellets stored at −80° C. until enzyme assays were performed. Frozen bacterial pellets were resuspended in extraction buffer (50 mM Tris-HCl, pH 7.6, 1 mM EDTA & 1 mM $MgCl_2$) and sonicated (Sonics VibraCell™) for 30 seconds in an ice bath with a one-minute rest period between cycles. For *E. coli* transformed with a construct encoding *E. coli* HemG (SEQ ID NO: 76) the broken cells were centrifuged at 200 g for 2 minutes at 4° C. and the supernatant solution was used for PPO enzyme assays after dilution with extraction buffer. Frozen cell pellets prepared from bacteria transformed with a construct encoding R1N473 (SEQ ID NO:13), R1N171 (SEQ ID NO:15), R1N533 (SEQ ID NO:14), R2N30 (SEQ ID NO:1), R2N40 (SEQ ID NO:2), R2N90 (SEQ ID NO:4), or R2N100 (SEQ ID NO:5) were centrifuged at 9400 g for 10 minutes at 4° C. The pellet fraction from this supernatant solution was prepared by ultracentrifugation at 100,000 g for one hour at 4° C. to 7° C. and resuspended in extraction buffer for PPO assays. Total protein was measured by the method of Bradford (1976) with bovine serum albumin as the standard.

The PPO substrate protoporphyrinogen IX (protogen) was prepared by reduction of commercially available protoporphyrin with sodium mercury amalgam as described by Jacobs and Jacobs (1999). Protoporphyrin (proto) was added to 0.01N potassium hydroxide in 20% ethanol and stirred in the dark until dissolved (about 40 minutes). A volume of 0.8 ml of proto was placed in a 2-ml polypropylene vial with a screw-top cap containing an O-ring, and about 1 g (a spatula tipful, oil drained off) of sodium mercury amalgam (Product Number 451908, Sigma-Aldrich, St. Louis, Mo., stored under oil) was added. The tube was capped and mixed vigorously with a vortex mixer and vented about every 30 seconds by loosening the cap until the solution was no longer fluorescing red under a UV light (about five minutes). The reaction vial was flushed with argon and centrifuged briefly to pellet the remaining sodium amalgam. The supernatant solution was diluted 1:1 (v/v) with a solution of 0.1M DTT and 0.5M Tris-HCl, pH 7.5 and the vial flushed with argon. The protogen solution was split into smaller aliquots into 0.5 ml polypropylene capped tubes which were flushed with argon immediately after the aliquot was added. Capped tubes were covered with aluminum foil and stored at −80° C. For the enzyme assay, the thawed protogen aliquots were stored covered on ice, and used on the same day. The concentration of protogen in the preparation was calculated by subtracting the proto concentration, as measured by fluorescence HPLC (method described by Matsumoto, 1994), in the final protogen solution (typically about 1% of starting material) from the proto concentration in the starting material and assuming no significant impurities in either sample. Protogen prepared and stored under these conditions was stable at least six months.

A PPO enzyme assay was conducted to measure PPO activity using the plant plastid extract and bacterial extract preparations with the PPO substrate. PPO activity was measured generally as described by Grossmann (2010). Ten microliters of either plastid extract (40 µg total protein) or bacterial extract (1.1 µg total protein for E. coli HemG (SEQ ID NO: 76); or 45 to 70 µg total protein for R1N473 (SEQ ID NO:13), R1N171 (SEQ ID NO:15), R1N533 (SEQ ID NO:14), R2N30 (SEQ ID NO:1), R2N40 (SEQ ID NO:2), R2N90 (SEQ ID NO:4), or R2N100 (SEQ ID NO:5)) was added to assay buffer (100 mM Tris-HCl, pH 7.4, 5 mM DTT, 1 mM EDTA and 0.085% (v/v) Tween 80) with buffer or with S-3100 (added as a two-microliter volume from a 100× stock solution prepared in acetone). Analytical-grade S-3100 was provided by Sumitomo Chemical Company. All assays were run in a final concentration of 1% (v/v) acetone. The extracts (plastid or bacterial), buffer, and S-3100 were incubated at 30° C. (plant extracts) or 37° C. (bacterial extracts) for five minutes before addition of two microliters of protogen to initiate the assay. All assays were done in a 96-well black polystyrene microtiter plate (Costar® 3925, Corning, Inc., Corning, N.Y.) at a final volume of 200 microliters. After protogen addition (3 µM for $IC_{50}$ measurements; variable for $K_m$ measurements) to all wells, the plate was incubated at 30° C. (plant extracts) or 37° C. (bacterial extracts) before initiating data collection. Fluorescence over time was measured at 30° C. (plant extracts) or 37° C. (bacterial extracts) with excitation and emission wavelengths of 405 mm and 630 mm, respectively, in a SpectraMax® M5 Multi-Mode Microplate Reader (Molecular Devices, Sunnyvale, Calif.). An assay blank was run by adding heat-inactivated (five minutes at 100° C.) extract to the assay mixture. PPO apparent $K_m$ values were calculated using rectangular hyperbola curve-fitting using the Soft-Pro® kinetics software package (Molecular Devices, Sunnyvale, Calif.). The S-3100 $IC_{50}$ values were determined graphically from the semi logarithmic plot of S-3100 concentration versus PPO activity.

Substrate (protoporphyrinogen) binding affinity was measured as the $K_m$. Enzyme activity sensitivity to the PPO herbicide S-3100 was measured as the concentration giving 50% inhibition of control activity ($IC_{50}$). The $K_m$ for the plant PPO enzymes (A. tuberculatus, soybean, or corn) and the bacterial PPO enzymes (E. coli HemG (SEQ ID NO: 76), R1N473 (SEQ ID NO:13), R1N171 (SEQ ID NO:15), R1N533 (SEQ ID NO:14), R2N30 (SEQ ID NO:1), R2N40 (SEQ ID NO:2), R2N90 (SEQ ID NO:4), or R2N100 (SEQ ID NO:5)) were similar, ranging from 0.7 µM to 2.0 µM. Each of the three plant PPO enzymes were sensitive to S-3100 with an $IC_{50}$ of 0.003 to 0.009 µM. The bacterial PPO enzymes R2N30 (SEQ ID NO:1) and R2N40 (SEQ ID NO:2) had an $IC_{50}$ of 0.02 µM and 0.04 µM, respectively, and were 10-fold less sensitive to the herbicide than the plant PPO enzymes. The bacterial PPO enzymes E. coli HemG (SEQ ID NO: 76), R1N473 (SEQ ID NO:13), R1N171 (SEQ ID NO:15), R1N533 (SEQ ID NO:14), R2N90 (SEQ ID NO:4), and R2N100 (SEQ ID NO:5) had an $IC_{50}$ of greater than 100 µM and were measured as insensitive to the herbicide. Data are provided in Table 4.

TABLE 4

| PPO Enzymatic Activity | | |
|---|---|---|
| Source | $K_m$, µM | S-3100 $IC_{50}$, µM |
| A. tuberculatus | 0.7 | 0.009 |
| Soybean | 1.8 | 0.004 |
| Corn | 2.0 | 0.003 |
| E. coli HemG | 1.6 | >100 |
| R1N473 | 1.2 | >100 |
| R1N171 | 0.2 | >100 |
| R1N533 | 0.4 | >100 |
| R2N30 | 0.8 | 0.02 |
| R2N40 | 0.8 | 0.04 |
| R2N90 | 2.8 | >100 |
| R2N100 | 0.4 | >100 |

Example 4: Enzymatic Optimization of Protoporphyrinogen Oxidases

Protein optimization may used to improve or alter the enzymatic properties of protoporphyrinogen oxidases. One or more methods of protein engineering may be used to optimize the enzymes. Non-limiting examples of protein engineering approaches include Alanine-Scanning Mutations; Homology-Scanning Mutations; Pro/Gly Scanning Mutations; Region Swaps or Mutations; and combinations of these various techniques (see, M Lehmann and M Wyss, Current Opinion in Biotechnology 12(4):371-375 (2001); B Van den Burg and VGH Eijsink, Current Opinion in Biotechnology 13(4):333-337 (2002); and Weiss et al., Proceedings of the National Academy of Sciences USA 97(16): 8950-8954 (2000)). Engineered protoporphyrinogen oxidase nucleic acid sequences may be synthesized and cloned into a bacterial expression vector and used to transform the hemG knockout E. coli strain for the initial high-throughput bacterial rescue screen as described in Example 1. The engineered proteins that rescue the hemG knockout E. coli strain may be screened for sensitivity to one or more PPO herbicide(s) using the bacterial growth assay as described in Example 2. The engineered proteins that exhibit tolerance to PPO herbicides in the second screen may then be expressed as recombinant protein in a bacterial expression system, and enzyme characterization may be done using the purified protein as described in Example 3. Engineered proteins that are insensitive to PPO herbicides may be selected for cloning into plant transformation vectors and this may be used to produce transgenic plants for in planta testing.

A library of randomly mutagenized R2N40 coding sequences were produced using a GeneMorph® II Random Mutagenesis Kit (Agilent Technologies, Santa Clara, Calif.). The resulting library of mutagenized bacterial expression vectors was used to transform the hemG knockout E. coli strain and this was plated onto LB media plates containing acifluorifen. Bacterial colonies that grew on the herbicide medium were selected, the transformation plasmids were purified, and the mutant PPO genes were sequenced. Engineered HemY PPO R2N40 enzymes are provided as SEQ ID NO:7-12.

Example 5: Expression and Testing of PPO Enzymes in Soybean Plants

The microbial HemY PPO enzymes were expressed in transgenic soybean plants, and the transgenic plants were analyzed for PPO herbicide tolerance. A set of constructs for high-throughput screening were produced with the same promoter element and 3' UTR operably linked to one of ten different cassettes encoding HemY PPO enzymes R1N171 (SEQ ID NO: 20); R1N473 (SEQ ID NO:18); R1N533 (SEQ ID NO:19); R2N30 (SEQ ID NO:1, 6); R2N40 (SEQ ID NO:2, 7); R2N40opt (SEQ ID NO:9, 10-12); R2N70 (SEQ ID NO:3); R2N90 (SEQ ID NO:4); R2N100 (SEQ ID NO:5); and R1N333 (SEQ ID NO:21) operably linked to one of 39 different transit peptides. For plant transformation, the nucleotide sequences encoding the HemY PPO enzymes were codon optimized for dicot expression. This permitted the side-by-side comparison of the seven different HemY PPO enzymes with thirty-nine different targeting peptides using the same promoter and 3'UTR elements for gene expression The plant transformation constructs were used to transform soybean excised embryos (germplasm A3555) using *A. tumefaciens* and standard methods known in the art. Four hundred explants were inoculated for each construct resulting in twelve containers per construct. A sterile PPO herbicide solution was used for herbicide tolerance testing. The herbicide solution consisted of 0.3 g of S-3100 in crop oil concentrate (5.0 mL) and 495 mL of deionized water. This was filtered through a 0.45 micron Nalgene® Rapid-Flow™ Tissue Culture Filter Unit and Surfactant-Free Cellulose Acetate membrane filter unit (VWR, Radnor, Pa., USA). The resulting sterile solution was shaken before application.

At five weeks post-transformation, four of the twelve plant containers per construct were sprayed with two passes of the sterile PPO herbicide solution. The treated plantlets were then enclosed in the container and received at least 15 hours of light exposure post spray each day for four days. At the end of day four post application of S-3100, the treated plantlets were photographed and scored on a visual scale of green coloration (green coloration was representative of healthy photosynthetic plant tissue as compared to photobleached tissue) versus damage. The scoring values were 0 for poor tolerance, high damage, low green coloration; 1 for some tolerance, average damage, moderate green coloration; and 2 for good tolerance, low damage, high green coloration. The results of herbicide application of S-3100 at five weeks is presented in Table 5, where n.d. indicates the analysis was not conducted. The results indicated that in this high-throughput screening a number of constructs comprising HemY PPO enzymes R1N473 (SEQ ID NO:18); R1N533 (SEQ ID NO:19); R2N30 (SEQ ID NO:1, 6); R2N40 (SEQ ID NO:2, 7); R2N40opt (SEQ ID NO:9, 10-12); and R2N70 (SEQ ID NO:3) provided tolerance to the PPO herbicide. The results indicated that in this high-throughput screening the HemY PPO enzymes R1N171 (SEQ ID NO:20); R2N90 (SEQ ID NO:4); R2N100 (SEQ ID NO:5); and R1N333 (SEQ ID NO:21) did not provide tolerance to the PPO herbicide.

TABLE 5

Tolerance score to S-3100 at 5 weeks for HemY PPO

| Targeting Peptide | R1N171 | R1N473 | R1N533 | R2N30 | R2N40 | R2N40 opt | R2N70 | R2N90 | R2N100 | R1N333 |
|---|---|---|---|---|---|---|---|---|---|---|
| TP1 | 0 | 2 | 0 | 2 | n.d. | 1 | n.d. | n.d. | 0 | n.d. |
| TP2 | 0 | 0 | 2 | n.d. | n.d. | n.d. | 2 | 0 | 0 | 0 |
| TP3 | 0 | 1 | 0 | 1 | n.d. | n.d. | 1 | n.d. | 0 | 0 |
| TP4 | n.d. | 1 | 0 | 2 | n.d. | 0 | 0 | n.d. | 0 | 0 |
| TP5 | 1 | n.d. | n.d. | n.d. | 1 | 1 | n.d. | 0 | 0 | n.d. |
| TP6 | n.d. | 1 | 1 | n.d. | n.d. | 1 | 0 | n.d. | 0 | 0 |
| TP7 | 0 | 1 | 0 | 1 | n.d. | 2 | n.d. | n.d. | n.d. | 0 |
| TP8 | 1 | 1 | n.d. | 2 | 0 | 1 | 0 | 1 | 1 | 0 |
| TP9 | 1 | 1 | n.d. | 2 | 0 | 0 | n.d. | 1 | n.d. | 1 |
| TP10 | 1 | 1 | 1 | 2 | n.d. | n.d. | n.d. | 0 | 1 | n.d. |
| TP11 | 0 | 0 | 0 | 2 | n.d. | 1 | n.d. | n.d. | n.d. | 0 |
| TP12 | 0 | 1 | 0 | 1 | n.d. | 2 | n.d. | 1 | 0 | 1 |
| TP13 | 0 | 0 | 0 | n.d. | n.d. | 0 | n.d. | 0 | n.d. | 0 |
| TP14 | n.d. | 1 | 1 | 1 | n.d. | n.d. | n.d. | 0 | 1 | 0 |
| TP15 | 1 | 1 | 1 | 2 | n.d. | 1 | n.d. | n.d. | 0 | 0 |
| TP16 | 1 | 1 | 2 | 2 | n.d. | 1 | 0 | 0 | n.d. | 0 |
| TP17 | 0 | 1 | n.d. | 1 | n.d. | 1 | n.d. | n.d. | 0 | 0 |
| TP18 | 0 | 0 | 0 | 1 | n.d. | 0 | n.d. | 1 | 1 | 0 |
| TP19 | 1 | 0 | 1 | n.d. | 2 | 1 | n.d. | 1 | 1 | 0 |
| TP20 | 0 | 1 | 1 | 2 | n.d. | 1 | n.d. | 0 | n.d. | n.d. |
| TP21 | 0 | 0 | n.d. | 1 | n.d. | n.d. | 0 | 1 | 0 | 0 |
| TP22 | n.d. | 1 | 2 | 1 | n.d. | n.d. | n.d. | 0 | 0 | 0 |
| TP23 | 1 | 1 | 1 | 1 | n.d. | n.d. | n.d. | 1 | 0 | 1 |
| TP24 | n.d. | 0 | 2 | 2 | n.d. | n.d. | n.d. | 0 | 0 | 0 |
| TP25 | 0 | 1 | 0 | 2 | n.d. | 1 | n.d. | n.d. | 0 | 0 |
| TP26 | 1 | 0 | 1 | 1 | n.d. | 1 | n.d. | n.d. | 1 | 0 |
| TP27 | 0 | 1 | 0 | n.d. | n.d. | 2 | n.d. | 0 | 0 | 1 |
| TP28 | 0 | 2 | 0 | 2 | n.d. | n.d. | n.d. | 0 | 1 | 0 |
| TP29 | 0 | 0 | 1 | 1 | n.d. | 0 | n.d. | 0 | 0 | 1 |
| TP30 | 1 | 1 | n.d. | 1 | n.d. | 0 | n.d. | 0 | 0 | 0 |
| TP31 | 1 | 1 | 1 | 1 | 0 | 0 | 1 | 0 | 1 | 1 |
| TP32 | 0 | 1 | 1 | 1 | n.d. | 0 | n.d. | 0 | 0 | 0 |
| TP33 | 0 | 2 | 0 | n.d. | 2 | 1 | 0 | 0 | 0 | 0 |
| TP34 | n.d. | n.d. | n.d. | 0 | 1 | n.d. | n.d. | n.d. | n.d. | 1 |
| TP35 | 0 | 0 | 1 | 1 | 1 | 1 | n.d. | n.d. | n.d. | n.d. |
| TP36 | n.d. | n.d. | 0 | 1 | 1 | n.d. | n.d. | n.d. | 0 | 1 |
| TP37 | 0 | 0 | 0 | 1 | 1 | 2 | n.d. | n.d. | 0 | n.d. |
| TP38 | n.d. | n.d. | 2 | n.d. | 2 | n.d. | n.d. | n.d. | n.d. | n.d. |
| TP39 | 1 | 1 | 2 | 1 | 2 | 1 | n.d. | n.d. | n.d. | n.d. |

Plants in the non-sprayed containers corresponding to constructs having a high passing score of 2 and a few fails as negative controls were transplanted at approximately 7 weeks post transformation. The R0 plants were grown in a greenhouse under long-day nursery conditions (18 hr light at 80° F. then 6 hr dark at 74° F.) for approximately four weeks. At eleven weeks, the R0 plants were sprayed with two passes of the same herbicide solution (0.3 g of S-3100) described above. Herbicide injury ratings were collected seven days after treatment. Any injury rating of 30% or above was equivalent to non-transgenic soybean injury ratings. The results of the herbicide tolerance application at eleven weeks to the R0 plants are presented in Table 6, where n.d. indicates the analysis was not conducted. The results indicated that plants expressing a number of constructs comprising HemY PPO enzymes R2N30 (SEQ ID NO:1, 6); R2N40 (SEQ ID NO:2, 7); and R2N40opt (SEQ ID NO:9, 10-12) provided tolerance to the PPO herbicide with an injury rating below the non-transgenic control. Plants expressing the HemY PPO enzyme R2N30 (SEQ ID NO:1, 6) provided herbicide tolerance in 16 of the 19 constructs tested, with injury ratings for these constructs of 7% to 25%. Plants expressing the HemY PPO enzymes R2N40 (SEQ ID NO:2, 7) and R2N40opt (SEQ ID NO:9, 10-12) provided herbicide tolerance in 8 of the 11 constructs tested, with injury ratings for these constructs of 20% to 25%. The results indicated that in this high-throughput screening plants expressing the HemY PPO enzymes R1N171 (SEQ ID NO:20); R1N473 (SEQ ID NO:18); R1N533 (SEQ ID NO:19); R2N70 (SEQ ID NO:3); and R1N333 (SEQ ID NO:21) had an injury rating of 30% or above equivalent to non-transgenic control injury ratings and thus did not provide tolerance to the PPO herbicide.

TABLE 6

Tolerance score to S-3100 at 11 weeks for HemY PPO

| Targeting Peptide | R1N171 | R1N473 | R1N533 | R2N30 | R2N40 | R2N40opt | R2N70 | R1N333 |
|---|---|---|---|---|---|---|---|---|
| TP1 | n.d. | 30 | n.d. | 17 | n.d. | 20 | n.d. | n.d. |
| TP2 | n.d. | n.d. | 40 | n.d. | n.d. | n.d. | 30 | n.d. |
| TP3 | n.d. | n.d. | n.d. | n.d. | n.d. | n.d. | n.d. | n.d. |
| TP4 | n.d. | n.d. | n.d. | 25 | n.d. | n.d. | n.d. | n.d. |
| TP5 | n.d. | n.d. | n.d. | n.d. | n.d. | n.d. | n.d. | n.d. |
| TP6 | n.d. | 35 | n.d. | n.d. | n.d. | n.d. | n.d. | n.d. |
| TP7 | n.d. | n.d. | n.d. | 25 | n.d. | 30 | n.d. | n.d. |
| TP8 | n.d. | n.d. | n.d. | 35 | n.d. | 30 | n.d. | 35 |
| TP9 | n.d. | n.d. | n.d. | 20 | n.d. | 25 | n.d. | 35 |
| TP10 | n.d. | n.d. | n.d. | 25 | n.d. | n.d. | n.d. | n.d. |
| TP11 | n.d. | n.d. | n.d. | 25 | n.d. | n.d. | n.d. | n.d. |
| TP12 | n.d. | n.d. | n.d. | n.d. | n.d. | 35 | n.d. | n.d. |
| TP13 | n.d. | n.d. | n.d. | n.d. | n.d. | n.d. | n.d. | n.d. |
| TP14 | n.d. | n.d. | n.d. | 20 | n.d. | n.d. | n.d. | 35 |
| TP15 | n.d. | n.d. | n.d. | 25 | n.d. | n.d. | n.d. | n.d. |
| TP16 | 30 | 40 | 35 | 35 | n.d. | n.d. | n.d. | n.d. |
| TP17 | n.d. | n.d. | n.d. | 25 | n.d. | n.d. | n.d. | n.d. |
| TP18 | n.d. | n.d. | n.d. | 15 | n.d. | n.d. | n.d. | n.d. |
| TP19 | n.d. | n.d. | n.d. | n.d. | 20 | n.d. | n.d. | n.d. |
| TP20 | n.d. | n.d. | n.d. | 15 | n.d. | 20 | n.d. | n.d. |
| TP21 | n.d. | n.d. | n.d. | n.d. | n.d. | n.d. | n.d. | n.d. |
| TP22 | n.d. | n.d. | 35 | 25 | n.d. | n.d. | n.d. | n.d. |
| TP23 | n.d. | n.d. | n.d. | n.d. | n.d. | n.d. | n.d. | n.d. |
| TP24 | n.d. | n.d. | 35 | 15 | n.d. | n.d. | n.d. | n.d. |
| TP25 | n.d. | n.d. | n.d. | 7 | n.d. | n.d. | n.d. | n.d. |
| TP26 | n.d. | n.d. | n.d. | n.d. | n.d. | n.d. | n.d. | n.d. |
| TP27 | n.d. | n.d. | n.d. | n.d. | n.d. | 25 | n.d. | n.d. |
| TP28 | n.d. | 35 | n.d. | 35 | n.d. | n.d. | n.d. | n.d. |
| TP29 | n.d. | n.d. | n.d. | n.d. | n.d. | n.d. | n.d. | n.d. |
| TP30 | n.d. | n.d. | n.d. | 25 | n.d. | n.d. | n.d. | n.d. |
| TP31 | n.d. | n.d. | n.d. | n.d. | n.d. | n.d. | n.d. | n.d. |
| TP32 | n.d. | n.d. | n.d. | n.d. | n.d. | n.d. | n.d. | n.d. |
| TP33 | n.d. | 40 | n.d. | n.d. | 20 | n.d. | n.d. | n.d. |
| TP34 | n.d. | n.d. | n.d. | n.d. | n.d. | n.d. | n.d. | n.d. |
| TP35 | n.d. | n.d. | n.d. | n.d. | n.d. | n.d. | n.d. | n.d. |
| TP36 | n.d. | n.d. | n.d. | 25 | n.d. | n.d. | n.d. | n.d. |
| TP37 | n.d. | n.d. | n.d. | n.d. | n.d. | 25 | n.d. | n.d. |
| TP38 | n.d. | n.d. | 35 | n.d. | 25 | n.d. | n.d. | n.d. |
| TP39 | n.d. | 30 | 35 | n.d. | n.d. | n.d. | n.d. | n.d. |

What is claimed is:

1. A recombinant DNA molecule comprising a heterologous promoter operably linked to a nucleic acid sequence encoding a protein that comprises a polypeptide sequence with at least 90% sequence identity to a polypeptide sequence selected from the group consisting of: SEQ ID NO:2, SEQ ID NO:7, SEQ ID NO:8, SEQ ID NO:9, SEQ ID NO:10, SEQ ID NO:11, and SEQ ID NO:12, wherein the protein has herbicide-insensitive protoporphyrinogen oxidase activity.

2. The recombinant DNA molecule of claim 1, wherein the nucleic acid sequence comprises a polynucleotide sequence selected from the group consisting of SEQ ID NO:27, SEQ ID NO:32, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:48.

3. The recombinant DNA molecule of claim 1, wherein the protein comprises an amino acid sequence selected from the group consisting of SEQ ID NO:2, SEQ ID NO:7, SEQ ID NO:8, SEQ ID NO:9, SEQ ID NO:10, SEQ ID NO:11, and SEQ ID NO:12.

4. The recombinant DNA molecule of claim 1, wherein the heterologous promoter is functional in a plant cell.

5. The recombinant DNA molecule of claim 4, wherein the nucleic acid sequence is operably linked to a DNA molecule encoding a targeting sequence that functions to localize the protein within a cell.

6. A DNA construct comprising the recombinant DNA molecule of claim 1.

7. The DNA construct of claim 6, wherein the recombinant DNA molecule further comprises an operably linked DNA molecule encoding a targeting sequence that functions to localize the protein within a cell.

8. The DNA construct of claim 7, wherein the protein confers PPO herbicide tolerance to said cell.

9. The DNA construct of claim 6, wherein the DNA construct is present in the genome of a transgenic plant, seed, or cell.

10. A recombinant polypeptide that comprises a polypeptide sequence that has at least 90% sequence identity to the full length of an amino acid sequence chosen from SEQ ID NO:2, SEQ ID NO:7, SEQ ID NO:8, SEQ ID NO:9, SEQ ID NO:10, SEQ ID NO:11, and SEQ ID NO:12, wherein the recombinant polypeptide has herbicide-insensitive protoporphyrinogen oxidase activity.

11. A transgenic plant, seed, cell, or plant part comprising the recombinant DNA molecule of claim 1.

12. The transgenic plant, seed, cell, or plant part of claim 11, wherein the transgenic plant, seed, cell, or plant part comprises an additional transgenic herbicide tolerance trait.

13. The transgenic plant, seed, cell, or plant part of claim 11, defined as comprising herbicide tolerance to at least one PPO herbicide.

14. A transgenic plant, seed, cell, or plant part comprising the recombinant polypeptide of claim 10.

15. A method for conferring PPO herbicide tolerance to a plant, seed, cell, or plant part comprising: heterologously expressing in said plant, seed, cell, or plant part the recombinant polypeptide of claim 10.

16. The method of claim 15, wherein the herbicide tolerance is to at least one PPO herbicide selected from the group consisting of: acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil and S-3100.

17. A method of plant transformation, the method comprising the steps of:
   a) introducing the recombinant DNA molecule of claim 1 into a plant cell; and
   b) regenerating a plant therefrom that comprises the recombinant DNA molecule.

18. The method of claim 17, further comprising the step of selecting a plant that is tolerant to at least one PPO herbicide.

19. The method of claim 17, further comprising the step of crossing the regenerated plant with itself or with a second plant and collecting seed from the cross.

20. A method for controlling weeds in a plant growth area, comprising contacting a plant growth area comprising the transgenic plant or seed of claim 11 with at least one PPO herbicide, wherein the transgenic plant or seed is tolerant to the PPO herbicide and wherein at least a first weed is controlled in the plant growth area by the PPO herbicide.

21. A method of producing a plant tolerant to a PPO herbicide and at least one other herbicide, the method comprising:
   a) obtaining a plant according to claim 11;
   b) crossing the transgenic plant with a second plant comprising tolerance to the at least one other herbicide, and
   c) selecting a progeny plant resulting from said crossing that comprises tolerance to a PPO herbicide and the at least one other herbicide.

22. A method for reducing the development of herbicide tolerant weeds, the method comprising:
   a) cultivating in a crop growing environment a plant according to claim 12; and
   b) applying a PPO herbicide and at least one other herbicide to the crop growing environment, wherein the crop plant is tolerant to the PPO herbicide and the at least one other herbicide.

23. The method of claim 22, wherein the PPO herbicide is selected from the group consisting of acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil and S-3100.

24. The method of claim 22, wherein the at least one other herbicide is selected from the group consisting of: an ACCase inhibitor, an ALS inhibitor, an EPSPS inhibitor, a synthetic auxin, a photosynthesis inhibitor, a glutamine synthesis inhibitor, a HPPD inhibitor, a PPO inhibitor, and a long-chain fatty acid inhibitor.

25. The method of claim 24, wherein the ACCase inhibitor is an aryloxyphenoxy propionate or a cyclohexanedione; the ALS inhibitor is a sulfonylurea, imidazolinone, triazoloyrimidine, or a triazolinone; the EPSPS inhibitor is glyphosate; the synthetic auxin is a phenoxy herbicide, a benzoic acid, a carboxylic acid, or a semicarbazone; the photosynthesis inhibitor is a triazine, a triazinone, a nitrile, a benzothiadiazole, or a urea; the glutamine synthesis inhibitor is glufosinate; the HPPD inhibitor is an isoxazole, a pyrazolone, or a triketone; the PPO inhibitor is a diphenylether, a N-phenylphthalimide, an aryl triazinone, or a pyrimidinedione; or the long-chain fatty acid inhibitor is a chloroacetamide, an oxyacetamide, or a pyrazole.

\* \* \* \* \*